US010029016B2

(12) United States Patent
Irvine et al.

(10) Patent No.: US 10,029,016 B2
(45) Date of Patent: *Jul. 24, 2018

(54) IMMUNOSTIMULATORY COMPOSITIONS AND METHODS OF USE THEREOF

(71) Applicant: Massachusetts Institute of Technology, Cambridge, MA (US)

(72) Inventors: Darrell Irvine, Arlington, MA (US); Haipeng Liu, Malden, MA (US)

(73) Assignee: Massachusetts Insitute of Technology, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/790,432

(22) Filed: Jul. 2, 2015

(65) Prior Publication Data

US 2016/0095936 A1     Apr. 7, 2016

Related U.S. Application Data

(62) Division of application No. 13/844,075, filed on Mar. 15, 2013, now Pat. No. 9,107,904.

(60) Provisional application No. 61/620,518, filed on Apr. 5, 2012.

(51) Int. Cl.
| | |
|---|---|
| *A61K 39/00* | (2006.01) |
| *A61K 39/39* | (2006.01) |
| *C07K 14/76* | (2006.01) |
| *A61K 47/48* | (2006.01) |
| *A61K 39/12* | (2006.01) |
| *A61K 39/21* | (2006.01) |

(52) U.S. Cl.
CPC .... *A61K 47/48323* (2013.01); *A61K 39/0005* (2013.01); *A61K 39/0011* (2013.01); *A61K 39/12* (2013.01); *A61K 39/21* (2013.01); *A61K 39/39* (2013.01); *A61K 47/48038* (2013.01); *A61K 47/48046* (2013.01); *A61K 47/48284* (2013.01)

(58) Field of Classification Search
USPC .......... 424/194.1, 28.3, 283.1; 530/300, 363, 530/367; 536/23.1
See application file for complete search history.

(56) References Cited

U.S. PATENT DOCUMENTS

| | | | |
|---|---|---|---|
| 7,615,539 | B2 | 11/2009 | Uhlmann |
| 7,741,297 | B2 | 6/2010 | Jiang |
| 2007/0104654 | A1 | 5/2007 | Hsieh |
| 2007/0154398 | A1 | 7/2007 | Wang |
| 2010/0183639 | A1 | 7/2010 | Uhlmann |
| 2012/0087949 | A1 | 4/2012 | Tan |
| 2012/0121606 | A1* | 5/2012 | Ruben ............... A61K 47/48561 424/158.1 |
| 2012/0129199 | A1* | 5/2012 | Daftarian ......... G01N 33/54346 435/7.92 |
| 2014/0162944 | A1* | 6/2014 | Tiberg ................. A61K 9/0019 514/5.3 |
| 2014/0294932 | A1* | 10/2014 | Kim ....................... A61K 9/127 424/450 |
| 2015/0044208 | A1* | 2/2015 | Castanheira ......... C07K 16/241 424/134.1 |
| 2015/0232514 | A1* | 8/2015 | Dockal .................... C07K 7/08 514/14.5 |
| 2015/0283205 | A1* | 10/2015 | Phipps ............... C12N 15/1138 514/21.2 |

FOREIGN PATENT DOCUMENTS

| | | |
|---|---|---|
| EP | 0491628 | 6/1992 |
| WO | 94001138 | 1/1994 |
| WO | 9426778 | 11/1994 |
| WO | 2004029277 | 4/2004 |
| WO | 2005117984 | 12/2005 |
| WO | 2008115319 | 9/2008 |
| WO | 2008121949 | 10/2008 |
| WO | 2008139262 | 11/2008 |
| WO | 2010071852 | 6/2010 |

OTHER PUBLICATIONS

Bachman and Jennings, "Vaccine delivery: a matter of size, geometry, kinetics and molecular patterns", Nat. Rev. Immunol., 10:787-96 (2010).
Ballas, et al., "Divergent therapeutic and immunologic effects of oligodeoxynucleotides with distinct CpG motifs", J. Immunol., 167:4878-86 (2001).
Bedoui, et al., "Cross-presentation of viral and self antigens by skin-derived DC103+ dendritic cells", Nat. Immunol., 10:488-95 (2009).
Bourquin et al., "Targeting CpG oligonucleotides to the lymph node by nanoparticles elicits efficient antitumoral immunity", J. Immunol., 181:2990-8 (2008).
Cai, et al., "Lymphatic drug delivery using engineered liposomes and solid lipid nanoparticles", Adv. Drug Delivery Rev., 63:901-8 (2011).
Cuomo, et al., "Oligonucleotides and polynucleotides condensation onto liposome surface: effects of the base and of the nucleotide length", Colliods Surf B Biointerfaces, 104(1):239-44 (2013).

(Continued)

*Primary Examiner* — Jane Zara
(74) *Attorney, Agent, or Firm* — Pabst Patent Group LLP

(57) ABSTRACT

Lipid conjugates for enhanced delivery of cargo to the lymph nodes are disclosed. The lipid conjugates typically include three domains: a lipophilic domain that binds to albumin, a polar block domain, and a cargo such as a molecular adjuvant or immunostimulatory compound (such as an oligonucleotide) or antigenic peptide. Depending on the cargo, the length and compositions of the polar block can be tailored to push the equilibrium toward albumin binding, stable micelle formation, or cell insertion. The conjugates can be administered to a subject, for example, a subject with cancer or an infection, to induce or enhance a robust immune response in the subject.

36 Claims, 31 Drawing Sheets

(56) References Cited

OTHER PUBLICATIONS

Dass, "Lipoplex-mediated delivery of nucleic acids: factors affecting in vivo transfection", J Mol. Med., 82(9):579-91 (2004).
Davis, "G-quartets 40 years later: from 5'-GMP to molecular biology and supramolecular chemistry", Angew. Chem. Int. Ed. Engl., 43:668-98 (2004).
Hubbel, et al., "Materials engineering for immunomodulation", Nature, 462:449-60 (2009).
Johansena, et al., "Lympho-geographical concepts in vaccine delivery", J. Control Rel., 148:56-62 (2010).
Keler, et al., "Antibody-targeted vaccines", Oncogene, 26:3758-67. (2007).
Klinman, "Immunotherapeutic uses of CpG oligodeoxynucleotides", Nat. Rev. Immunol., 4:249-59 (2004).
Liu, et al., "Membrane Anchored Immunostimulatory Oligonucleotides for In Vivo Cell Modification and Localized Immunotherapy", J. Angew. Chem., Int. Ed.
Manolova, et al., "Nanoparticles target distinct dendritic cell populations according to their size", Eru. J. Immunol., 38:1404-13 (2008).
Mishra, et al., "Improved leishmanicidal effect of phosphorotioate antisense oligonucleotides by LDL-mediated delivery", Biochim. Biophysica Acta, 1264 (2):229-37 (1995).
Moon, et al., "Engineering nano- and microparticles to tune immunity", Adv. Mater., 24:3724-46 (2012).
Oyewumi, et al., "Nano-microparticles as immune adjuvants: correlating particle sizes and the resultant immune responses", Expert Rev. Vaccines, 9:1095-107 (2010).
Pal and Ramsey, "The role of the lymphatic system in vaccine trafficking and immune response", Adv. Drug Delivery Rev., 63:909-22 (2011).
Pape, et al., "The humoral immune response is initiated in lymph nodes by B cells that acquire soluble antigen directly in the follicles", Immunity., 26:491-502 (2007).
Paramasivan, et al., "Circular dichroism of quadruplex DNAs: applications to structure, cation effects and ligand binding", Method,s 43:324-31 (2007).
Perrie, et al., "Vaccine adjuvant systems: enhancing the efficacy of sub-unit protein antigens", Int. J. Pharm., 364:272-80 (2008).
Reddy, et al., "Exploiting lymphatic transport and complement activation in nanoparticle vaccines", Nat. Biotechnol., 25:1159-64 (2007).
Schnorrer, et al., "The dominant role of CD8+ dendritic cells in cross-presentation is dictated by antigen capture", PNAS, 103:10729-34 (2006).
Senti, et al., "Intralymphatic immunotherapy", Curr. Opin. Allergy Clin. Immunol., 9:537-43 (2009).
Singh, et al., "Nanoparticles and microparticles as vaccine-delivery systems", Exp RevVaccine, 6(5):797-808 (2007).
Smith, et al., "Cutting edge; conventional CD8 alpha+ dendritic cells are preferentially involved int CTL priming after footpad infection with herpes simplex virus-1", J. Immunol., 170:4437-40 (2003).
St. John, et al., "Synthetic mast-cell granules as adjuvants to promote and polarize immunity in lymph nodes", Nature Materials, 11:250-7 (2012).
Storhoff, et al., "Onepot colorimetric differentiation of polynucleotides with single base imperfections using gold nanoparticle probes", J Am. Chem. Soc., 120:1959-64 (1999).
Tacken, et al., "Dendritic-cell immunotherapy: from ex vivo loading to in vivo targeting", Nat. Rev. Immunol., 10:790-802 (2007).
Tenbusch, et al., "Immunogenicity of DNA vaccines encoding simian immunodeficiency virus antigen targeted to dendritic cells in rhesus macaques", PLoS ONE, 7:e39038 (2012).
Vollmer and Krieg, "Immunotherapeutic applications of CpG oligodeoxynucleotide TLR9 agonists", Adv. Drug Delivery Rev., 61:195-204 (2009).
von Beust, et al., "Improving the therapeutic index of CpG oligodeoxynucleotides by intralymphatic administration", Eur. J. Immunol., 35:1869-76 (2005).
Wilson, et al., "Lipid-based delivery of CpG oligonucleotides enhances immunotherapeutic efficacy", Adv. Drug Deliv. Rev., 61(3):233-42 (2009).
Zepp, "Principles of vaccine design Lessons from nature", Vaccine, 28S:C14-C24 (2010).
Andrews, et al., "Conjugation of lipid and CpG-containing oligonucleotide yields an efficient method for liposome incorporation", Bioconj Chem., 22(7)1279-86 (2011).
Bagby, et al., "Impact of molecular weight on lymphatic drainage of a biopolymer-based imaging agent", Pharmaceutics., 4:276-95 (2012).
Fujita, et al., "Overview and outlook of Toll-like receptor ligand-antigen conjugate vaccines", Ther. Deliv., 3:749-60 (2012).
Goldblatt, "Conjugate vaccines", Clin. Exp. Immunol., 119:1-3 (2000).
Heegaard, et al., "Dendrimers for vaccine and immunostimulatory uses. A review", Bioconj Chem., 21:405-18 (2010).
Kaminskas, et al., "PEGylation of polylysine dendrimers improves absorption and lymphatic targeting following SC administration in rats", J. Control Release, 140:108-16 (2009).
Kaminskas, et al., "Targeting the lymphatics using dendritic polymers (dendrimers)", Adv. Drug Deliv. Rev., 63:890-900 (2011).
Kobayashi, et al., "Delivery of gadolinium-labeled nanoparticles to the sentinel lymph node: comparison of the sentinel node visualization and estimations of intra-nodal gadolinium concentration by the magnetic resonance imaging", J. Control Release, 111:343-51 (2006).
Kobayashi, et al., "Multi-Modal Nano-Probes for Radionuclide and 5-color Near Infrared Optical Lymphatic Imaging", ACS Nano., 1:258-64 (2007).
Liu, et al., "DNS-based miscelles: Synthesis, micellar properties and size-dependent cel permeability", Chem, 16(12):3791-7 (2010).
Liu, et al., "Guiding principles in the design of molecular bioconjugates for vaccine applications", Bioconjug. Chem., 26(5):791-801 (2015).
McLennan, et al., "Subcutaneous drug delivery and the role of the lymphatics", Drug Discovery Today: Technol, ;2:89-96 (2005).
Moyle, et al., "Modern Subunit Vaccines: Development, Components, and Research Opportunities", ChemMedChem., 8:360-76 (2013).
Pilishvili, et al., "Sustained reductions in invasive pneumococcal disease in the era of conjugate vaccine", J. Infec. Dis., 201:32-41 (2010).
Rao, et al., "Biodegradable PLGA based nanoparticles for sustained regional lymphatic drug delivery", J. Pharm., Sci., 99:2018-31 (2010).
Robbins, et al., "Polysaccharide-ptotein conjugates: a new generation of vaccines",. J. Infect. Dis., 161:821-32 (1990).
Slovin, et al., "Carbohydrate vaccines as immunotherapy for cancer", Immunol. Cell Biol., 83:418-28 (2005).
Takakura, et al., "Development of a novel polymeric prodrug of mitomycin C, mitomycin C-dextran conjugate with anionic charge. II. Disposition and pharmacokinetics following Intravenous and intramuscular administration", Int. J. Pharm., 37:145-54 (1987).
Tsopelas, et al., "Why certain dyes are useful for localizing the sentinel lymph node", J. Nucl. Med., 43:1377-82 (2002).
Wong, et al., "Lymphatic drainage of skin to a sentinel lymph node in a feline model", Ann. Surg., 214:637-40 (1991).
Wu, et al., "Fluorescence imaging of the lymph node uptake of proteins in mice after subcutaneous injection: molecular weight dependence", Pharm. Res., 29:1843-53 (2012).
Kwong, et al., "Induction of potent anti-tumor responses while eliminating systemic side effects via liposome-anchored combinatorial immunotherapy", Biomaterials, 32:5134-47 (2011).

* cited by examiner

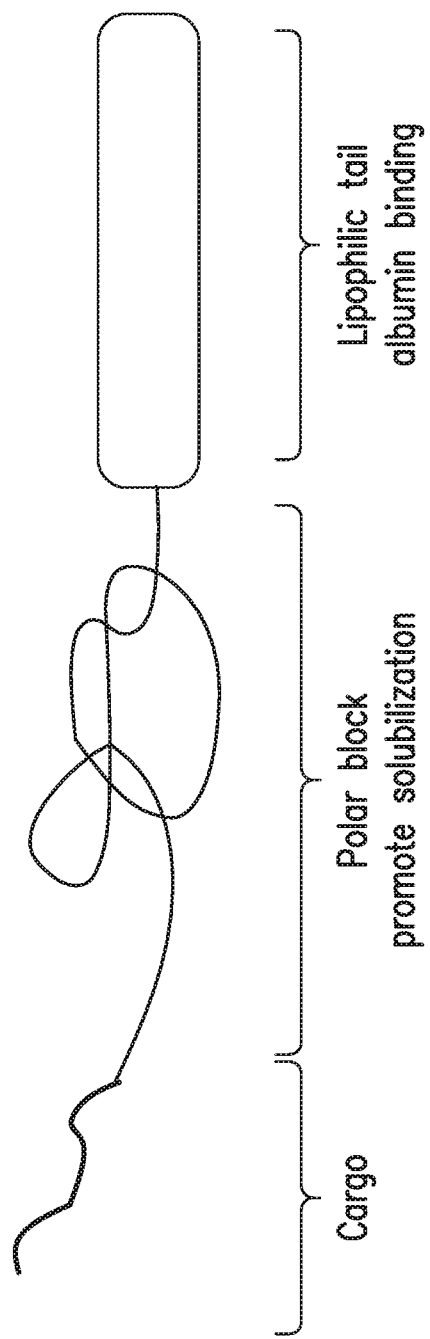
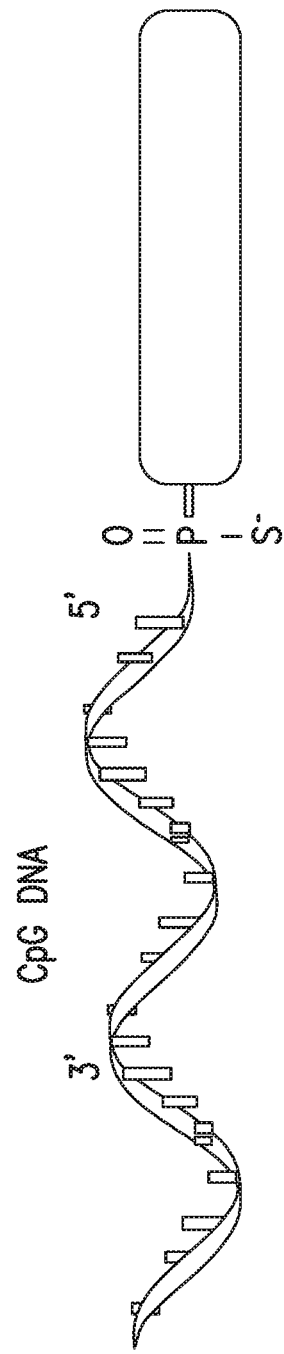
FIG. 1A
FIG. 1B

000# IMMUNOSTIMULATORY COMPOSITIONS AND METHODS OF USE THEREOF

CROSS-REFERENCE TO RELATED APPLICATIONS

This application is a divisional of U.S. application Ser. No. 13/844,075, filed Mar. 15, 2013, which claims benefit of U.S. Provisional Application No. 61/620,518 filed Apr. 5, 2012, and are hereby incorporated by reference in their entirety.

STATEMENT REGARDING FEDERALLY SPONSORED RESEARCH OR DEVELOPMENT

This invention was made with Government support under Grant Nos. P01 AI104715, U19 AI091693, P30 CA014051, and RO1 AI095109 awarded by the National Institutes of Health and under Contract Nos. W911NF-13-D-0001 and W911NF-07-D-0004 awarded by the Army Research Office. The Government has certain rights in the invention.

FIELD OF THE INVENTION

This invention relates to the field of vaccine technology, and more specifically to albumin-binding lipids conjugated to cargo and which efficiently target the cargo to the lymph nodes.

BACKGROUND OF THE INVENTION

Subunit vaccines present an antigen to the immune system without introducing viral particles in an effort to generate an immune response that is effective against that antigen. Such subunit vaccines are often poorly immunogenic and require co-administration of one or more adjuvants to generate an effective immune response (Perrie, Y., et al., *Int. J. Pharm.* 364, 272-280 (2008); Zepp, F. *Vaccine* 28S C14-C24 (2010)). Immunostimulatory oligonucleotides, such as those containing unmethylated cytosine-phosphate-guanine ("CG" or "CpG") motifs, can be used as an adjuvant to stimulate both cellular and humoral immune responses (Vollmer, J. & Krieg, A. M. *Adv. Drug Delivery Rev.* 61, 195-204 (2009); Klinman, D. M. *Nat. Rev. Immunol.* 4, 249-259 (2004)). A challenge to the clinical application of oligonucleotides as a vaccine adjuvant is the lack of an efficient system with which to target the oligonucleotides in vivo to the immune cells of the lymphatic system (Von Beust, B. R., et al. *Eur. J. Immunol.* 35, 1869-1876 (2005); Bourquin, C., et al., *J. Immunol.* 181, 2990-2998 (2008)).

Transporting antigens/adjuvants from the location of injection to secondary lymph nodes is challenging and depends upon the complex physiology of the lymphatic system (Pal, I. & Ramsey, J. D. *Adv. Drug Delivery Rev.* 63, 909-922 (2011); Reddy, S. T., et al., *Nat. Biotechnol.* 25, 1159-1164 (2007)). Antigens/adjuvants introduced into the body may be taken up by immune dendritic cells (DCs) at the injection site and then carried to lymph node through DC trafficking (e.g., cell associated antigen or larger particles, >200 nm). Alternatively, they could directly enter the lymphatic vessels and drain into the secondary lymphoid organs (e.g., small particles, <200 nm) where a significant portion of the immune cells reside (Bachmann, M. F. & Jennings, G. T. *Nat. Rev. Immunol.* 10, 787-796 (2010); Reddy, S. T., et al., *Nat. Biotechnol.* 25, 1159-1164 (2007); Singh, M. *Vaccine adjuvant and delivery system.* Wiley. (2007); Oyewumi, M. O., et al., *Expert Rev. Vaccines* 9, 1095-1107 (2010); Cai, S., et al., *Adv. Drug Delivery Rev.* 63, 901-908 (2011); Manolova, V., et al. *Eru. J. Immunol.* 38, 1404-1413 (2008)).

Soluble antigen/adjuvant compounds flush through lymph nodes within hours (Pape, et al., *Immunity* 26, 491-502 (2007)), providing only a brief exposure to the vaccine. Attempts to enhance the delivery of antigens/adjuvants to lymph nodes following parenteral injection have included the use of depot-forming adjuvants or particulate carriers that are preferentially internalized by antigen presenting cells (Johansena, et al., *Journal of Controlled Release*, 148, 56-62 (2010), Moon, et al., *Adv. Mater.*, 24, 3724-3746 (2012), Bachmann and Jennings, *Nat. Rev. Immunol.* 10, 787-796 (2010), Hubbel, et al., *Nature*, 462, 449-460 (2009), Pal, & Ramsey, *J. D. Adv. Drug Delivery Rev.*, 63, 909-922 (2011), Reddy, et al., *J. A. Nat. Biotechnol.*, 25, 1159-1164 (2007), John, et al., *Nature Materials*, 11, 250-257 (2012)) but these approaches do not achieve the potency of direct injection of vaccines into lymphoid tissues (Senti, et al., *Curr. Opin. Allergy Clin. Immunol.*, 9:537-543 (2009)). Molecularly-targeted vaccines based on the conjugation of antigen to antibodies or other ligands targeting dendritic cells not only reach DCs in the draining lymph nodes, but also drain into the systemic circulation and access DCs in distal tissues (Keler, et al., *Oncogene*, 26, 3758-67 (2007), Tacken, et al., *Nat. Rev. Immunol.*, 10, 790-802 (2007), Tenbusch, et al., *PLoS ONE*, 7, e39038 (2012)). Such systemic delivery may promote tolerance unless inflammatory adjuvants are also systemically co-administered, an approach likely to give rise to unacceptable toxicity in prophylactic vaccines.

However, there remains a need for efficient delivery systems to target antigens/adjuvants to lymphoid-residing antigen presenting cells, especially CD8+ DCs, a step that is important for inducing a cytotoxic T lymphocyte (CTL) response as CD8+ DCs are the major DCs capable of cross-presentation (Smith, C. M., et al., *J. Immunol.* 170, 4437-4440 (2003); Schnorrer, P., et al., *Proc. Natl. Acad. Sci. USA* 103, 10729-10734 (2006); Bedoui, S., et al., *Nat. Immunol.* 10, 488-495 (2009)), a process required for presenting extracellular antigens within MHC class I molecules to CD8+ T cells.

Therefore, it is an object of the invention to provide compositions and methods of increasing delivery of vaccine adjuvants to the lymph nodes.

It is also an object to the invention to provide compositions and method for increasing delivery of vaccine antigens to the lymph nodes.

It is another object of the invention to provide immunogenic compositions and methods of use thereof for increasing delivery a combination of vaccine adjuvants and antigens to the lymph nodes.

It is a further object of the invention to provide immunogenic compositions and methods of use thereof for inducing an immune response.

It is another object of the invention to provide compositions and methods for increasing retention of vaccine adjuvants and antigens locally, at the site of administration and ipsilateral draining lymph nodes.

It is a further object of the invention to provide methods for increasing local immune responses.

SUMMARY OF THE INVENTION

It has been discovered that albumin-binding lipids can be conjugated to cargo and efficiently target the cargo to the lymph nodes in vivo. It is believed that upon in vivo introduction, the lipid conjugates bind to endogenous albumin, which prevents the conjugates from rapidly flushing into the bloodstream and instead re-targets them to lymphatics and draining lymph nodes where they accumulate due to filtering of albumin by antigen presenting cells. When the lipid conjugate includes an immunostimulant such as an immunostimulatory oligonucleotide or antigenic peptide, the conjugates can induce or enhance a robust immune response.

The amphiphilic albumin-binding conjugates include
(a) a lipid component;
(b) an optional polar component; and
(c) an immunomodulatory compound or molecular adjuvant;

wherein the immunomodulatory compound or molecular adjuvant is bound directly to the lipid or is bound to the lipid via a linker, wherein the conjugate is sufficiently soluble such that the lipid binds to albumin under physiological conditions, and wherein a plurality of the conjugates can spontaneously form micelles in aqueous solution.

Lipid conjugates including lipid-oligonucleotide conjugates and lipid-peptide conjugates and their use for stimulating immune response are disclosed. For example, amphiphilic oligonucleotide conjugates for targeting the lymph nodes can include an immunostimulatory oligonucleotide which (i) is conjugated directly to a lipid, or (ii) is linked to a linker which is conjugated to a lipid. Typically, the lipid binds to albumin under physiological conditions. In some embodiments, a plurality of the oligonucleotide conjugates can spontaneously form micelles in aqueous solution which can be disrupted by the addition of an albumin containing agent. In a specific embodiment, 64% or more of the micelles are disrupted in the presence of 20% fetal bovine serum.

In some embodiments for targeting the lymph nodes, the oligonucleotide includes an oligonucleotide linker including 0, 1, or 2 consecutive guanines. For example, the conjugate can have the structure L-5'-$G_n$-ON-3', wherein "L" the lipid, "G" is a guanine, "n" is 0-2, and "ON" is the immunostimulatory oligonucleotide.

The lipid of the conjugate typically binds to albumin. An exemplary lipid is a diacyl lipid, such a diacyl lipid wherein the chains include C12 or more hydrocarbon units.

The immunostimulatory oligonucleotide can be a ligand for a pattern recognition receptor such as CpG, and have a modified backbone such as a phosphorothioate (PS) backbone. In some embodiments, the oligonucleotide includes 20 or more nucleic acids.

Conjugates for retention at sites at or near the site of administration are also disclosed. Referred to as micelle-stabilizing conjugates, the cargo and the lipid are typically linked by an oligonucleotide linker including at least three consecutive guanines. Typically the conjugates spontaneously form micelles in aqueous solution that are resistant to disruption by albumin. In a particular embodiment, more than 36% of the micelles are intact in the presence of 20% fetal bovine serum. In some embodiments, the oligonucleotide conjugate has the structure L-5'-$G_n$-ON-3', wherein "L" the lipid, "G" is a guanine, "n" is 3-10, and "ON" is the immunostimulatory oligonucleotide.

Lipid-peptide conjugates are also disclosed. Typically the conjugate includes a peptide antigen which (i) is conjugated directly to a lipid, or (ii) is linked to a linker which is conjugated to a lipid. The lipid typically binds to albumin under physiological conditions. In some embodiments, the peptide antigen, the linker, or the peptide antigen and linker in combination are sufficiently polar to reduced or inhibit insertion of the lipid into a cell's plasma membrane.

Immunogenic compositions including lipid-oligonucleotide conjugates, lipid-peptide conjugates, and combinations thereof are also disclosed. The immunogenic compositions can be used to increase an immune response in a subject. Typically, the subject is administered an effective amount of the immunogenic composition to increase an effector immune cell response, for example, increase the number of CD8+ T cell expressing TNF-α or INF-γ compared to a control. The methods can be used to treat subjects with cancer or infectious diseases.

BRIEF DESCRIPTION OF THE DRAWINGS

FIG. 1A is a schematic illustrating three domains of a lipid conjugate: cargo conjugated to a polar block which promotes solublization conjugated to a lipophilic tail. FIG. 1B is a schematic illustrating an exemplary lipid-oligonucleotide conjugate including an immunostimulatory oligonucleotide (CpG) cargo conjugated to a lipophilic tail.

FIG. 2G is a bar graph showing the quantification of cell insertion of amphiphiles with different PEG length.

FIG. 2D is a bar graph showing the percentage of B220+ cells, F4/80+ cells, and CD11c+ cells that were CpG positive as determined by flow cytometry. *, $p<0.001$; , $p<0.01$; *, $p<0.05$.

DETAILED DESCRIPTION OF THE INVENTION

I. Definitions

Figure 1C:
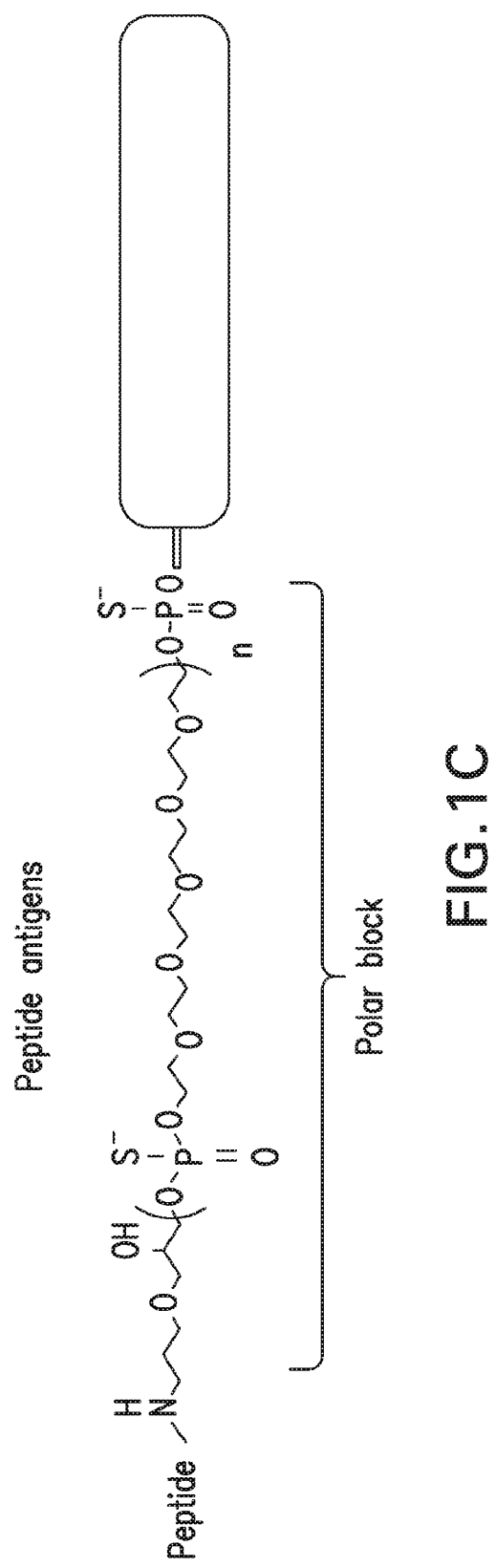
FIG. 1C is a schematic illustrating an exemplary lipid-peptide conjugate including an antigenic peptide cargo conjugated to polar block which is conjugated to a lipophilic tail.
Figures 1D, 1E:
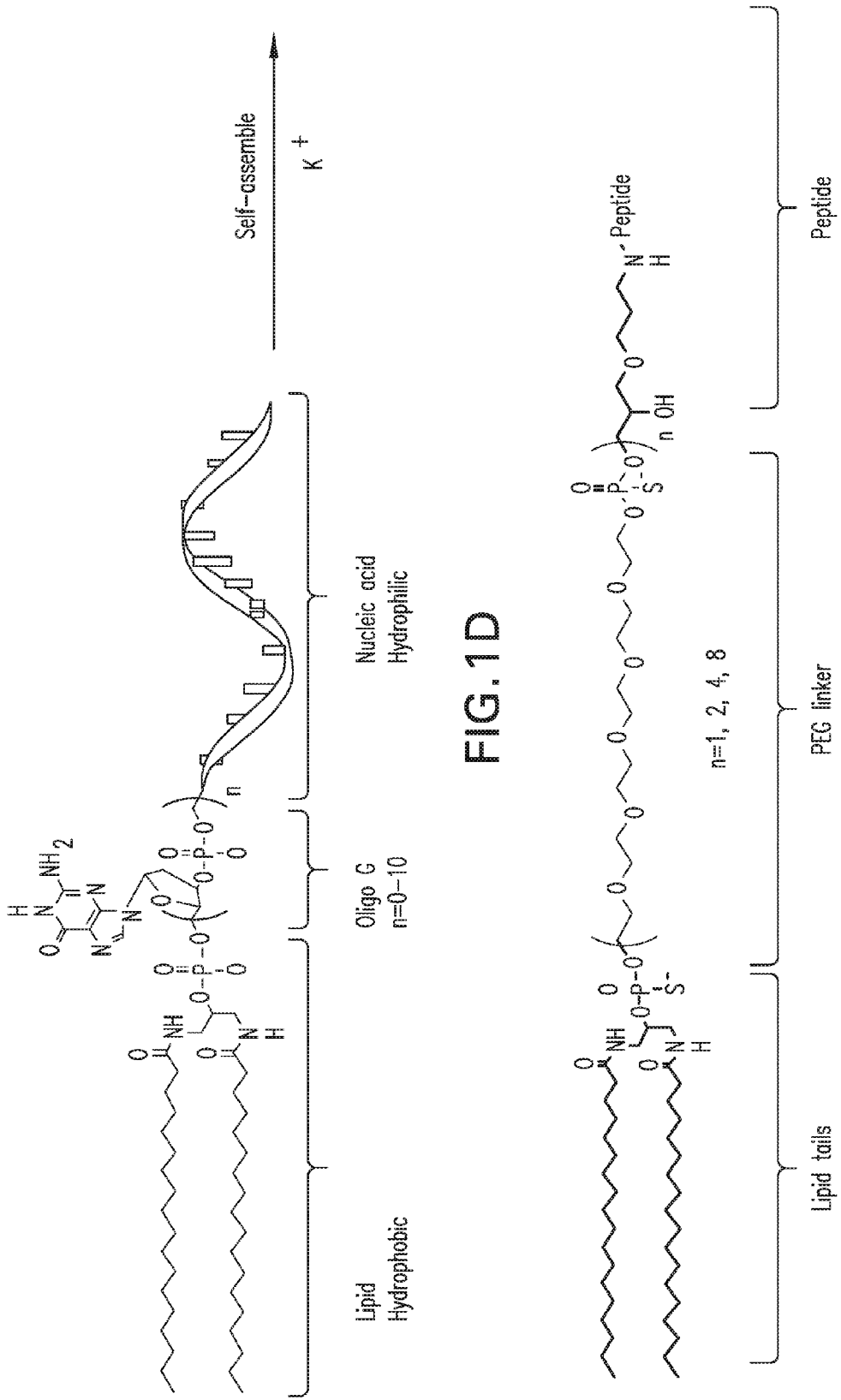
FIG. 1D is an exemplary lipid-oligonucleotide conjugate including a diacyl lipid tail conjugated to an oligo-guanine linker which is conjugated to an oligonucleotide cargo.
FIG. 1E is an exemplary lipid-peptide conjugate including a diacyl lipid tail conjugated to polyethylene glycol (PEG) linker which is conjugated to a peptide cargo.

An immunostimulatory oligonucleotide, as used herein, is an oligonucleotide that can stimulate (e.g., induce or enhance) an immune response.

As used herein, CG oligodeoxynucleotides (CG ODNs) are short single-stranded synthetic DNA molecules that contain a cytosine nucleotide (C) followed by a guanine nucleotide (G).

By "immune cell" is meant a cell of hematopoietic origin and that plays a role in the immune response. Immune cells include lymphocytes (e.g., B cells and T cells), natural killer cells, and myeloid cells (e.g., monocytes, macrophages, eosinophils, mast cells, basophils, and granulocytes).

The term 'T cell" refers to a CD4+ T cell or a CD8+ T cell. The term T cell includes TH1 cells, TH2 cells and TH17 cells.

The term "T cell cytotoxicity" includes any immune response that is mediated by CD8+ T cell activation. Exemplary immune responses include cytokine production, CD8+ T cell proliferation, granzyme or perforin production, and clearance of an infectious agent.

As generally used herein "pharmaceutically acceptable" refers to those compounds, materials, compositions, and/or dosage forms which are, within the scope of sound medical judgment, suitable for use in contact with the tissues, organs, and/or bodily fluids of human beings and animals without excessive toxicity, irritation, allergic response, or other problems or complications commensurate with a reasonable benefit/risk ratio.

The terms "individual, "subject," and "patient" refer to any individual who is the target of treatment using the disclosed compositions. The subject can be a vertebrate, for example, a mammal. Thus, the subject can be a human. The subjects can be symptomatic or asymptomatic. The term does not denote a particular age or sex. Thus, adult and newborn subjects, whether male or female, are intended to be covered. A subject can include a control subject or a test subject.

As used herein, the term "polypeptide" refers to a chain of amino acids of any length, regardless of modification (e.g., phosphorylation or glycosylation).

The term "effective amount" or "therapeutically effective amount" means a dosage sufficient to provide treatment for a disorder, disease, or condition being treated, to induce or enhance an immune response, or to otherwise provide a desired pharmacologic and/or physiologic effect. The precise dosage will vary according to a variety of factors such as subject-dependent variables (e.g., age, immune system health, etc.), the disease, the disease stage, and the treatment being effected.

The terms "individual," "individual," "subject," and "patient" are used interchangeably herein, and refer to a mammal, including, but not limited to, humans, rodents, such as mice and rats, and other laboratory animals.

The terms "oligonucleotide" or a "polynucleotide" are synthetic or isolated nucleic acid polymers including a plurality of nucleotide subunits.

II. Compositions

The structural features of a lipid conjugate that control targeting of the conjugate to the lymph nodes have been discovered. Under physiological conditions, amphiphilic lipid conjugates exist in a 3-way equilibrium depicted in FIG. 2F. In pure water certain lipid conjugates form micelles, but in the presence of serum and cells these amphiphiles equilibrate between binding to albumin and insertion of their lipophilic tails into cell membranes.

As discussed in more detail below, lipid conjugates that effectively target the lymph nodes typically include three domains: a lipophilic domain that binds to albumin, a polar block domain, and a cargo such as a molecular adjuvant or immunostimulatory compound (such as oligonucleotide) or antigenic peptide. Depending on the cargo, the length and compositions of the polar block can be tailored to push the equilibrium toward albumin binding, stable micelle formation, or cell insertion. The design guidelines and compositions disclosed below can be used to induce or enhance robust immune responses with low systemic toxicity because the immunostimulating compounds are localized to the lymph node (i.e., lymph node-targeting conjugates) or the tissue at the local site of administration (i.e., micelle-stabilizing conjugate).

The effectiveness of any particular lipid conjugate to target the lymph nodes can be assayed based on the ability of albumin to disrupt micelles formed by a plurality of the conjugates in aqueous solution. For example, if an albumin containing agent such fetal bovine serum can disrupt 20, 25, 30, 35, 40, 45, 50, 55, 60, 65, 70, 75 percent or more of the micelles formed in aqueous solution, the conjugate can be selected to target the lymph nodes. However, if 25, 30, 35, 40, 45, 50, 55, 60, 65, 70, 75 percent or more of the micelles formed in aqueous solution remain intact in the presence of albumin, the conjugate can be selected as a micelle-stabilizing conjugate.

A. Lymph Node-Targeted Conjugates

Lipid conjugates such as lipid-oligonucleotide and lipid-peptide conjugates for use in immunogenic compositions are disclosed. Lymph node-targeting conjugates can be trafficked from the site of administration through the lymph to the lymph node where they accumulate and activate immune cells. It is believed that efficient lymph node accumulation of lipid conjugates dependents on the ability of the amphiphile to partition from micelles into a serum protein-bound state.

Lymph node-targeting conjugates typically include three domains: a highly lipophilic, albumin-binding domain (e.g., an albumin-binding lipid), a cargo such as a molecular adjuvant or a peptide antigen, and a polar block linker, which promotes solubility of the conjugate and reduces the ability of the lipid to insert into cellular plasma membranes. Accordingly, in some embodiments, the general structure of the conjugate is L-P-C, where "L" is an albumin-binding lipid, "P" is a polar block, and "C" is a cargo such as a molecular adjuvant or a polypeptide. In some embodiments, the cargo itself can also serve as the polar block domain, and a separate polar block domain is not required. Therefore, in some embodiments the conjugate is only two domains: an albumin-binding lipid and a cargo. For example, lipid-oligonucleotide conjugates can include an immunostimulatory oligonucleotide which is conjugated directly to a lipid, or is linked to a linker which is conjugated to a lipid. Lipid-peptide conjugates can include an antigenic peptide which is conjugated directly to a lipid, or is linked to a linker which is conjugated to a lipid.

Lipid-conjugated peptides are well known (lipopeptides) as vaccine agents, but in our hands lipid conjugated directly to peptide does NOT exhibit lymph node targeting, because the conjugates are not soluble enough to partition preferentially onto albumin in the presence of cells; they instead insert heavily into cell membranes and thus remain trapped at an injection site.

Antigenic peptides directly conjugated to lipids (lipopeptides) have been extensively studied as a modality for enhancing vaccine efficacy (Jackson, et al in *New Generation Vaccines* (2011); Eriksson & Jackson *Curr Protein Pept Sci* 8, 412-417 (2007); BenMohamed, et al. *The Lancet Infectious Diseases* 2, 425-431 (2002)). These molecules do not generally exhibit lymph node targeting. This is illustrated by the data in FIGS. 2G and H, where it is shown that a very short PEG linker attached to an albumin-binding diacyl tail leads to strong cell membrane insertion in vitro (2G) and fails to accumulate to a significant degree in lymph nodes in vivo following subcutaneous injection (2H). Further, peptide antigens linked directly to albumin-binding diacyl tails elicit barely detectable immune responses in vivo while lipo-PEG-peptides elicit robust T-cell responses (FIG. 5C. A second distinction from previously reported lipopeptides is that the diacyl tails promoting lipid binding and lymph node targeting here show no direct adjuvant activity on their own, unlike lipopeptides such as pam3cys-peptide conjugates, that are known to have adjuvant activity through binding to TLR-2 and other immunostimulatory receptors.

1. Lipids

The lipid conjugates disclosed herein typically include a hydrophobic lipid. The lipid can be linear, branched, or cyclic. The lipid is preferably at least 17 to 18 carbons in length, but may be shorter if it shows good albumin binding and adequate targeting to the lymph nodes.

Lymph node-targeting conjugates include lipid-oligonucleotide conjugates and lipid-peptide conjugates that can be trafficked from the site of delivery through the lymph to the lymph node. In preferred embodiments, the activity relies, in-part, on the ability of the conjugate to associate with albumin in the blood of the subject. Therefore, lymph node-targeted conjugates typically include a lipid that can bind to albumin under physiological conditions. Lipids suitable for targeting the lymph node can be selected based on the ability of the lipid or a lipid conjugate including the lipid to bind to albumin. Suitable methods for testing the ability of the lipid or lipid conjugate to bind to albumin are known in the art and discussed in the Examples below.

Figure 2A:
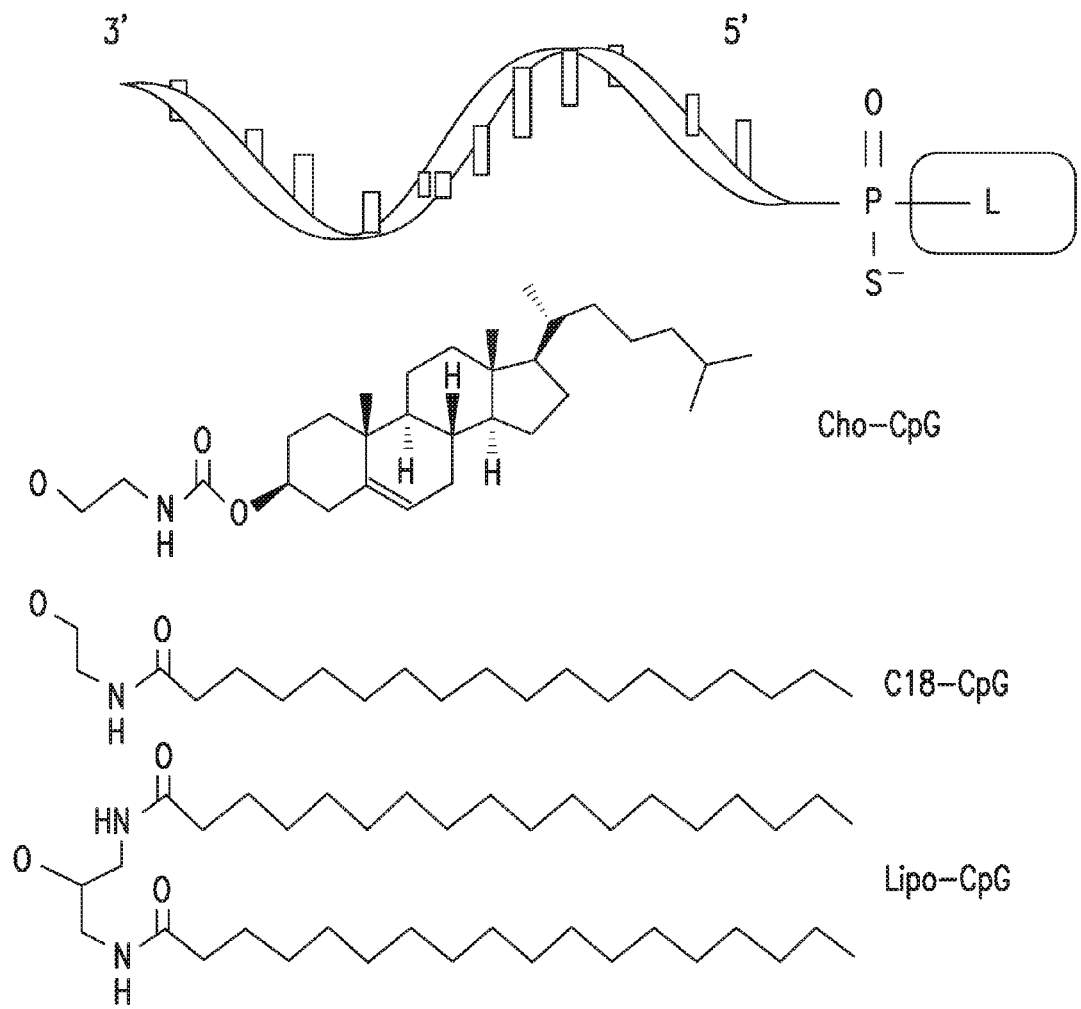
FIG. 2A is a schematic showing the design of exemplary lymph node targeting amphiphiles: the hydrophobic lipid-like tail (L) is conjugated to the 5'-end of the CpG ODN, CpG sequence has fully phosphorothioated backbone. Three alternative lipids: cholesterol, acyl (C18), and diacyl (C18) are depicted.
Figure 2B:
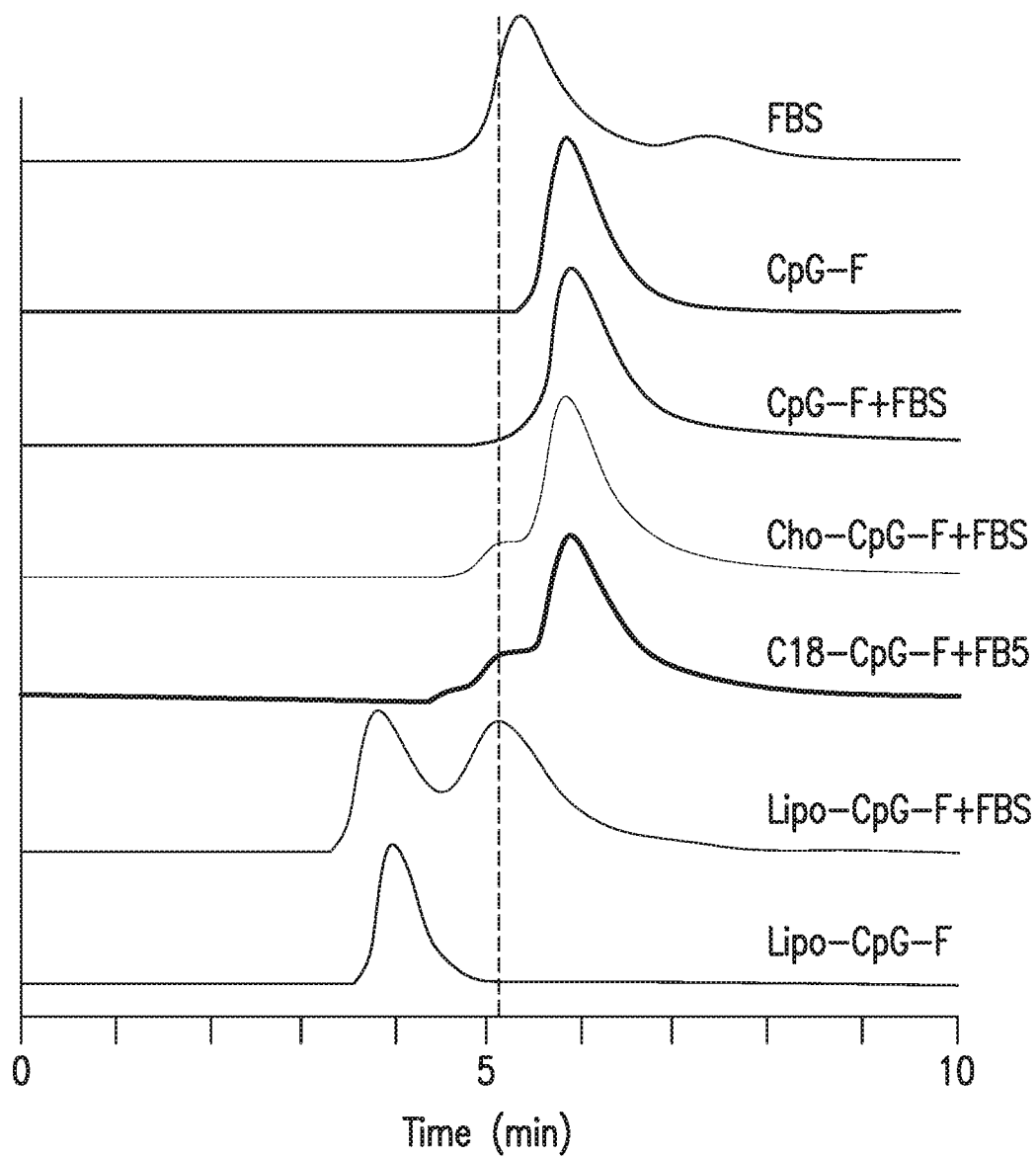
FIG. 2B is a line graph showing the results of size exclusion HPLC fluorescein-labeled lipid-conjugated CpGs after incubation with fetal bovine serum (FBS) for 2 hours at 37° C.

For example, in one embodiment, a plurality of lipid conjugates is allowed to spontaneously form micelles in aqueous solution. The micelles are incubated with albumin, or a solution including albumin such Fetal Bovine Serum (FBS). Samples can be analyzed, for example, by ELISA, size exclusion chromatography or other methods to determine if binding has occurred, as illustrated in FIG. 2B. Lipid conjugates can be selected as lymph node-targeting conjugates if in the presence of albumin, or a solution including albumin such Fetal Bovine Serum (FBS), the micelles dissociate and the lipid conjugates bind to albumin as discussed above.

Examples of preferred lipids for use in lymph node targeting lipid conjugates include, but are not limited to fatty acids with aliphatic tails of 8-30 carbons including, but not limited to, linear and unsaturatedsaturated fatty acids, branched saturated and unsaturated fatty acids, and fatty acids derivatives, such as fatty acid esters, fatty acid amides, and fatty acid thioesters, diacyl lipids, Cholesterol, Cholesterol derivatives, and steroid acids such as bile acids; Lipid A or combinations thereof.

In some embodiments, the lipid is a diacyl lipid or two-tailed lipid. In some embodiments, the tails in the diacyl lipid contain from about 8 to about 30 carbons and can be saturated, unsaturated, or combinations thereof. The tails can be coupled to the head group via ester bond linkages, amide bond linkages, thioester bond linkages, or combinations thereof. In a particular embodiment, the diacyl lipids are phosphate lipids, glycolipids, sphingolipids, or combinations thereof.

Preferably, lymph node-targeting conjugates include a lipid that is 8 or more carbon units in length. It is believed that increasing the number of lipid units can reduce insertion of the lipid into plasma membrane of cells, allowing the lipid conjugate to remain free to bind albumin and traffic to the lymph node.

For example, the lipid can be a diacyl lipid composed of two C18 hydrocarbon tails.

Figure 2C:
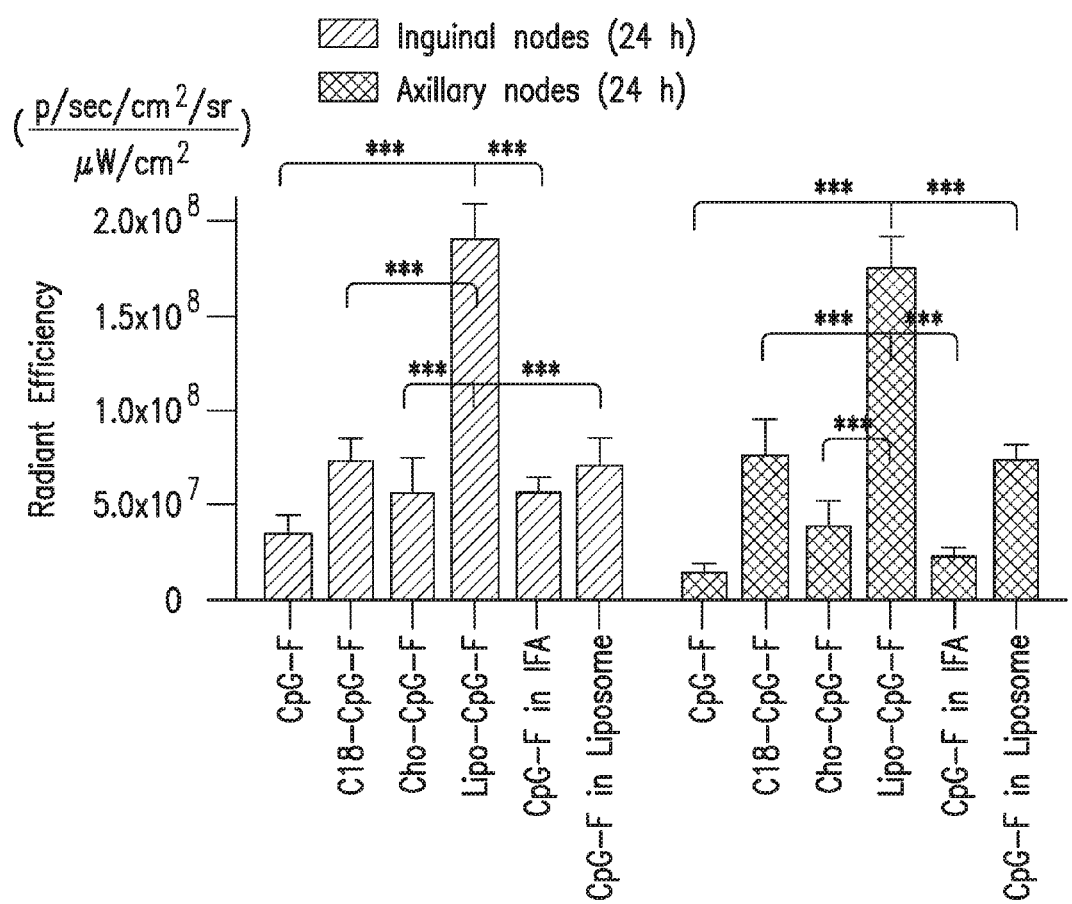
FIG. 2C is two bar graphs showing in vivo LN (inguinal nodes in the left graph, and auxiliary nodes in the right graph) accumulation of CpGs in different fluorescein-labeled formulations (CpG-F, C18-CpG-F, Cho-CpG-F, Lipo-CpG-F, CpG-F in IFA, CpG-F in liposome) 24 hours after subcutaneous injection of 3.3 nmol fluorescein labeled CpGs.
Figure 2D:
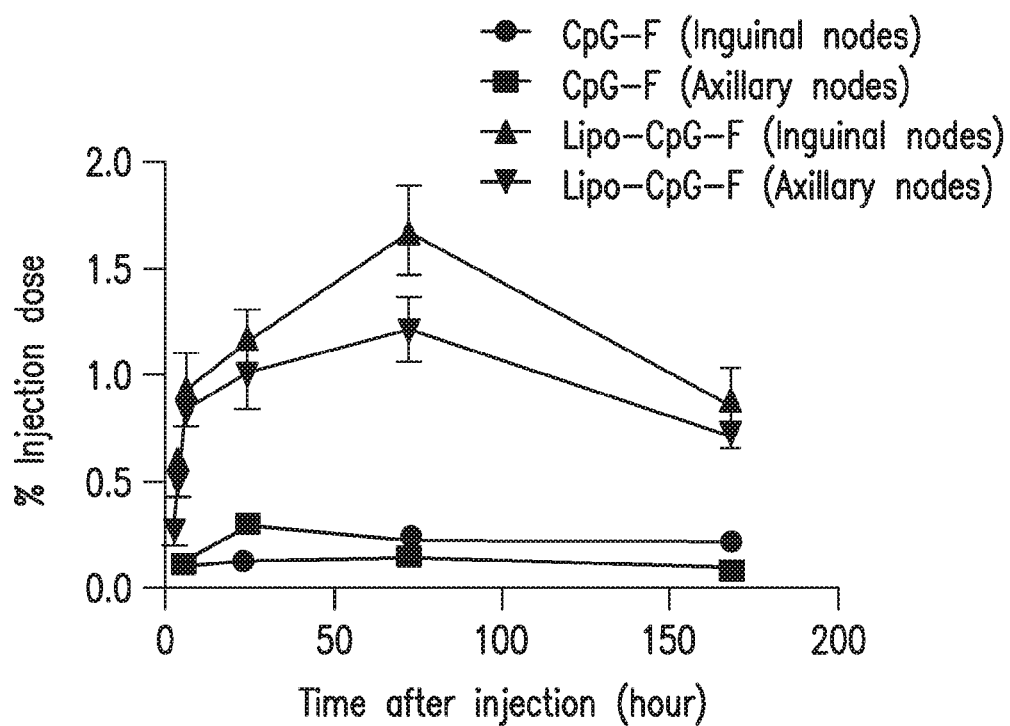
FIG. 2D is line graph showing the kinetics of CpG fluorescence (normalized to the injection dose) in LNs after injection with CpG-F (inguinal nodes (-●-) and auxiliary nodes (-■-)) or Lipo-CpG-F (inguinal nodes (-▲-) and auxiliary nodes (-▼-)).
Figure 2E:
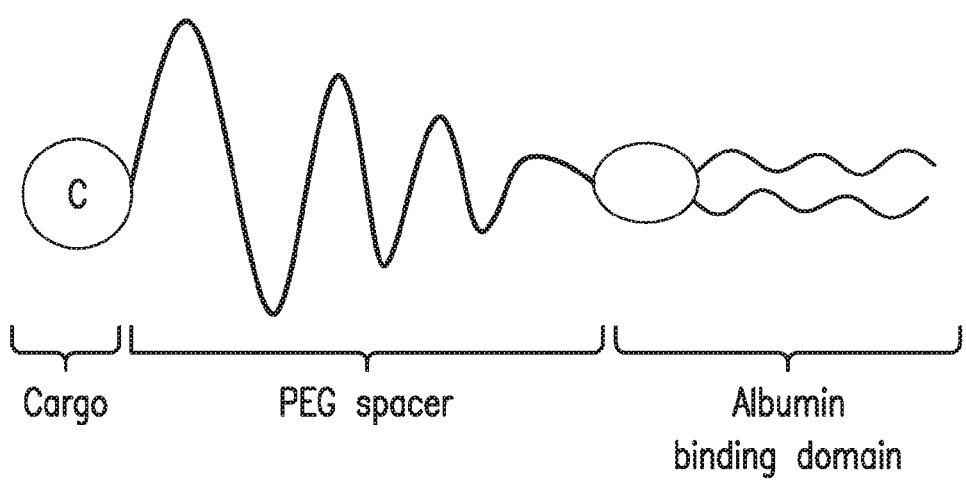
FIG. 2E is a schematic showing a generalized design of a lymph node targeting amphiphile containing an albumin binding domain, a polar spacer and a cargo linked at the end of the spacer.

In some embodiments, the lipid for use in preparing lymph node targeting lipid conjugates is not a single chain hydrocarbon (e.g., C18), or cholesterol. Cholesterol conjugation has been explored to enhance the immunomodulation of molecular adjuvants such as CpG and immunogenicity of peptides, but cholesterol conjugates, which associates well with lipoproteins but poorly with albumin, show poor lymph node targeting and low immunogenicity in vaccines compared to optimal albumin-binding conjugates (FIG. 2C).

2. Cargo

The cargo of the conjugates disclosed herein is a typically a molecular adjuvant such as an immunostimulatory oligonucleotide, or a peptide antigen. However, the cargo can also be other oligonucleotides, peptides, Toll-like receptor agonists or other immunomodulatory compounds, dyes, MRI contrast agents, fluorophores or small molecule drugs that require efficient trafficking to the lymph nodes.

a. Molecular Adjuvants

Lipid-oligonucleotide conjugates are disclosed. The oligonucleotide conjugates described herein typically contain an immunostimulatory oligonucleotide.

In some embodiments, the immunostimulatory oligonucleotide can serve as a ligand for pattern recognition receptors (PRRs). Examples of PRRs include the Toll-like family of signaling molecules that play a role in the initiation of innate immune responses and also influence the later and more antigen specific adaptive immune responses. Therefore, the oligonucleotide can serve as a ligand for a Toll-like family signaling molecule, such as Toll-Like Receptor 9 (TLR9).

For example, unmethylated CpG sites can be detected by TLR9 on plasmacytoid dendritic cells and B cells in humans (Zaida, et al., *Infection and Immunity*, 76(5):2123-2129, (2008)). Therefore, the sequence of oligonucleotide can include one or more unmethylated cytosine-guanine (CG or CpG, used interchangeably) dinucleotide motifs. The 'p' refers to the phosphodiester backbone of DNA, as discussed in more detail below, some oligonucleotides including CG can have a modified backbone, for example a phosphorothioate (PS) backbone.

In some embodiments, an immunostimulatory oligonucleotide can contain more than one CG dinucleotide, arranged either contiguously or separated by intervening nucleotide(s). The CpG motif(s) can be in the interior of the oligonucleotide sequence. Numerous nucleotide sequences stimulate TLR9 with variations in the number and location of CG dinucleotide(s), as well as the precise base sequences flanking the CG dimers.

Typically, CG ODNs are classified based on their sequence, secondary structures, and effect on human peripheral blood mononuclear cells (PBMCs). The five classes are Class A (Type D), Class B (Type K), Class C, Class P, and Class S (Vollmer, J & Krieg, A M, *Advanced drug delivery reviews* 61(3): 195-204 (2009), incorporated herein by reference). CG ODNs can stimulate the production of Type I interferons (e.g., IFNα) and induce the maturation of dendritic cells (DCs). Some classes of ODNs are also strong activators of natural killer (NK) cells through indirect cytokine signaling. Some classes are strong stimulators of human B cell and monocyte maturation (Weiner, G L, PNAS USA 94(20): 10833-7 (1997); Dalpke, A H, Immunology 106(1): 102-12 (2002); Hartmann, G, J of Immun. 164(3): 1617-2 (2000), each of which is incorporated herein by reference).

Other PRR Toll-like receptors include TLR3, and TLR7 which may recognize double-stranded RNA, single-stranded and short double-stranded RNAs, respectively, and retinoic acid-inducible gene I (RIG-I)-like receptors, namely RIG-I and melanoma differentiation-associated gene 5 (MDA5), which are best known as RNA-sensing receptors in the cytosol. Therefore, in some embodiments, the oligonucleotide contains a functional ligand for TLR3, TLR7, or RIG-I-like receptors, or combinations thereof.

Examples of immunostimulatory oligonucleotides, and methods of making them are known in the art, see for example, Bodera, P. *Recent Pat Inflamm Allergy Drug Discov.* 5(1):87-93 (2011), incorporated herein by reference.

In some embodiments, the oligonucleotide cargo includes two or more immunostimulatory sequences.

The oligonucleotide can be between 2-100 nucleotide bases in length, including for example, 5 nucleotide bases in length, 10 nucleotide bases in length, 15 nucleotide bases in length, 20 nucleotide bases in length, 25 nucleotide bases in length, 30 nucleotide bases in length, 35 nucleotide bases in length, 40 nucleotide bases in length, 45 nucleotide bases in length, 50 nucleotide bases in length, 60 nucleotide bases in length, 70 nucleotide bases in length, 80 nucleotide bases in length, 90 nucleotide bases in length, 95 nucleotide bases in length, 98 nucleotide bases in length, 100 nucleotide bases in length or more.

The 3' end or the 5' end of the oligonucleotides can be conjugated to the polar block or the lipid. In a preferred embodiment the 5' end of the oligonucleotide is linked to the polar block or the lipid.

The oligonucleotides can be DNA or RNA nucleotides which typically include a heterocyclic base (nucleic acid base), a sugar moiety attached to the heterocyclic base, and a phosphate moiety which esterifies a hydroxyl function of the sugar moiety. The principal naturally-occurring nucleotides comprise uracil, thymine, cytosine, adenine and guanine as the heterocyclic bases, and ribose or deoxyribose sugar linked by phosphodiester bonds.

In some embodiments, the oligonucleotides are composed of nucleotide analogs that have been chemically modified to improve stability, half-life, or specificity or affinity for a target receptor, relative to a DNA or RNA counterpart. The chemical modifications include chemical modification of nucleobases, sugar moieties, nucleotide linkages, or combinations thereof. As used herein 'modified nucleotide" or "chemically modified nucleotide" defines a nucleotide that has a chemical modification of one or more of the heterocyclic base, sugar moiety or phosphate moiety constituents. In some embodiments, the charge of the modified nucleotide is reduced compared to DNA or RNA oligonucleotides of the same nucleobase sequence. For example, the oligonucleotide can have low negative charge, no charge, or positive charge.

Typically, nucleoside analogs support bases capable of hydrogen bonding by Watson-Crick base pairing to standard polynucleotide bases, where the analog backbone presents the bases in a manner to permit such hydrogen bonding in a sequence-specific fashion between the oligonucleotide analog molecule and bases in a standard polynucleotide (e.g., single-stranded RNA or single-stranded DNA). In some embodiments, the analogs have a substantially uncharged, phosphorus containing backbone.

i. Heterocyclic Bases

The principal naturally-occurring nucleotides include uracil, thymine, cytosine, adenine and guanine as the heterocyclic bases. The oligonucleotides can include chemical modifications to their nucleobase constituents. Chemical modifications of heterocyclic bases or heterocyclic base analogs may be effective to increase the binding affinity or stability in binding a target sequence. Chemically-modified heterocyclic bases include, but are not limited to, inosine, 5-(1-propynyl) uracil (pU), 5-(1-propynyl) cytosine (pC), 5-methylcytosine, 8-oxo-adenine, pseudocytosine, pseudoisocytosine, 5 and 2-amino-5-(2'-deoxy-.beta.-D-ribofuranosyl)pyridine (2-aminopyridine), and various pyrrolo- and pyrazolopyrimidine derivatives. Cyclic dinucleotides known to trigger cytosolic danger sensors such as STING could be used.

ii. Sugar Modifications

Oligonucleotides can also contain nucleotides with modified sugar moieties or sugar moiety analogs. Sugar moiety modifications include, but are not limited to, 2'-O-aminoetoxy, 2'-O-amonioethyl (2'-OAE), 2'-O-methoxy, 2'-O-methyl, 2-guanidoethyl (2'-OGE), 2'-0,4'-C-methylene (LNA), 2'-O-(methoxyethyl) (2'-OME) and 2'-O—(N-(methyl)acetamido) (2'-OMA). 2'-O-aminoethyl sugar moiety substitutions are especially preferred because they are protonated at neutral pH and thus suppress the charge repulsion between the TFO and the target duplex. This modification stabilizes the C3'-endo conformation of the ribose or dexyribose and also forms a bridge with the i-1 phosphate in the purine strand of the duplex.

In some embodiments, the oligonucleotide is a morpholino oligonucleotide. Morpholino oligonucleotides are typically composed of two more morpholino monomers containing purine or pyrimidine base-pairing moieties effective to bind, by base-specific hydrogen bonding, to a base in a polynucleotide, which are linked together by phosphorus-containing linkages, one to three atoms long, joining the morpholino nitrogen of one monomer to the 5' exocyclic carbon of an adjacent monomer. The purine or pyrimidine base-pairing moiety is typically adenine, cytosine, guanine, uracil or thymine. The synthesis, structures, and binding characteristics of morpholino oligomers are detailed in U.S. Pat. Nos. 5,698,685, 5,217,866, 5,142,047, 5,034,506, 5,166,315, 5,521,063, and 5,506,337.

Important properties of the morpholino-based subunits typically include: the ability to be linked in a oligomeric form by stable, uncharged backbone linkages; the ability to support a nucleotide base (e.g. adenine, cytosine, guanine, thymidine, uracil or inosine) such that the polymer formed can hybridize with a complementary-base target nucleic acid, including target RNA, with high $T_m$, even with oligomers as short as 10-14 bases; the ability of the oligomer to be actively transported into mammalian cells; and the ability of an oligomer:RNA heteroduplex to resist RNAse degradation.

In some embodiments, oligonucleotides employ morpholino-based subunits bearing base-pairing moieties, joined by uncharged linkages, as described above.

iii. Internucleotide Linkages

Oligonucleotides connected by an internucleotide bond that refers to a chemical linkage between two nucleoside moieties. Modifications to the phosphate backbone of DNA or RNA oligonucleotides may increase the binding affinity or stability oligonucleotides, or reduce the suseptability of oligonucleotides nuclease digestion. Cationic modifications, including, but not limited to, diethyl-ethylenediamide (DEED) or dimethyl-aminopropylamine (DMAP) may be especially useful due to decrease electrostatic repulsion between the oligonucleotide and a target. Modifications of the phosphate backbone may also include the substitution of a sulfur atom for one of the non-bridging oxygens in the phosphodiester linkage. This substitution creates a phosphorothioate internucleotide linkage in place of the phosphodiester linkage. Oligonucleotides containing phosphorothioate internucleotide linkages have been shown to be more stable in vivo.

Examples of modified nucleotides with reduced charge include modified internucleotide linkages such as phosphate analogs having achiral and uncharged intersubunit linkages (e.g., Sterchak, E. P. et al., Organic Chem., 52:4202, (1987)), and uncharged morpholino-based polymers having achiral intersubunit linkages (see, e.g., U.S. Pat. No. 5,034,506), as discussed above. Some internucleotide linkage analogs include morpholidate, acetal, and polyamide-linked heterocycles.

In another embodiment, the oligonucleotides are composed of locked nucleic acids. Locked nucleic acids (LNA) are modified RNA nucleotides (see, for example, Braasch, et al., Chem. Biol., 8(1):1-7 (2001)). LNAs form hybrids with DNA which are more stable than DNA/DNA hybrids, a property similar to that of peptide nucleic acid (PNA)/DNA hybrids. Therefore, LNA can be used just as PNA molecules would be. LNA binding efficiency can be increased in some embodiments by adding positive charges to it. Commercial nucleic acid synthesizers and standard phosphoramidite chemistry are used to make LNAs.

In some embodiments, the oligonucleotides are composed of peptide nucleic acids. Peptide nucleic acids (PNAs) are synthetic DNA mimics in which the phosphate backbone of the oligonucleotide is replaced in its entirety by repeating N-(2-aminoethyl)-glycine units and phosphodiester bonds are typically replaced by peptide bonds. The various heterocyclic bases are linked to the backbone by methylene carbonyl bonds. PNAs maintain spacing of heterocyclic bases that is similar to conventional DNA oligonucleotides, but are achiral and neutrally charged molecules. Peptide nucleic acids are comprised of peptide nucleic acid monomers.

Other backbone modifications include peptide and amino acid variations and modifications. Thus, the backbone constituents of oligonucleotides such as PNA may be peptide linkages, or alternatively, they may be non-peptide peptide linkages. Examples include acetyl caps, amino spacers such as 8-amino-3,6-dioxaoctanoic acid (referred to herein as O-linkers), amino acids such as lysine are particularly useful if positive charges are desired in the PNA, and the like. Methods for the chemical assembly of PNAs are well known. See, for example, U.S. Pat. Nos. 5,539,082, 5,527,675, 5,623,049, 5,714,331, 5,736,336, 5,773,571 and 5,786,571.

Oligonucleotides optionally include one or more terminal residues or modifications at either or both termini to increase stability, and/or affinity of the oligonucleotide for its target. Commonly used positively charged moieties include the amino acids lysine and arginine, although other positively charged moieties may also be useful. Oligonucleotides may further be modified to be end capped to prevent degradation using a propylamine group. Procedures for 3' or 5' capping oligonucleotides are well known in the art.

In some embodiments, the oligonucleotide is single-stranded DNA, single-stranded RNA, or double-stranded RNA.

b. Peptide Antigens

Lipid-peptide conjugates are disclosed. The peptide conjugates described herein typically include an antigenic protein or polypeptide.

The peptide can be 2-100 amino acids (aa), including for example, 5 amino acids, 10 amino acids, 15 amino acids, 20 amino acids, 25 amino acids, 30 amino acids, 35 amino acids, 40 amino acids, 45 amino acids, or 50 amino acids. In some embodiments, a peptide can be greater than 50 amino acids. In some embodiments, the peptide can be >100 amino acids.

A protein/peptide can be linear, branched or cyclic. The peptide can include D amino acids, L amino acids, or a combination thereof. The peptide or protein can be conjugated to the polar block or lipid at the N-terminus or the C-terminus of the peptide or protein.

The protein or polypeptide can be any protein or peptide that can induce or increase the ability of the immune system to develop antibodies and T-cell responses to the protein or peptide. Examples of specific peptide and protein antigens that can be used in the lipid-peptide conjugates disclosed herein are discussed in more detail below with respect to preferred antigens that can be used in vaccine formulations.

Lipid-protein-based micelles can be formed in an aqueous solution by self-assembly of conjugates containing a peptide antigen linked (attached) to a polyethylene glycol (PEG) moiety or derivative or analog thereof, which is linked to hydrophobic lipid.

c. Other Cargos

Generally, the cargo can include therapeutic, prophylactic or diagnostic agents. For example, chemotherapy drugs are of interest for targeting tumors as albumin is known to accumulate in tumors by the EPR effect and also by fast metabolism in tumors.

In some embodiments, the lipid conjugates disclosed herein include a detection label, for example, a fluorophore such as fluorescein or rhodamine, Alexa Fluor dyes, DyLight Fluor dyes, Quasar and Cal Fluor dyes, cyanine dyes (Cy3, Cy5, Cy5.5, Cy7) or other fluorescent dyes. The label can be the cargo, or can be in addition to a cargo.

3. Polar Block/Linker

For the conjugate to be trafficked efficiently to the lymph node, the conjugate should remain soluble. Therefore, a polar block linker can be included between the cargo and the lipid to increase solubility of the conjugate. The polar block reduces or prevents the ability of the lipid to insert into the plasma membrane of cells, such as cells in the tissue adjacent to the injection site. The polar block can also reduce or prevent the ability of cargo, such as synthetic oligonucleotides containing a PS backbone, from non-specifically associating with extracellular matrix proteins at the site of administration. The polar block increases the solubility of the conjugate without preventing its ability to bind to albumin. It is believed that this combination of characteristics allows the conjugate to bind to albumin present in the serum or interstitial fluid, and remain in circulation until the albumin is trafficked to, and retained in a lymph node.

The length and composition of the polar block can be adjusted based on the lipid and cargo selected. For example, for oligonucleotide conjugates, the oligonucleotide itself may be polar enough to insure solubility of the conjugate, for example, oligonucleotides that are 10, 15, 20 or more nucleotides in length. Therefore, in some embodiments, no additional polar block linker is required. However, depending on the amino acid sequence, some lipidated peptides can be essentially insoluble. In these cases, it can be desirable to include a polar block that mimics the effect of a polar oligonucleotide.

A polar block can be used as part of any of lipid conjugates described herein, for example, lipid-oligonucleotide conjugates and lipid-peptide conjugates, which reduce cell membrane insertion/preferential portioning ont albumin. Suitable polar blocks include, but are not limited to, oligonucleotides such as those discussed above, a hydrophilic polymer including but not limited to poly(ethylene glycol) (MW: 500 Da to 20,000 Da), polyacrylamide (MW: 500 Da to 20,000 Da), polyacrylic acid; a string of hydrophilic amino acids such as serine, threonine, cysteine, tyrosine, asparagine, glutamine, aspartic acid, glutamic acid, lysine, arginine, histidine, or combinations thereof polysaccharides, including but not limited to, dextran (MW: 1,000 Da to 2,000,000 Da), or combinations thereof.

The hydrophobic lipid and the linker/cargo are covalently linked. The covalent bond may be a non-cleavable linkage or a cleavable linkage. The non-cleavable linkage can include an amide bond or phosphate bond, and the cleavable linkage can include a disulfide bond, acid-cleavable linkage, ester bond, anhydride bond, biodegradable bond, or enzyme-cleavable linkage.

i. Ethylene Glycol Linkers

In a preferred embodiment, the polar block is one or more ethylene glycol (EG) units, more preferably 2 or more EG units (i.e., polyethylene glycol (PEG)). For example, in some embodiments, a peptide conjugate includes a protein or peptide (e.g., peptide antigen) and a hydrophobic lipid linked by a polyethylene glycol (PEG) molecule or a derivative or analog thereof.

In some embodiments, protein conjugates described herein contain protein antigen linked to PEG which is in turn linked to a hydrophobic lipid, or lipid-Gn-ON conjugates, either covalently or via formation of protein-oligo conjugates that hybridize to oligo micelles.

The precise number of EG units depends on the lipid and the cargo, however, typically, a polar block can have between about 1 and about 100, between about 20 and about 80, between about 30 and about 70, or between about 40 and about 60 EG units. In some embodiments, the polar block has between about 45 and 55 EG, units. For example, in one preferred embodiment, the polar block has 48 EG units.

ii. Oligonucleotide Linkers

As discussed above, in some embodiments, the polar block is an oligonucleotide. The polar block liner can be have any sequence, for example, the sequence of the oligonucleotide can be a random sequence, or a sequence specifically chosen for its molecular or biochemical properties (e.g., highly polar). In some embodiments, the polar block linker includes one or more series of consecutive adenine (A), cytosine (C), guanine (G), thymine (T), uracil (U), or analog thereof. In some embodiments, the polar block linker consists of a series of consecutive adenine (A), cytosine (C), guanine (G), thymine (T), uracil (U), or analog thereof.

In one embodiment, the linker is one or more guanines, for example between 1-10 guanines. It has been discovered that altering the number of guanines between a cargo such as a CpG oligonucleotide, and a lipid tail controls micelle stability in the presence of serum proteins. Therefore, the number of guanines in the linker can be selected based on the desired affinity of the conjugate for serum proteins such as albumin. As illustrated in the Examples below, when the cargo is a CpG immunostimulatory oligonucleotide and the lipid tail is a diacyl lipid, the number of guanines affects the ability of micelles formed in aqueous solution to dissociate in the presence of serum: 20% of the non-stabilized micelles (lipo-$G_0T_{10}$-CG) were intact, while the remaining 80% were disrupted and bonded with FBS components. In the presence of guanines, the percentage of intact micelles increased from 36% (lipo-$G_2T_8$-CG) to 73% (lipo-$G_4T_6$-CG), and finally reached 90% (lipo-$G_6T_4$-CG). Increasing the number of guanines to eight (lipo-$G_8T_2$-CG) and ten (lipo-$G_{10}T_0$-CG) did not further enhance micelle stability.

Therefore, in a preferred embodiment, the linker in a lymph node-targeting conjugate can include 0, 1, or 2 guanines. As discussed in more detail below, linkers that include 3 or more consecutive guanines can be used to form micelle-stabilizing conjugates with properties that are well suited for local applications at or near the site of administration.

B. Micelle-Stabilizing Conjugates

Micelle-stabilizing conjugates include conjugates such as lipid-oligonucleotide conjugates and lipid-peptide conjugates that accumulate in the tissue surrounding the site of delivery. The conjugates typically do not bind to albumin. In some embodiments, the lipid used to prepare a micelle-stabilizing lipid conjugate is the same as the lipid used in the lymph node targeting lipid conjugates discussed above, and the ability to resist binding to albumin is controlled by the molecular or biochemical properties of the cargo, the linker, or a combination thereof. In some embodiments, lipids that would not be effective for use in lymph node targeted conjugates are useful in micelle-stabilizing conjugates because the micelle-stabilizing conjugates do not necessarily have to bind to albumin.

Micelle-stabilizing conjugates can be selected based on the ability to spontaneously form micelles in aqueous solution that are not disrupted by serum components such as albumin, as discussed above. Suitable methods for testing the ability of the lipid or lipid conjugates to bind to albumin are known in the art and discussed in the Examples below. For example, in one embodiment, a plurality of lipid conjugates is allowed to spontaneously form micelles in aqueous solution. The micelles are incubated with albumin, or a solution including albumin such Fetal Bovine Serum (FBS). Samples can be analyzed, for example, by ELISA, size separation chromatography or other methods to determine if binding has occurred. Lipid conjugates can be selected as micelle stabilized conjugates if in the presence of albumin, or a solution including albumin such Fetal Bovine Serum (FBS), the micelles remain intact and the lipid conjugates do not bind to albumin.

Examples of preferred lipids for use in micelle-stabilizing lipid conjugates include, but are not limited to fatty acids with aliphatic tails of 8-30 carbons including, but not limited to, linear and unsaturated and saturated fatty acids, branched saturated and unsaturated fatty acids, and fatty acids derivatives, such as fatty acid esters, fatty acid amides, and fatty acid thioesters, diacyl lipids, Cholesterol, Cholesterol derivatives, and steroid acids such as bile acids; Lipid A or combinations thereof.

In some embodiments, the lipid is a diacyl lipid or two-tailed lipid In some embodiments, the tails in the diacyl lipid contain from about 8 to about 30 carbons and can be saturated, unsaturated, or combinations thereof. The tails can be coupled to the head group via ester bond linkages, amide bond linkages, thioester bond linkages, or combinations thereof. In a particular embodiment, the diacyl lipids are phosphate lipids, glycolipids, sphingolipids, or combinations thereof.

As discussed above, in some embodiments, the stability of micelles in the presence of albumin is affected by the linker. For example, an oligonucleotide, such as an immunostimulatory oligonucleotide, and the lipid can be linked by three or more intervening guanine nucleotides. The nucleotides can be positioned at the 5' end of the oligonucleotide. Guanine-rich DNA sequences can form quadruplex structures via hydrogen bonding, where the oligoguanines molecularly "glue" together four individual guanine-rich DNA sequences. Thus, the immunostimulatory oligonucleotide conjugates can self-assemble into "G-quadruplexes," which then assemble to form micelles having a hydrophobic lipid core and a nucleic acid corona. As illustrated in the Examples below, kinetic stability of a micelle can be controlled by altering the number of guanine nucleotides that link the hydrophobic lipid to the immunostimulatory oligonucleotide. In some embodiments, the immunostimulatory oligonucleotide and the hydrophobic lipid are linked by a single guanine at the 5' end of the oligonucleotide, while in other embodiments, the immunostimulatory oligonucleotide and the hydrophobic lipid are linked by two guanines at the 5' end of the oligonucleotide. In some embodiments, the intervening oligoguanine ($G_n$) contains three to ten guanines (n=3-10).

The cargo of micelle-stabilizing conjugates can includes any of the cargo discussed above with respect to lymph node targeted conjugates, as well as small molecules, oligonucleotide, or peptide therapeutics (i.e., any cargo that would one of skill in the art would select for accumulation at a site of local delivery).

Micelle-stabilizing conjugates can form micelles spontaneously in aqueous solution by self-assembly. The micelle has a hydrophobic lipid core and a hydrophilic surface. Formation of a micelle in an aqueous environment (e.g., water, buffer) is driven by hydrophobic interactions, and the micelle is stabilized by formation of the G-quadruplexes as described above. A micelle is further stabilized by the presence of a cation, such as potassium ($K^+$), in the aqueous environment. The cation connects two G-quadruplexes and minimizes the electrostatic interactions between the immunostimulatory oligonucleotides. Guanine-rich oligonucleotide sequences can fold into various types of structures (e.g., intramolecular, intermolecular, parallel, and antiparallel) (Davis, J. T. *Angew. Chem. Int. Ed. Engl.* 43, 668-698 (2004)). To facilitate micelle self-assembly and to minimize oligonucleotide folding, the lipid-oligonucleotide conjugates can be suspended in pure water to permit assembly of the micelle, and then potassium-containing buffer can be added to stabilize the G-quadruplexes.

In some embodiments, micelles of a homogeneous micelle population are substantially uniform in size. As used herein, micelles of a "homogeneous" population each are similarly composed of the same type of lipid-oligonucleotide conjugate (e.g., a L-5'-$G_n$-CG-ODN-3' conjugate).

As discussed above, the stability of the micelle can be controlled by altering the number of guanine nucleotides in the polar block. For example, in some embodiments, the conjugate includes one or more guanine nucleotides at the 5' end of the oligonucleotide and hydrophobic lipid linked to the most 5' guanine Micelle "stability" as used herein refers to resistance to disassembly or changes in micelle size in the presence of serum, albumins, or other proteins or lipids, and/or resistance of the micelles to changes in size or composition in the presence of cells.

The diameter of a micelle as described herein can be from about 3 nm to about 100 nm. In some embodiments, the diameter of a micelle is 3 nm, 4 nm, 5 nm, 6 nm, 7 nm, 8 nm, 9 nm, 10 nm, 11 nm, 12 nm, 13 nm, 14 nm, 15 nm, 16 nm, 17 nm, 18 nm, 20 nm, 21 nm, 22 nm, 23 nm, 24 nm, 25 nm, 26 nm, 27 nm, 28 nm, 29 nm, 30 nm, 31 nm, 32 nm, 33 nm, 34 nm, 35 nm, 36 nm, 37 nm, 38 nm, 39 nm, 40 nm, 41 nm, 42 nm, 43 nm, 44 nm, 45 nm, 46 nm, 47 nm, 48 nm, 49 nm, 50 nm, 51 nm, 52 nm, 53 nm, 54 nm, 55 nm, 56 nm, 57 nm, 58 nm, 59 nm, 60 nm, 61 nm, 62 nm, 63 nm, 64 nm, 65 nm, 66 nm, 67 nm, 68 nm, 69 nm, 70 nm, 71 nm, 72 nm, 73 nm, 74 nm, 75 nm, 76 nm, 77 nm, 78 nm, 79 nm, 80 nm, 81 nm, 82 nm, 83 nm, 84 nm, 85 nm, 86 nm, 87 nm, 88 nm, 89 nm, 90 nm, 91 nm, 92 nm, 93 nm, 94 nm, 95 nm, 96 nm, 97 nm, 98 nm, 99 nm, or 100 nm. In some embodiments, the diameter of a micelle is about 20 nm or about 50 nm.

III. Formulations

A. Pharmaceutical Compositions

Pharmaceutical compositions including lipid conjugates are provided. Pharmaceutical compositions can be for administration by parenteral (intramuscular, intraperitoneal, intravenous (IV) or subcutaneous injection), transdermal (either passively or using iontophoresis or electroporation), or transmucosal (nasal, vaginal, rectal, or sublingual) routes of administration or using bioerodible inserts and can be formulated in dosage forms appropriate for each route of administration.

In some embodiments, the compositions are administered systemically, for example, by intravenous or intraperitoneal administration, in an amount effective for delivery of the compositions to targeted cells. Other possible routes include trans-dermal or oral.

In certain embodiments, the compositions are administered locally, for example by injection directly into a site to be treated. In some embodiments, the compositions are injected or otherwise administered directly to one or more tumors. Typically, local injection causes an increased localized concentration of the compositions which is greater than that which can be achieved by systemic administration. In some embodiments, the compositions are delivered locally to the appropriate cells by using a catheter or syringe. Other means of delivering such compositions locally to cells include using infusion pumps (for example, from Alza Corporation, Palo Alto, Calif.) or incorporating the compositions into polymeric implants (see, for example, P. Johnson and J. G. Lloyd-Jones, eds., Drug Delivery Systems (Chichester, England: Ellis Horwood Ltd., 1987), which can effect a sustained release of the nanolipogels to the immediate area of the implant.

As further studies are conducted, information will emerge regarding appropriate dosage levels for treatment of various conditions in various patients, and the ordinary skilled worker, considering the therapeutic context, age, and general health of the recipient, will be able to ascertain proper dosing. The selected dosage depends upon the desired therapeutic effect, on the route of administration, and on the duration of the treatment desired. Generally dosage levels of 0.001 to 10 mg/kg of body weight daily are administered to mammals. Generally, for intravenous injection or infusion, dosage may be lower.

1. Formulations for Parenteral Administration

In a preferred embodiment the lipid conjugates are administered in an aqueous solution, by parenteral injection. In some embodiments, the composition includes albumin, or other serum proteins.

The formulation can be in the form of a suspension or emulsion. In general, pharmaceutical compositions are provided including an effective amount of the conjugate and optionally include pharmaceutically acceptable diluents, preservatives, solubilizers, emulsifiers, adjuvants and/or carriers. Such compositions can include diluents sterile water, buffered saline of various buffer content (e.g., Tris-HCl, acetate, phosphate), pH and ionic strength; and optionally, additives such as detergents and solubilizing agents (e.g., TWEEN® 20, TWEEN® 80 also referred to as polysorbate 20 or 80), anti-oxidants (e.g., ascorbic acid, sodium metabisulfite), and preservatives (e.g., Thimersol, benzyl alcohol) and bulking substances (e.g., lactose, mannitol). Examples of non-aqueous solvents or vehicles are propylene glycol, polyethylene glycol, vegetable oils, such as olive oil and corn oil, gelatin, and injectable organic esters such as ethyl oleate. The formulations may be lyophilized and redissolved/resuspended immediately before use. The formulation may be sterilized by, for example, filtration through a bacteria retaining filter, by incorporating sterilizing agents into the compositions, by irradiating the compositions, or by heating the compositions.

2. Formulations for Topical and Mucosal Administration

The lipid conjugates can be applied topically. Topical administration can include application to the lungs (pulmonary), nasal, oral (sublingual, buccal), vaginal, or rectal mucosa. In some cases, the conjugates may be transcytosed on albumin across mucosal barriers Compositions can be delivered to the lungs while inhaling and traverse across the lung epithelial lining to the blood stream when delivered either as an aerosol or spray dried particles having an aerodynamic diameter of less than about 5 microns.

A wide range of mechanical devices designed for pulmonary delivery of therapeutic products can be used, including but not limited to nebulizers, metered dose inhalers, and powder inhalers, all of which are familiar to those skilled in the art. Some specific examples of commercially available devices are the Ultravent® nebulizer (Mallinckrodt Inc., St. Louis, Mo.); the Acorn® II nebulizer (Marquest Medical Products, Englewood, Colo.); the Ventolin® metered dose inhaler (Glaxo Inc., Research Triangle Park, N.C.); and the Spinhaler® powder inhaler (Fisons Corp., Bedford, Mass.). Nektar, Alkermes and Mannkind all have inhalable insulin powder preparations approved or in clinical trials where the technology could be applied to the formulations described herein.

Formulations for administration to the mucosa will typically be spray dried drug particles, which may be incorporated into a tablet, gel, capsule, suspension or emulsion. Standard pharmaceutical excipients are available from any formulator. Oral formulations may be in the form of chewing gum, gel strips, tablets, capsules, or lozenges.

Transdermal formulations may also be prepared. These will typically be ointments, lotions, sprays, or patches, all of which can be prepared using standard technology. Transdermal formulations can include penetration enhancers.

B. Immunogenic Compositions

The conjugates disclosed herein can be used in immunogenic compositions or as components in vaccines. Typically, immunogenic compositions disclosed herein include an adjuvant, an antigen, or a combination thereof. The combination of an adjuvant and an antigen can be referred to as a vaccine. When administered to a subject in combination, the adjuvant and antigen can be administered in separate pharmaceutical compositions, or they can be administered together in the same pharmaceutical composition. When administered in combination, the adjuvant can be a lipid conjugate, the antigen can be a lipid conjugate, or the adjuvant and the antigen can both be lipid conjugates.

1. Antigens

An immunogenic composition can include a lipid conjugate that is an adjuvant such as an immunostimulatory oligonucleotide-lipid conjugate, administered alone, or in combination with an antigen. Antigens can be peptides, proteins, polysaccharides, saccharides, lipids, nucleic acids, or combinations thereof. The antigen can be derived from a virus, bacterium, parasite, plant, protozoan, fungus, tissue or transformed cell such as a cancer or leukemic cell and can be a whole cell or immunogenic component thereof, e.g., cell wall components or molecular components thereof.

Suitable antigens are known in the art and are available from commercial government and scientific sources. In one embodiment, the antigens are whole inactivated or attenuated organisms. These organisms may be infectious organisms, such as viruses, parasites and bacteria. These organisms may also be tumor cells. The antigens may be purified or partially purified polypeptides derived from tumors or viral or bacterial sources. The antigens can be recombinant polypeptides produced by expressing DNA encoding the polypeptide antigen in a heterologous expression system. The antigens can be DNA encoding all or part of an antigenic protein. The DNA may be in the form of vector DNA such as plasmid DNA.

Antigens may be provided as single antigens or may be provided in combination. Antigens may also be provided as complex mixtures of polypeptides or nucleic acids. Exemplary antigens are provided below.

a. Viral Antigens

A viral antigen can be isolated from any virus including, but not limited to, a virus from any of the following viral families: Arenaviridae, Arterivirus, Astroviridae, Baculoviridae, Badnavirus, Barnaviridae, Birnaviridae, Bromoviridae, Bunyaviridae, Caliciviridae, Capillovirus, Carlavirus, Caulimovirus, Circoviridae, Closterovirus, Comoviridae, Coronaviridae (e.g., Coronavirus, such as severe acute respiratory syndrome (SARS) virus), Corticoviridae, Cystoviridae, Deltavirus, Dianthovirus, Enamovirus, Filoviridae (e.g., Marburg virus and Ebola virus (e.g., Zaire, Reston, Ivory Coast, or Sudan strain)), Flaviviridae, (e.g., Hepatitis C virus, Dengue virus 1, Dengue virus 2, Dengue virus 3, and Dengue virus 4), Hepadnaviridae, Herpesviridae (e.g., Human herpesvirus 1, 3, 4, 5, and 6, and Cytomegalovirus), Hypoviridae, Iridoviridae, Leviviridae, Lipothrixviridae, Microviridae, Orthomyxoviridae (e.g., Influenzavirus A and B and C), Papovaviridae, Paramyxoviridae (e.g., measles, mumps, and human respiratory syncytial virus), Parvoviridae, Picornaviridae (e.g., poliovirus, rhinovirus, hepatovirus, and aphthovirus), Poxviridae (e.g., vaccinia and smallpox virus), Reoviridae (e.g., rotavirus), Retroviridae (e.g., lentivirus, such as human immunodeficiency virus (HIV) 1 and HIV 2), Rhabdoviridae (for example, rabies virus, measles virus, respiratory syncytial virus, etc.), Togaviridae (for example, rubella virus, dengue virus, etc.), and Totiviridae. Suitable viral antigens also include all or part of Dengue protein M, Dengue protein E, Dengue D1NS1, Dengue D1NS2, and Dengue D1NS3.

Viral antigens may be derived from a particular strain such as a papilloma virus, a herpes virus, e.g., herpes simplex 1 and 2; a hepatitis virus, for example, hepatitis A virus (HAV), hepatitis B virus (HBV), hepatitis C virus (HCV), the delta hepatitis D virus (HDV), hepatitis E virus (HEV) and hepatitis G virus (HGV), the tick-borne encephalitis viruses; parainfluenza, varicella-zoster, cytomeglavirus, Epstein-Barr, rotavirus, rhinovirus, adenovirus, coxsackieviruses, equine encephalitis, Japanese encephalitis, yellow fever, Rift Valley fever, and lymphocytic choriomeningitis.

b. Bacterial Antigens

Bacterial antigens can originate from any bacteria including, but not limited to, *Actinomyces, Anabaena, Bacillus, Bacteroides, Bdellovibrio, Bordetella, Borrelia, Campylobacter, Caulobacter, Chlamydia, Chlorobium, Chromatium, Clostridium, Corynebacterium, Cytophaga, Deinococcus, Escherichia, Francisella, Halobacterium, Heliobacter, Haemophilus, Hemophilus* influenza type B (HIB), *Hyphomicrobium, Legionella, Leptspirosis, Listeria, Meningococcus* A, B and C, *Methanobacterium, Micrococcus, Myobacterium, Mycoplasma, Myxococcus, Neisseria, Nitrobacter,*

*Oscillatoria, Prochloron, Proteus, Pseudomonas, Phodospirillum, Rickettsia, Salmonella, Shigella, Spirillum, Spirochaeta, Staphylococcus, Streptococcus, Streptomyces, Sulfolobus, Thermoplasma, Thiobacillus,* and *Treponema, Vibrio,* and *Yersinia.* c. Parasite Antigens

Parasite antigens can be obtained from parasites such as, but not limited to, an antigen derived from *Cryptococcus neoformans, Histoplasma capsulatum, Candida albicans, Candida tropicalis, Nocardia asteroides, Rickettsia ricketsii, Rickettsia typhi, Mycoplasma pneumoniae, Chlamydial psittaci, Chlamydial trachomatis, Plasmodium falciparum, Trypanosoma brucei, Entamoeba histolytica, Toxoplasma gondii, Trichomonas vaginalis* and *Schistosoma mansoni.* These include Sporozoan antigens, Plasmodian antigens, such as all or part of a Circumsporozoite protein, a Sporozoite surface protein, a liver stage antigen, an apical membrane associated protein, or a Merozoite surface protein.

d. Allergens and Environmental Antigens

The antigen can be an allergen or environmental antigen, such as, but not limited to, an antigen derived from naturally occurring allergens such as pollen allergens (tree-, herb, weed-, and grass pollen allergens), insect allergens (inhalant, saliva and venom allergens), animal hair and dandruff allergens, and food allergens. Important pollen allergens from trees, grasses and herbs originate from the taxonomic orders of Fagales, Oleales, Pinales and platanaceae including i.a. birch (*Betula*), alder (*Alnus*), hazel (*Corylus*), hornbeam (*Carpinus*) and olive (*Olea*), cedar (*Cryptomeria* and *Juniperus*), Plane tree (*Platanus*), the order of Poales including e.g., grasses of the genera *Lolium, Phleum, Poa, Cynodon, Dactylis, Holcus, Phalaris, Secale,* and Sorghum, the orders of Asterales and Urticales including i.a. herbs of the genera *Ambrosia, Artemisia,* and *Parietaria.* Other allergen antigens that may be used include allergens from house dust mites of the genus *Dermatophagoides* and *Euroglyphus,* storage mite e.g *Lepidoglyphys, Glycyphagus* and *Tyrophagus*, those from cockroaches, midges and fleas e.g. *Blatella, Periplaneta, Chironomus* and *Ctenocepphalides*, those from mammals such as cat, dog and horse, birds, venom allergens including such originating from stinging or biting insects such as those from the taxonomic order of Hymenoptera including bees (superfamily Apidae), wasps (superfamily Vespidea), and ants (superfamily Formicoidae). Still other allergen antigens that may be used include inhalation allergens from fungi such as from the genera *Alternaria* and *Cladosporium.* e. Cancer Antigens

A cancer antigen is an antigen that is typically expressed preferentially by cancer cells (i.e., it is expressed at higher levels in cancer cells than on non-cancer cells) and in some instances it is expressed solely by cancer cells. The cancer antigen may be expressed within a cancer cell or on the surface of the cancer cell. The cancer antigen can be MART-1/Melan-A, gp100, adenosine deaminase-binding protein (ADAbp), FAP, cyclophilin b, colorectal associated antigen (CRC)-0017-1A/GA733, carcinoembryonic antigen (CEA), CAP-1, CAP-2, etv6, AML1, prostate specific antigen (PSA), PSA-1, PSA-2, PSA-3, prostate-specific membrane antigen (PSMA), T cell receptor/CD3-zeta chain, and CD20. The cancer antigen may be selected from the group consisting of MAGE-A1, MAGE-A2, MAGE-A3, MAGE-A4, MAGE-A5, MAGE-A6, MAGE-A7, MAGE-A8, MAGE-A9, MAGE-A10, MAGE-A11, MAGE-A12, MAGE-Xp2 (MAGE-B2), MAGE-Xp3 (MAGE-B3), MAGE-Xp4 (MAGE-B4), MAGE-C1, MAGE-C2, MAGE-C3, MAGE-C4, MAGE-05), GAGE-1, GAGE-2, GAGE-3, GAGE-4, GAGE-5, GAGE-6, GAGE-7, GAGE-8, GAGE-9, BAGE, RAGE, LAGE-1, NAG, GnT-V, MUM-1, CDK4, tyrosinase, p53, MUC family, HER2/neu, p21ras, RCAS1, α-fetoprotein, E-cadherin, α-catenin, β-catenin, γ-catenin, p120ctn, gp100Pmel117, PRAME, NY-ESO-1, cdc27, adenomatous polyposis coli protein (APC), fodrin, Connexin 37, Ig-idiotype, p15, gp75, GM2 ganglioside, GD2 ganglioside, human papilloma virus proteins, Smad family of tumor antigens, lmp-1, PIA, EBV-encoded nuclear antigen (EBNA)-1, brain glycogen phosphorylase, SSX-1, SSX-2 (HOM-MEL-40), SSX-1, SSX-4, SSX-5, SCP-1 and CT-7, CD20, or c-erbB-2.

2. Adjuvants

An immunogenic composition can include a lipid conjugate that is an antigen such as an antigenic polypeptide-lipid conjugate, administered alone, or in combination with an adjuvant.

The adjuvant may be without limitation alum (e.g., aluminum hydroxide, aluminum phosphate); saponins purified from the bark of the *Q. saponaria* tree such as QS21 (a glycolipid that elutes in the 21st peak with HPLC fractionation; Antigenics, Inc., Worcester, Mass.); poly[di(carboxylatophenoxy)phosphazene (PCPP polymer; Virus Research Institute, USA), Flt3 ligand, *Leishmania* elongation factor (a purified *Leishmania* protein; Corixa Corporation, Seattle, Wash.), ISCOMS (immunostimulating complexes which contain mixed saponins, lipids and form virus-sized particles with pores that can hold antigen; CSL, Melbourne, Australia), Pam3Cys, SB-AS4 (SmithKline Beecham adjuvant system #4 which contains alum and MPL; SBB, Belgium), non-ionic block copolymers that form micelles such as CRL 1005 (these contain a linear chain of hydrophobic polyoxypropylene flanked by chains of polyoxyethylene, Vaxcel, Inc., Norcross, Ga.), and Montanide IMS (e.g., IMS 1312, water-based nanoparticles combined with a soluble immunostimulant, Seppic).

Adjuvants may be TLR ligands, such as those discussed above. Adjuvants that act through TLR3 include without limitation double-stranded RNA. Adjuvants that act through TLR4 include without limitation derivatives of lipopolysaccharides such as monophosphoryl lipid A (MPLA; Ribi ImmunoChem Research, Inc., Hamilton, Mont.) and muramyl dipeptide (MDP; Ribi) andthreonyl-muramyl dipeptide (t-MDP; Ribi); OM-174 (a glucosamine disaccharide related to lipid A; OM Pharma SA, Meyrin, Switzerland). Adjuvants that act through TLR5 include without limitation flagellin. Adjuvants that act through TLR7 and/or TLR8 include single-stranded RNA, oligoribonucleotides (ORN), synthetic low molecular weight compounds such as imidazoquinolinamines (e.g., imiquimod (R-837), resiquimod (R-848)). Adjuvants acting through TLR9 include DNA of viral or bacterial origin, or synthetic oligodeoxynucleotides (ODN), such as CpG ODN. Another adjuvant class is phosphorothioate containing molecules such as phosphorothioate nucleotide analogs and nucleic acids containing phosphorothioate backbone linkages.

The adjuvant can also be oil emulsions (e.g., Freund's adjuvant); saponin formulations; virosomes and viral-like particles; bacterial and microbial derivatives; immunostimulatory oligonucleotides; ADP-ribosylating toxins and detoxified derivatives; alum; BCG; mineral-containing compositions (e.g., mineral salts, such as aluminium salts and calcium salts, hydroxides, phosphates, sulfates, etc.); bioadhesives and/or mucoadhesives; microparticles; liposomes; polyoxyethylene ether and polyoxyethylene ester formulations; polyphosphazene; muramyl peptides; imidazoquinolone compounds; and surface active substances (e.g. lysolecithin, pluronic polyols, polyanions, peptides, oil emulsions, keyhole limpet hemocyanin, and dinitrophenol).

Adjuvants may also include immunomodulators such as cytokines, interleukins (e.g., IL-1, IL-2, IL-4, IL-5, IL-6, IL-7, IL-12, etc.), interferons (e.g., interferon-.gamma.), macrophage colony stimulating factor, and tumor necrosis factor.

C. Combination Therapies

In some embodiments, the conjugates are administered in combination with one or more additional therapeutic agents. The agents can be administered in the same pharmaceutical composition as the conjugates or the conjugates and the additional therapeutic agent can be administered in separate pharmaceutical compositions.

In some embodiments, the conjugates are administered in combination with a conventional therapeutic agent used for treatment of the disease or condition being treated. Conventional therapeutics agents are known in the art and can be determined by one of skill in the art based on the disease or disorder to be treated. For example, if the disease or condition is cancer, the conjugates can be co-administered with a chemotherapeutic drug; or if the disease or condition is a bacterial infection, the conjugates can be co-administered with an antibiotic.

IV. Methods of Use

A. Methods of Delivering Immunostimulatory Agents

1. Lymph Node Targeting

The data presented below supports the discovery that conjugating a cargo such as an oligonucleotide, or peptide, to an albumin-binding domain can increase delivery and accumulation of the cargo to the lymph nodes. The lymph nodes are oval-shaped organs of the immune system, distributed widely throughout the body including the armpit and stomach and linked by lymphatic vessels. Lymph nodes are bastions of B, T, and other immune cells. Lymph nodes act as filters or traps for foreign particles and are important in the proper functioning of the immune system. They are packed tightly with the white blood cells called lymphocytes and macrophages.

Lymph node targeting conjugates are typically transported from the injection site to secondary organs of the lymphatic system (e.g., lymph nodes), where interact with immune cells. It is believed that albumin-binding of the conjugates prevents the conjugates from rapidly flushing into the bloodstream and re-targets them to lymphatics and draining lymph nodes, where they are filtered, accumulate, and present their immunostimulatory oligonucleotide, antigenic peptide, or other cargo to immune cells.

As discussed above, albumin-binding lipids can be conjugated to, for example, an immunostimulatory oligonucleotide or an antigenic peptide which increases the immunostimulatory effect of the oligonucleotide or the antigenic peptide compared to administering non-conjugated oligonucleotide or antigenic peptide. In some embodiments, conjugation of the immunostimulatory oligonucleotide or peptide antigen to the an albumin-binding lipid increases accumulation of the cargo 2, 3, 4, 5, 6, 7, 8, 9, 10, or more fold compare to unconjugated cargo.

2. Tissue Specific Targeting

Micelle-stabilizing conjugates can be used to increase delivery and accumulation of the cargo to the tissue at or near a site of administration. Micelle-stabilizing conjugates are believed to be resistant to disruption by serum proteins such as albumin. Therefore, they can accumulate at the site of injection, for example, by binding to extracellular matrix proteins, or inserting into the cell membranes of local cells.

Micelle-stabilizing conjugates can be used to increase local accumulation of immunostimulatory oligonucleotides, antigenic peptides, small molecules, and other targets at the site of administration. In some embodiments, conjugation of the immunostimulatory oligonucleotide or peptide antigen increases local accumulation of the cargo 2, 3, 4, 5, 6, 7, 8, 9, 10, or more fold compare to unconjugated cargo.

B. Methods of Increasing an Immune Response

Lipid conjugates including an immunostimulatory oligonucleotide or antigenic peptide cargo can be administered in an effective amount to induce, increase or enhance an immune response. The "immune response" refers to responses that induce, increase, induce, or perpetuate the activation or efficiency of innate or adaptive immunity. Further, albumin-binding lipid conjugates of polypeptide antigens administered in the absence of other adjuvants may be used to promote tolerance rather than immunity, e.g., to an allergen or autoimmune antigen. The conjugates can be delivered parenterally (by subcutaneous, intradermal, or intramuscular injection) through the lymphatics, or by systemic administration through the circulatory system. It is noted that the lymph nodes can filter albumin-bound conjugates. Therefore, in some embodiments parenteral administration does not result in systemic distribution as the conjugates may be preferentially filtered by the closest lymph node(s). This tendency also reduces systemic toxicity such as swelling of the spleen.

Accordingly, in some embodiments, the conjugates are administered at a site adjacent to or leading to one or more lymph nodes which are close to the site in need of an immune response (i.e., close to a tumor or site of infection). In some embodiments, the conjugates are administered in multiple doses at various locations throughout the body. The conjugates, particularly micelle-stabilizing conjugates can also be administered directly to a site in need of an immune response (e.g., a tumor or site of infection).

The immune response can be induced, increased, or enhanced by the lipid conjugate compared to a control, for example an immune response in a subject induced, increased, or enhanced by the cargo alone, or the cargo delivered using an alternative delivery strategy such as liposomes. As discussed in more detail below, in some embodiments, lipid conjugates reduce inactivation and/or prolong activation of T cells (i.e., increase antigen-specific proliferation of T cells, enhance cytokine production by T cells, stimulate differentiation ad effector functions of T cells and/or promote T cell survival) or overcome T cell exhaustion and/or anergy.

The lipid conjugates can be used, for example, to induce an immune response, when administering the cargo alone, or the cargo in combination with an alternative delivery system, is ineffectual. The lipid conjugates can also be used to enhance or improve the immune response compared to administering cargo alone. In some embodiments, the lipid conjugates may reduce the dosage required to induce, increase, or enhance an immune response; or reduce the time needed for the immune system to respond following administration.

Lipid conjugates may be administered as part of prophylactic vaccines or immunogenic compositions which confer resistance in a subject to subsequent exposure to infectious agents, or as part of therapeutic vaccines, which can be used to initiate or enhance a subject's immune response to a pre-existing antigen, such as a viral antigen in a subject infected with a virus or with cancer.

The desired outcome of a prophylactic or therapeutic immune response may vary according to the disease or condition to be treated, or according to principles well known in the art. For example, an immune response against an infectious agent may completely prevent colonization and replication of an infectious agent, affecting "sterile immunity" and the absence of any disease symptoms. However, a vaccine against infectious agents may be considered effective if it reduces the number, severity or duration of symptoms; if it reduces the number of individuals in a population with symptoms; or reduces the transmission of an infectious agent. Similarly, immune responses against cancer, allergens or infectious agents may completely treat a disease, may alleviate symptoms, or may be one facet in an overall therapeutic intervention against a disease.

The lipid conjugates induce an improved effector cell response such as a CD4 T-cell immune response, against at least one of the component antigen(s) or antigenic compositions compared to the effector cell response obtained with the corresponding composition without the lipid conjugate. The term "improved effector cell response" refers to a higher effector cell response such as a CD8 or CD4 response obtained in a human patient after administration of the vaccine composition than that obtained after administration of the same composition without a lipid conjugate.

The improved effector cell response can be obtained in an immunologically unprimed patient, i.e. a patient who is seronegative to the antigen. This seronegativity may be the result of the patient having never faced the antigen (so-called "naïve" patient) or, alternatively, having failed to respond to the antigen once encountered. In some embodiments, the improved effector cell response is obtained in an immunocompromised subject.

The improved effector cell response can be assessed by measuring the number of cells producing any of the following cytokines: (1) cells producing at least two different cytokines (CD40L, IL-2, IFN-gamma, TNF-alpha); (2) cells producing at least CD40L and another cytokine (IL-2, TNF-alpha, IFN-gamma); (3) cells producing at least IL-2 and another cytokine (CD40L, TNF-alpha, IFN-gamma); (4) cells producing at least IFN-gamma and another cytokine (IL-2, TNF-alpha, CD40L); (5) and cells producing at least TNF-alpha and another cytokine (IL-2, CD40L, IFN-gamma).

An improved effector cell response is present when cells producing any of the above cytokines will be in a higher amount following administration of the vaccine composition compared to control as discussed above.

In a preferred embodiment, the composition increases the number of T cells producing IFN-gamma, TNF-alpha, or a combination thereof, or increases the production of IFN-gamma, TNF-alpha, or a combination thereof in the existing T cells.

In some embodiments, the administration of the immunogenic composition alternatively or additionally induces an improved B-memory cell response in patients administered lipid conjugates compared to a control. An improved B-memory cell response is intended to mean an increased frequency of peripheral blood B lymphocytes capable of differentiation into antibody-secreting plasma cells upon antigen encounter as measured by stimulation of in vitro differentiation.

In a still another embodiment, the immunogenic composition increases the primary immune response as well as the CD8 response. The administration of the lipid conjugates induces an improved CD4 T-cell, or CD8 T-cell immune response against a specific antigen compared to a control. This method may allow for inducing a CD4 T cell response which is more persistent in time.

Preferably the CD4 T-cell immune response, such as the improved CD4 T-cell immune response obtained in an unprimed subject, involves the induction of a cross-reactive CD4 T helper response. In particular, the amount of cross-reactive CD4 T cells is increased. The term "cross-reactive" CD4 response refers to CD4 T-cell targeting shared epitopes for example between influenza strains.

C. Diseases to be Treated

1. Cancer

The disclosed lipid conjugates are useful for stimulating or enhancing an immune response in host for treating cancer. The types of cancer that may be treated with the provided compositions and methods include, but are not limited to, the following: bladder, brain, breast, cervical, colo-rectal, esophageal, kidney, liver, lung, nasopharangeal, pancreatic, prostate, skin, stomach, uterine, ovarian, testicular and hematologic.

Malignant tumors which may be treated are classified herein according to the embryonic origin of the tissue from which the tumor is derived. Carcinomas are tumors arising from endodermal or ectodermal tissues such as skin or the epithelial lining of internal organs and glands. Sarcomas, which arise less frequently, are derived from mesodermal connective tissues such as bone, fat, and cartilage. The leukemias and lymphomas are malignant tumors of hematopoietic cells of the bone marrow. Leukemias proliferate as single cells, whereas lymphomas tend to grow as tumor masses. Malignant tumors may show up at numerous organs or tissues of the body to establish a cancer.

The conjugates can be administered in as an immunogenic composition or as part of vaccine, such as prophylactic vaccines, or therapeutic vaccines, which can be used to initiate or enhance a subject's immune response to a pre-existing antigen, such as a tumor antigen in a subject with cancer.

The desired outcome of a prophylactic or therapeutic immune response may vary according to the disease, according to principles well known in the art. Similarly, immune responses against cancer, may alleviate symptoms, or may be one facet in an overall therapeutic intervention against a disease. For example, administration of the lipid conjugates may reduce tumor size, or slow tumor growth compared to a control. The stimulation of an immune response against a cancer may be coupled with surgical, chemotherapeutic, radiologic, hormonal and other immunologic approaches in order to affect treatment.

2. Infectious Diseases

In a preferred embodiment, the lipid conjugates are useful for treating acute or chronic infectious diseases. Because viral infections are cleared primarily by T-cells, an increase in T-cell activity is therapeutically useful in situations where more rapid or thorough clearance of an infective viral agent would be beneficial to an animal or human subject. Thus, the lipid conjugates antagonists can be administered for the treatment of local or systemic viral infections, including, but not limited to, immunodeficiency (e.g., HIV), papilloma (e.g., HPV), herpes (e.g., HSV), encephalitis, influenza (e.g., human influenza virus A), and common cold (e.g., human rhinovirus) viral infections. For example, pharmaceutical formulations including the lipid conjugates can be administered topically to treat viral skin diseases such as herpes lesions or shingles, or genital warts. The lipid conjugates can also be administered to treat systemic viral diseases, including, but not limited to, AIDS, influenza, the common cold, or encephalitis.

Representative infections that can be treated, include but are not limited to infections cause by microoganisms including, but not limited to, *Actinomyces, Anabaena, Bacillus, Bacteroides, Bdellovibrio, Bordetella, Borrelia, Campylobacter, Caulobacter, Chlamydia, Chlorobium, Chromatium, Clostridium, Corynebacterium, Cytophaga, Deinococcus, Escherichia, Francisella, Halobacterium, Heliobacter, Haemophilus, Hemophilus* influenza type B (HIB), *Histoplasma, Hyphomicrobium, Legionella, Leishmania, Leptspirosis, Listeria, Meningococcus* A, B and C, *Methanobacterium, Micrococcus, Myobacterium, Mycoplasma, Myxococcus, Neisseria, Nitrobacter, Oscillatoria, Prochloron, Proteus, Pseudomonas, Phodospirillum, Rickettsia, Salmonella, Shigella, Spirillum, Spirochaeta, Staphylococcus, Streptococcus, Streptomyces, Sulfolobus, Thermoplasma, Thiobacillus,* and *Treponema, Vibrio, Yersinia, Cryptococcus neoformans, Histoplasma capsulatum, Candida albicans, Candida tropicalis, Nocardia asteroides, Rickettsia ricketsii, Rickettsia typhi, Mycoplasma pneumoniae, Chlamydial psittaci, Chlamydial trachomatis, Plasmodium falciparum, Plasmodium vivax, Trypanosoma brucei, Entamoeba histolytica, Toxoplasma gondii, Trichomonas vaginalis* and *Schistosoma mansoni*.

In some embodiment, the type of disease to be treated or prevented is a chronic infectious disease caused by a bacterium, virus, protozoan, helminth, or other microbial pathogen that enters intracellularly and is attacked, e.g., by cytotoxic T lymphocytes.

In a preferred embodiment, infections to be treated are chronic infections cause by a hepatitis virus, a human immunodeficiency virus (HIV), a human T-lymphotrophic virus (HTLV), a herpes virus, an Epstein-Barr virus, or a human papilloma virus.

EXAMPLES

Example 1: Albumin-Binding Lipo-Oligo Conjugates Accumulate in the Lymph Nodes

Materials and Methods

Oligonucleotide Synthesis

Oligonucleotides were synthesized in 1.0 micromolar scale on an automated DNA synthesiszer (ABI 394, Applied Biosystems, Inc.). All DNA synthesis reagents including cholesteryl-TEG phosphoramadite and DMT-PEG-phosphoramadite were purchased from Glenres and Chemgenes and used by following manufacturer's instructions. Immunostimulatory CpG oligos employed were a type B sequence known as 1826. Synthesis of lipid phosphoramidite and solid phase conjugation was followed by previous reports. Particle size was determined by dynamic light scattering (DLS) using a 90Plus/ZetaPals particle size and ξ-potential analyzer (Brookhaven Instruments). DSPE-PEG$_{2000}$-Maleimide was purchased from Laysan Bio Inc. carboxyfluorescein labeled PEG$_{2000}$-DSPE were purchased from Avanti Polar lipids Inc. carboxyfluorescein labeled NHS-PEG$_{2000}$ was purchased from nanocs Inc. Peptides were purchased from Genscript Corp. (Piscataway, N.J.). Incomplete Freund s adjuvant (IFA) and fatty acid free BSA were purchased from Sigma-Aldrich.

Synthesis of Diacyllipid Phophoramidite

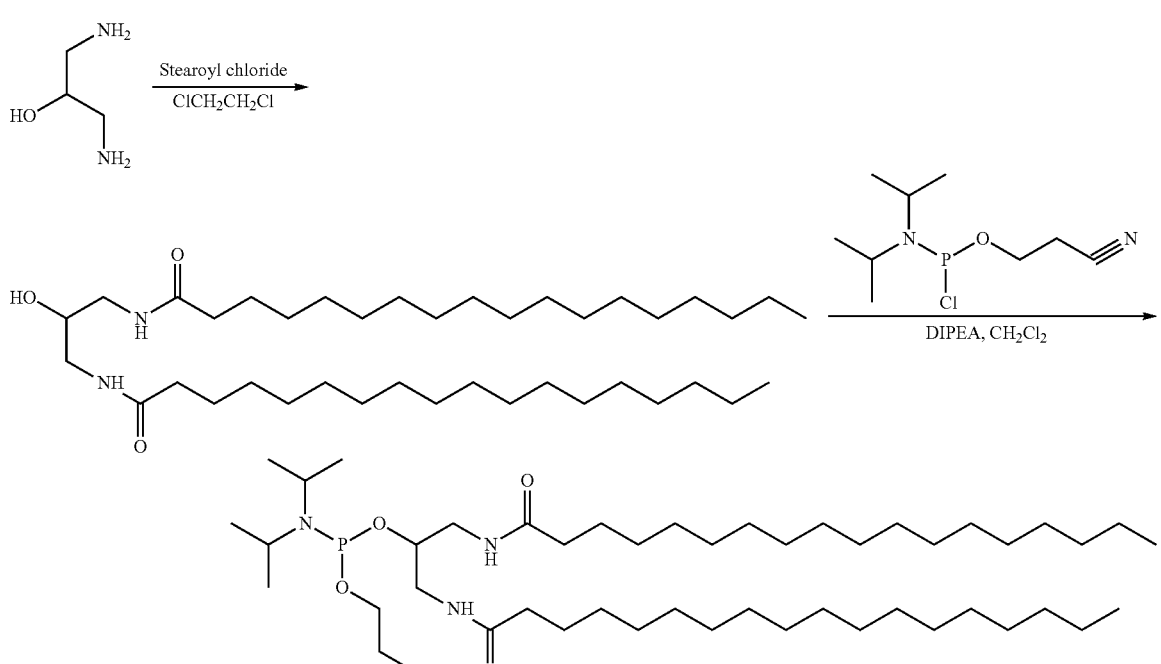

The diacyllipid phosphoramidite was synthesized in two steps as described by Liu, et al. *J. Angew. Chem., Int. Ed.* 2011, 50, 7252-7255.

A solution of stearoyl chloride (6.789 g, 22.41 mmol) in ClCH$_2$CH$_2$Cl (50 ml) was added dropwise to a solution of 1,3-diamino-2-dydroxypropane (1.0 g, 11.10 mmol) in the presence of ClCH$_2$CH$_2$Cl (100 ml) and triethylamine (2.896 g, 22.41 mmol). The reaction mixture was stirred for 2 hours at room temperature and then heated at 70° C. overnight. The reaction mixture was then cooled to RT, filtered, and the solid was washed with CH$_2$Cl$_2$, CH$_3$OH, 5%

NaHCO$_3$ and diethyl ether, respectively. The solid was dried under vacuum to give the intermediate product as a white solid (yield: 90%). $^1$H NMR (300 MHz, CDCl$_3$): δ 6.3 (m, 2H), 3.8 (m, 1H), 3.4-3.2 (m, 4H), 2.2 (t, 4H), 1.6 (m, 4H), 1.3-1.2 (m, 60H), 0.9 (t, 6H). The intermediate product (5.8 g, 9.31 mmol) and DIPEA (4.2 mL, 18.62 mmol) was then dissolved in anhydrous CH$_2$Cl$_2$ (100 ml). The solution was cooled on an ice bath and 2-Cyanoethyl N,N-diisopropylchlorophosphoramidite (8.6 mL, 0.47 mmol) was added dropwise under dry nitrogen. After stirring at RT for 1 hour, the solution was heated to 60° C. for 90 minutes. The reaction mixture was washed with 5% NaHCO$_3$ and brine, dried over Na$_2$SO$_4$ and concentrated under vacuum. The final product was isolated by precipitation from acetone to afford 4 g (55% yield) phosphoramidite as a white solid. $^1$H NMR (300 MHz, CDCl$_3$): δ 6.4 (m, 2H), 3.9 (m, 2H), 3.8 (m, 2H), 3.6 (m, 2H), 3.0-2.9 (m, 2H), 2.6 (t, 2H), 2.2 (m, 4H), 1.6 (m, 6H), 1.3-1.2 (m, 72H), 0.9 (t, 6H). $^{31}$P NMR (CDCl$_3$) 154 ppm.

called syringe synthesis technique (Storhoff, et al., *J Am. Chem. Soc.*, 120:1959-1964 (1999)). Briefly, lipid phosphoramidites (200 µL) were mixed with activator (0.2 mM 5-Ethylthio Tetrazole in 200 µL Acetonitrile), and the mixture were pushed back and forth through the CpG column using 2 syringes for 10 min. Alternatively, lipophilic phosphoramidite could also be coupled using the DNA synthesizer (15 min coupling time). After the synthesis, DNA was cleaved from the CpG and deprotected and purified by reverse phase HPLC using a C4 column (BioBasic-4, 200 mm×4.6 mm, Thermo Scientific), 100 mM triethylamine-acetic acid buffer (TEAA, pH 7.5)-acetonitrile (0-30 min, 10-100%) as an eluent. Lipophilic ODNs typically eluted at 20 min while unconjugated ODNs eluted at 8 min. Immunostimulatory CpG oligos employed were a type B sequence known as 1826 (Ballas, et al., *J. Immunol.*, 167, 4878-4886 (2001)).

Typical sequence of Lipo-G$_n$-CpG: 5'diacyllipid-*G$_n$*T*C*C*A*T*G*A*C*G*T*T*C*C*T*G*A*C*G*T *T*-3' (SEQ ID NO:1)

Synthesis of Pyrene Phosphoramidite

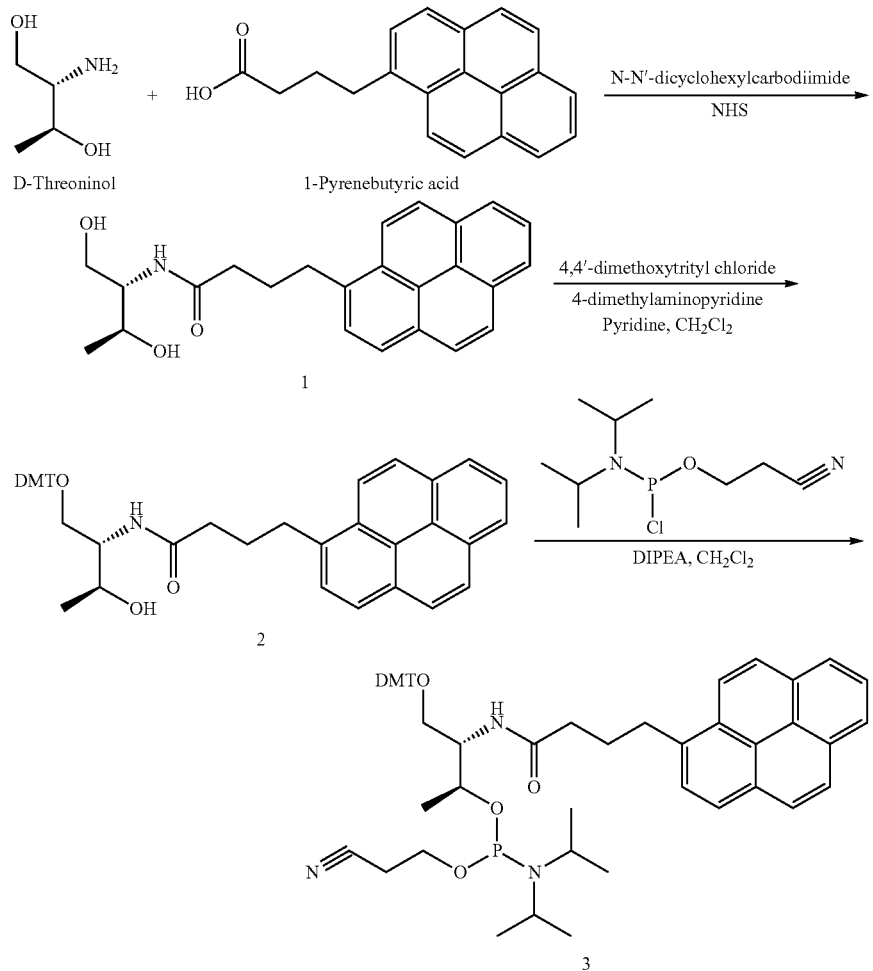

DNA Synthesis and Lipophilic Conjugation

All DNA and RNA sequences were synthesized using an ABI 394 synthesizer on 1.0 micromole scale. All lipophilic phosphoramidites were conjugated as a final 'base' on 5' end of the oligos. Lipophilic phosphoramidites were dissolved in dichloromethane and coupled to oligos by using the so- Synthesis of compound 1: In a 300 ml round-bottom flask, D-threoninol (0.95 g, 9.1 mmol), 1-Pyrenebutyric acid (2.88 g, 10.0 mmol), DCC (2.06 g, 10.0 mmol) and NHS (1.15 g, 10 mmol) were dissolved in 50 ml DMF. The reaction mixture was stirred at room temperature for 24 hours. The insoluble N,N'-dicyclohexylurea was filtered, and DMF was removed with a rotary vacuum evaporator to obtain an oily crude product. Compound 1 was purified by flash chromatography (yield: 85%). 1H NMR (300 MHz, CDCl$_3$): δ 8.1-7.7 (m, 9H), 6.2 (d, 1H), 4.2-3.8 (m, 4H), 3.0 (m, 2H), 2.3-2.2 (m, 4H), 1.2 (d, 3H).

Synthesis of compound 2: Compound 1 (2.93 g, 7.2 mmol) and 4-dimethylaminopyridine (0.043 g, 0.36 mmol) in 40 ml dry pyridine in a 100 ml round-bottom flask under dry nitrogen. The solution was cooled on an ice bath. DMT-Cl (2.93 g, 8.64 mmol) was dissolved in 10 ml dry CH2Cl2 in a 50 ml flask under nitrogen and slowly added to the above pyridine solution under dry nitrogen. The reaction was slowly warmed up to room temperature and stirred for 24 hours. The solvent was removed under vacuum, and compound 2 was isolated by chromatography (50:50:3 ethyl acetate:hexane/triethylamine) (yield: 75%). 1H NMR (300 MHz, CDCl$_3$): δ 8.3-7.5 (m, 22H), 6.1 (d, 1H), 4.2-3.9 (m, 2H), 3.7 (d, 6H), 3.4-3.3 (m, 4H), 2.4-2.2 (m, 4H), 1.2 (d, 3H).

Synthesis of compound 3: Compound 2 (1 g, 1.48 mmol) was dissolved in CH2Cl2 and cooled on an ice bath. Then, DIPEA (0.57 g, 4.44 mmol) and 2-Cyanoethyl N,N-diisopropylchlorophosphoramidite (0.42 g, 1.78 mmol) were added under dry nitrogen. The reaction mixture was stirred on ice for 3 hours. The solvent was evaporated, and compound 3 was purified by chromatography (50:50:3 ethyl acetate:hexane/triethylamine) (Yield: 70%). 1H NMR (300 MHz, CDCl$_3$): δ 8.3-6.6 (m, 21H), 5.82 (d, 1H), 4.4-4.2 (m, 2H), 3.8 (s, 3H), 3.7 (d, 6H), 3.6-3.1 (m, 8H), 2.5 (m, 1H), 2.4-2.2 (m, 5H), 1.3-0.9 (m, 20H). 31P NMR (CDCl$_3$) 149.

Size-Exclusion Chromatography

Size-exclusion chromatography was carried out on a Shimadzu HPLC system equipped with a SEC-biosil column (repacked in a 200×4.6 mm column). Samples were eluted using 1×PBS+20 mM KCl at flow rate 0.5 mL per minute. In a typical experiment, 80 µL of 5 µM lipo-G$_n$T$_{10-n}$CpG-Fam in 1×PBS+20 mM KCl were added 20 µL FBS (Greiner Bio-one), samples were briefly votexed and incubated at 37° C. for 2 hours then diluted in 500 µL 1×PBS with 20 mM KCl, sample were then analyzed by SEC, FBS was monitored using absorptions at 280 nm, while ODNs were monitored at 480 nm (Fam peak).

Circular Dichroism Spectometer Measurements

5 µM CpG ODNs were dissolved in 1×PBS with 20 mM KCl. Circular Dichroism (CD) spectra were recorded on an Aviv Model 202 Circular Dichroism Spectrometer at 20° C. Scans from 220 to 320 nm were performed with 100 nm/min scanning speed, 1 nm bandwidth. For each spectrum, an average of three scans was taken, spectral contribution from the buffer was subtracted.

Animals and Cells

Animals were cared for in the USDA-inspected MIT Animal Facility under federal, state, local and NIH guidelines for animal care. C57BL/6 albino mice (6-8 weeks) were obtained from the Jackson Laboratory. Cells were cultured in complete medium (MEM, 5% fetal bovine serum (Greiner Bio-one), 100 U/ml penicillin G sodium and 100 µg/ml streptomycin (Pen/Strep), MEM sodium pyruvate (1 mM), NaH$_2$CO$_3$, MEM vitamins, MEM non-essential amino acids (all from Invitrogen), 20 µM β-mercaptoethanol (β-ME)).

Statistical Analysis

All error bars represent SEM. Comparisons of mean values were performed using unpaired Student's t tests. *, $p<0.05$; , $p<0.01$; *, $p<0.001$. Graphpad Prism 5 software was used.

Results

Albumin serves as the main fatty acid transporter in extracellular fluids. Experiments were designed to test if antigen/adjuvants modified with a lipophilic albumin-binding domain would accumulate in lymphoid organs following injection via in situ complexation and transport with endogenous albumin. To develop this strategy, model vaccines were developed that include peptide antigens combined with CpG DNAs, single-stranded oligonucleotides containing unmethylated cytosine-guanine motifs that bind Toll-like receptor-9 and serve as potent molecular adjuvants.

To identify an optimal albumin-binding domain that could be appended to either CpG or peptide antigens, a series of amphiphilic 20-base phosphorothioate (PS)-stabilized CpG oligos linked to various lipophilic tails via the 5' end (amph-CpGs) 3'-labeled with fluorescein amidite were constructed (FAM, FIG. 1A) and the interaction of these amphiphiles with serum proteins by size exclusion chromatography was evaluated (SEC, FIG. 2B). Fetal bovine serum (FBS) exhibited a major fraction of protein eluting at 5.3 min in SEC (coinciding with serum albumin). Diacyl lipid-conjugated CpGs (lipo-CpGs) in aq. solution eluted as micelles (3.7 min), but following incubation with 20% FBS for 2 hr, ~46% of this amph-CpG co-migrated with albumin (FIG. 2B). In contrast, the vast majority of mono-acyl-(C18-CpG) and cholesterol-(Cho-CpG) oligos eluted as unimers at 5.8 min essentially identical to unmodified CpG in the presence or absence of serum, indicating stability of the PS backbone against serum nuclease degradation and a lack of interaction with albumin (FIG. 2B).

Figure 1F:
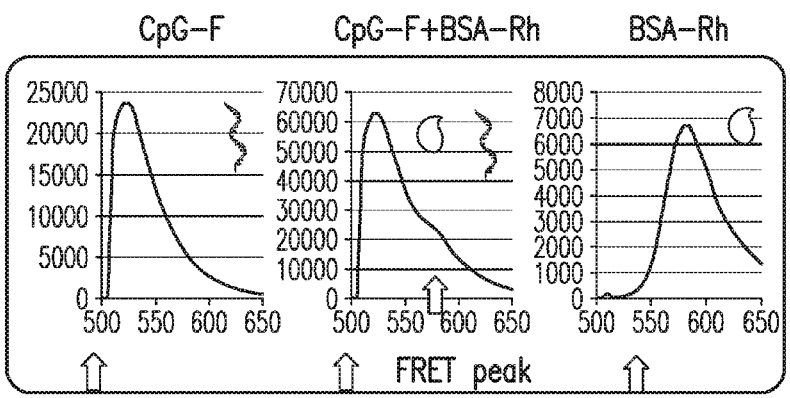
FIG. 1F is a series of plots showing fluorescence resonance energy transfer (FRET) of fluorescein labeled free CpG alone (left), fluorescein labeled free CpG mixed with rhodamine labeled bovine serum albumin (BSA) (center), and rhodamine labeled alone (right).
Figure 1G:
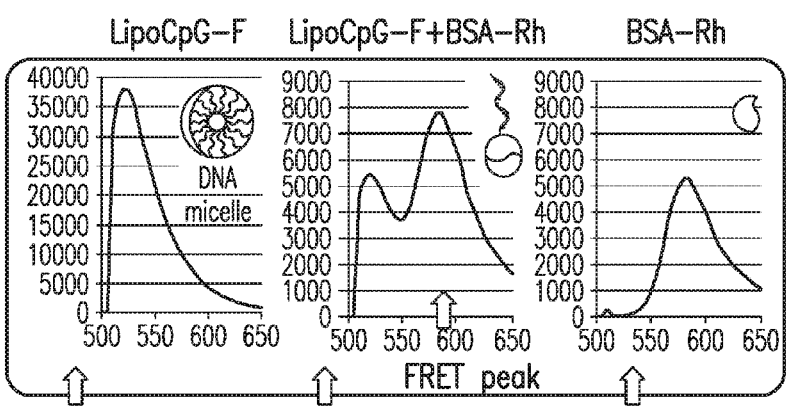
FIG. 1G is a series of plots showing fluorescence resonance energy transfer (FRET) of fluorescein labeled Lipo-CpG alone (left), fluorescein labeled Lipo-CpG mixed with rhodamine labeled bovine serum albumin (BSA) (center), and rhodamine labeled alone (right).

Spectroscopy measurements of FRET between FAM-labeled lipo-CpG and rhodamine-conjugated albumin confirmed molecular association of the diacyl lipid amphiphile and albumin in solution (FIGS. 1F and 1G).

To determine whether CpGs with different affinity for albumin exhibit differential LN targeting, amph-CpGs were injected s.c. at the tail base of mice, and 24 hr later, draining inguinal and axillary LNs were excised and analyzed intact by IVIS fluorescence imaging. C18-CpG and Cho-CpG showed marginally increased uptake in LNs relative to unmodified CpG. In contrast, lipo-CpG showed a dramatic increase in LN accumulation, 8-fold over soluble CpG at 24 hr, and much greater than CpG delivered in two prototypical vaccine vehicles, incomplete Freund's adjuvant or poly (ethylene glycol) (PEG)-coated liposomes. As shown by prior studies, the PS backbone used to stabilize the CpG oligos against serum nucleases promotes nonspecific binding to extracellular matrix at the injection site, leading to slow clearance of the oligos from the tissue over several days. However, soluble CpG levels reached an early low peak in the proximal LNs and exhibited no accumulation above 0.3% of the injected dose at any time (FIG. 2C). In contrast, lipo-CpG was detected in LNs within 2 hr post injection and continued to accumulate for 3 days before decaying, giving a total AUC of exposure to CpG in the draining LNs greater than soluble CpG over the week following injection. LN accumulation was not dependent on TLR-9-recognized CpG motifs, as non-CpG polythymidine amphiphiles (lipo-T$_{20}$) were detected in LNs at similarly high levels (FIG. 2J).

Example 2: Stabilized Micelles Exhibit Reduce Lymph Node Targeting

Materials and Methods

Flow Cytometry

All Antibodies were purchased from BD pharmingen or ebioscience. Cells were acquired on a FACScanto flow cytometer (BD biosciences) and analyzed using flowjo software (Tree Star Inc. Ashland, Oreg.).

Intracellular Cytokine Staining (ICCS)

Cells were plated in 96-well round-bottomed plates and pulsed with minimum peptides in the presence of brefeldin A for 6 hours in complete media at 37° C. Cells were stained with anti-CD8-APC and then fixed using Cytofix (BD biosciences) according to the manufacturer's instructions. Cells were then washed and permeabilized. Intracellular staining for anti-INF-γ-PE and anti-TNF-α-FITC was then performed according to BD's protocol. FACS data were collected and analyzed as described before.

Immunohistochemistry Staining

Immunofluorescent staining was performed on 10-μm frozen sections of lymph node biopsy specimens. To reduce fading of FITC, sections were mounted in Vectashield mounting medium. (Vector Laboratories, Inc. Brulingame, Calif.) and were viewed in a Zeiss LSM 510 microscope (Oberkochen, Germany). Staining for lymph nodes sections were done directly with an PE-labeled CD11c and APC-labeled F4/80, or PE-labeled B220 and APC-labeled CD3 antibodies.

Results

The in vitro analyses in Example 1 indicate that lipo-CpG molecules equilibrate between micellar and albumin-bound forms in the presence of serum. However, enhanced lymph node accumulation achieved by these amphiphiles could have been driven by either species. To distinguish these possibilities, poly-guanine repeats were introduced between the diacyl lipid and CpG sequence. G-quadruplex hydrogen bonding between adjacent oligo strands in lipo-$G_n$-CpG micelles containing 4 or more guanine repeats blocked access of albumin to the lipid tails and rendered the micelles stable against disassembly in the presence of serum (discussed in more detail below).

Figure 8A:
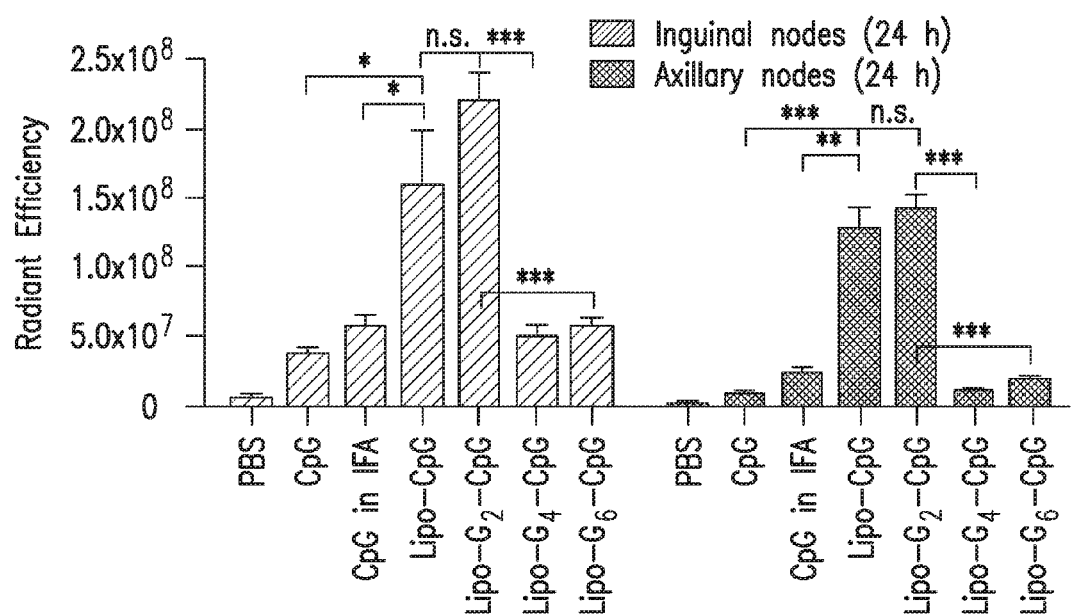
FIG. 8A is a bar graph showing quantitative accumulation (Radiant Efficiency) of various CpG-based micelles in the inguinal lymph nodes (left half of the graph) and axillary lymph nodes (right half of the graph) 24 hours post injection.

While albumin-binding lipo-CpG and lipo-$G_2$-CpG exhibited robust LN targeting, G-quartet-stabilized lipo-$G_4$-CpG or lipo-$G_6$-CpG micelles exhibited very poor LN accumulation following s.c. injection (FIG. 8A). (Note that the effect of different oligo lengths here is negligible, as lipo-$T_6$-CpG showed similar LN accumulation). Longitudinal analysis of CpG fluorescence at the injection site and draining LNs showed that the low LN accumulation of lipo-$G_{4/6}$-CpG amphiphiles was due to failure of the stabilized micelles to drain from the injection site. It is possible that amplification of nonspecific matrix binding by the PS DNA backbones in the multivalent micellar form irreversibly traps the majority of stabilized micelles at the injection site.

In agreement with the IVIS data, little detectable accumulation of CpG or lipo-$G_4$-CpG was seen in histological sections of draining inguinal LNs, while lipo-CpG and lipo-$G_2$-CpG accumulated in the subcapsular sinus and interfollicular areas reaching toward the paracortex. Immunohistochemical and flow cytometry analysis showed these LN-accumulating amphiphiles co-localized with F4/80+ macrophages and CD11c+ dendritic cells (FIG. 3E).

Example 3: Albumin "Hitchhiking" Targets Lipo-Oligo Conjugates to the Lymph Nodes Materials and Methods Albumin-CpG Conjugate Mouse serum albumin (10 mg in 200 uL PBS) was added 0.79 mg BMPS (Aldrich) dissolved in 20 uL DMSO. The mixture was agitated at RT for 2 hours. The extra BMPS was removed by passing the mixture through a G-25 column. After which the solution was added 246 ug disulfide labeled fluorescein-CpG (preactivated by 20 uL 100 mM TCEP). The mixture was allowed to react overnight and extra CpG was dialysized (50K MWCO) and the absence of free CpG was confirmed by size-exclusion chlomatography.

Results

If albumin "hitchhiking" is required for optimal targeting of CpG molecules to LNs, then covalent conjugation of oligos to albumin should lead to similar LN accumulation. To test this, CpG was covalently conjugated to mouse serum albumin (MSA) and compared LN uptake of these conjugates vs. lipo-CpG or soluble CpG. Statistically significant differences were observed between the conjugates and lipo-ODNs, the fluorescence intensity of both MSA-CpG and lipo-CpG in LNs was much greater than that of soluble ODN. Altogether, these data indicate that efficient LN accumulation of CpG oligonucleotides conjugated to lipophilic tails is dependent on the ability of the amphiphile to partition from micelles into a serum protein-bound state.

Figure 4A:
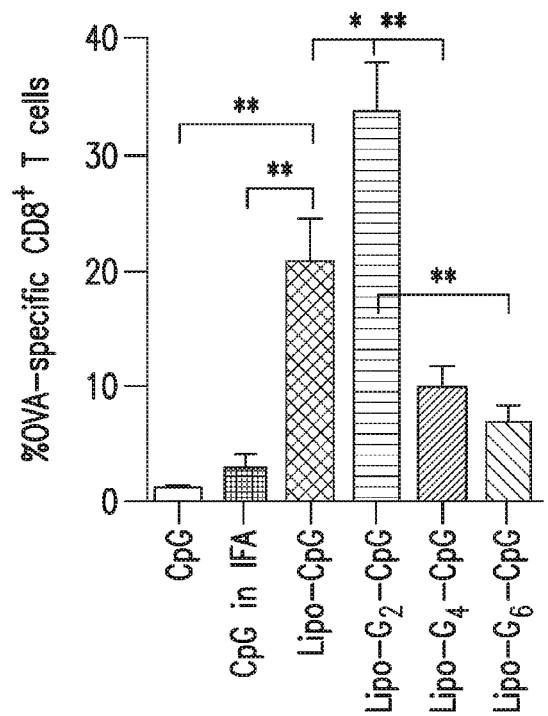
FIG. 4A is a bar graph showing the percentage of peripheral blood lymphocytes isolated from C57Bl/6 mice that are H-2K$^b$/SIINFEKL tetramer positive by flow cytometry 6 days after completion of an immunization protocol including s.c. injections on day 0 and day 14, with 10 μg OVA and in combinations of 1.24 nmol CpG formulations as indicated.

Example 4: Albumin-Binding Lipo-Oligo Conjugates Enhance Immune Responses while Minimize Systemic Toxicity In Vivo To determine the impact of LN targeting of CpG on the immune response, mice were immunized with ovalbumin (OVA) mixed with unmodified CpG, CpG in IFA, albumin-binding CpGs (lipo-$G_n$-CpG, n=0, 2) or G-Quadruplex-stabilized CpG micelles (lipo-$G_n$-CpG, n=4, 6). Animals were primed on day 0, boosted on day 14, and CD8+ T-cell responses were analyzed on day 20. Administration of lipid-conjugated CpGs, but not unconjugated CpG (soluble CpG or CpG emulsified in IFA), resulted in significantly increased frequencies of CD8+ T-cells that were specific for OVA$_{257-264}$ compared to unmodified CpG alone or emulsified in IFA. The strongest responses were elicited by albumin-binding lipo-CpG and lipo-$G_2$-CpG (FIG. 4A).

Figure 4B:
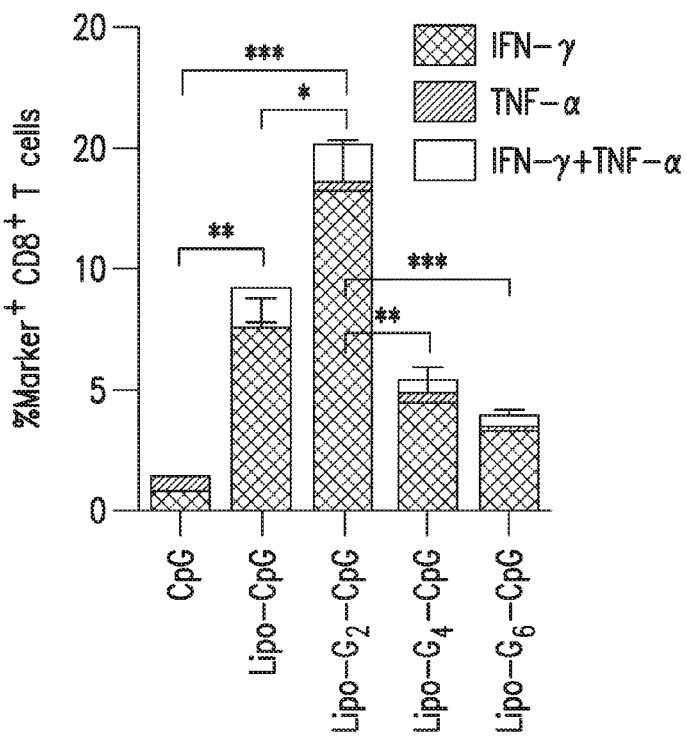
FIG. 4B is a bar graph showing quantifications of INF-γ and TNF-α positive CD8 T-Cells after 6 hrs. antigen-specific restimulation.
Figure 4C:
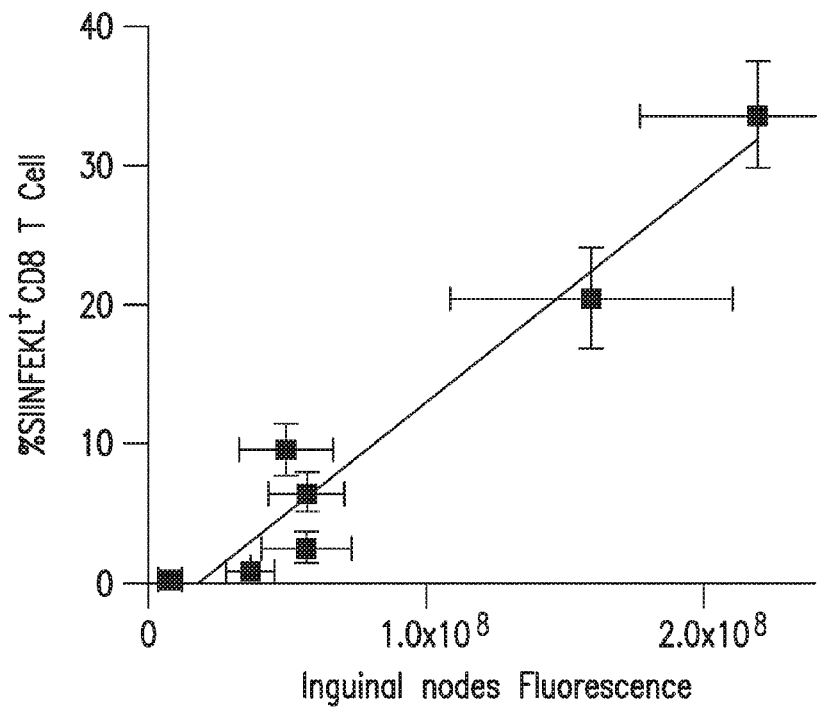
FIG. 4C is a line graph showing the correlation between LN CpG fluorescence and immune response measured by SIINFEKL tetramer staining

Intracellular cytokine staining on peripheral blood lymphocytes showed qualitatively identical trends, with large frequencies of IFN-g- and TNF-α-producing T-cells expanded by the albumin-binding CpG amphiphiles (FIG. 4B). Control immunizations with non-TLR agonist lipo-GpC or a PEG conjugate lipo-(PEG) with 48 ethylene glycol units mixed with OVA elicited minimal responses, ruling out a direct adjuvant effect of the diacyl lipid tail.

Figure 4D:
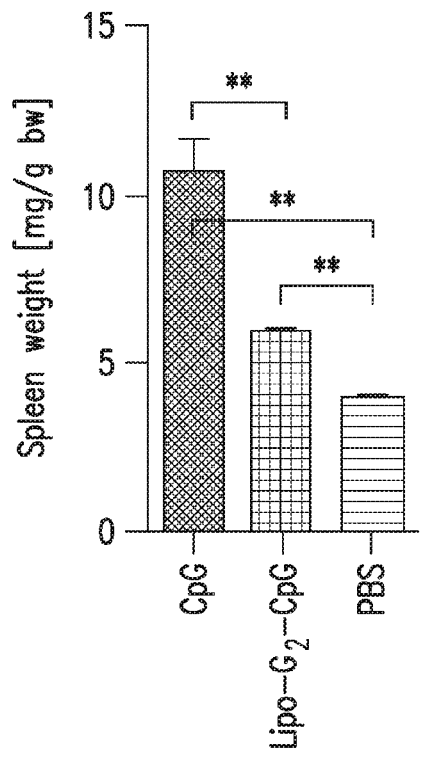
FIG. 4D is a bar graph showing the spleen weight (mg/g body weight) of CpG, Lipo-G$_2$-CpG, and PBS as an indicator of relative systemic toxicity of the different treatments.
Figure 4E:
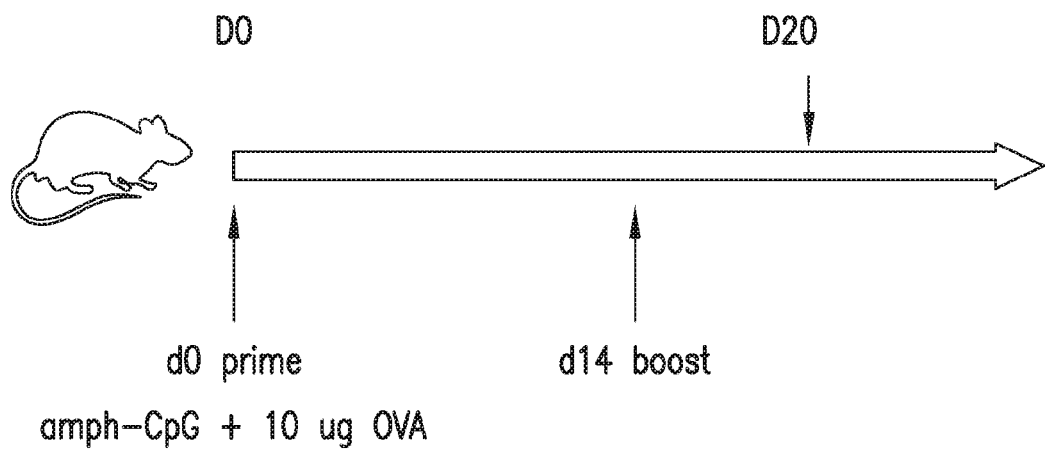
FIG. 4E is a schematic showing the assay design.
Figure 4F:
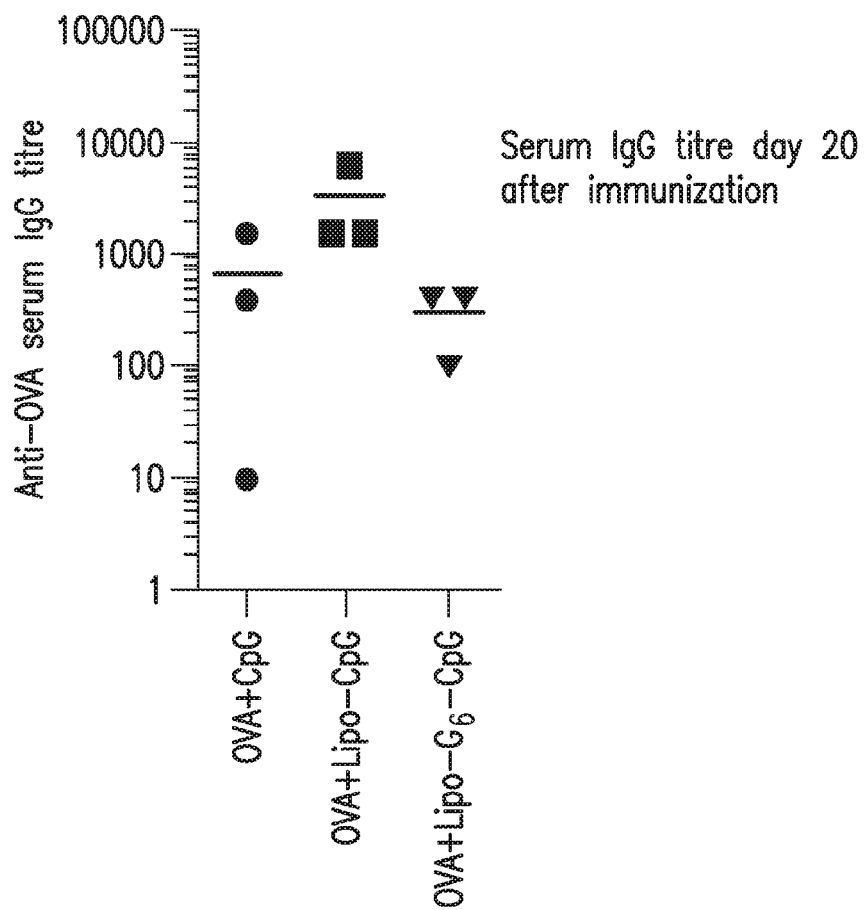
FIG. 4F is a dot plot showing the impact of LN targeting (Anti-OVA serum IgG titre 20 days after immunization with various antigen/adjuvant combinations as indicated) on the immune response.

Repeated injections of high doses albumin-binding CpGs subcutaneously did not induced generalized, non-specific immune activation in vivo, as characterized by systemic proinflammatory cytokines release (FIG. 10) and lymphocyte activation in the spleen (splenomegaly, FIG. 4D). In contrast, administration of free CpG in mice resulted in systemic toxicity (Figure. 10, FIG. 11). Taken together, these experiments strongly suggest lymph node targeting amph-CpGs are potent adjuvants capable of eliciting massive CD8 T-cell responses while avoiding systemic immune activation.

Example 5: Albumin "Hitchhiking" Targets Lipo-Peptide Conjugates to the Lymph Nodes Materials and Methods Synthesis of Fluorescein PEG Amphiphiles PE lipids (1,2-dilauroyl-sn-glycero-3-phosphoethanolamine, DMPE; 1,2-dimyristoyl-sn-glycero-3-phosphoethanolamine, DMPE; 1,2-dihexadecanoyl-sn-glycero-3-phosphoethanolamine, DPPE; 1,2-dioctadecanoyl-sn-glycero-3-phosphoethanolamine, DSPE, Avanti polar lipids. Inc.) were dissolved in 500 uL CHCl$_3$ and 500 uL DMF, 1.2 eq of fluorescein-PEG$_{2000}$-NHS (creative PEG works Inc.) was added and the reaction mixture were agitated overnight, the amphiphilic fluorescein PEG amphiphiles were purified by reverse phase HPLC using a C4 column (BioBasic-4, 200 mm×4.6 mm, Thermo Scientific), 100 mM triethylamine-acetic acid buffer (TEAA, pH 7.5)-methanol (0-30 min, 10-100%) as an eluent.

Synthesis of Peptide Amphiphiles

N-terminal cysteine modified peptides were dissolved in DMF and mixed with 2 equivalents Maleimide-PEG$_{2000}$-DSPE (Laysan Bio, Inc.), the mixture was agitated at RT for 24 hours. Bioconjugation was judged to be essentially complete by HPLC analysis. The peptide conjugate was then diluted in 10×ddH$_2$O and lyophilized into powder, redissolved in H$_2$O and stored under −80° C.

Results

Synthesis of lipo-CpG is straightforward due to the solubility promoted by the long polar oligonucleotide block, but depending on the amino acid sequence, lipidated peptides can be essentially insoluble. Thus, to generalizable the lymph node targeting approach achieved with lipo-CpG to peptide antigens and other potential vaccine components, lipo-PEG amphiphiles composed of a diacyl lipid tail linked to peptide cargos via a polar PEG block (amph-peptides; e.g., FIG. 1C) were generated using ethylene glycol spacers of varying lengths to mimic the long polar block of lipo-CpG.

Figure 2F:
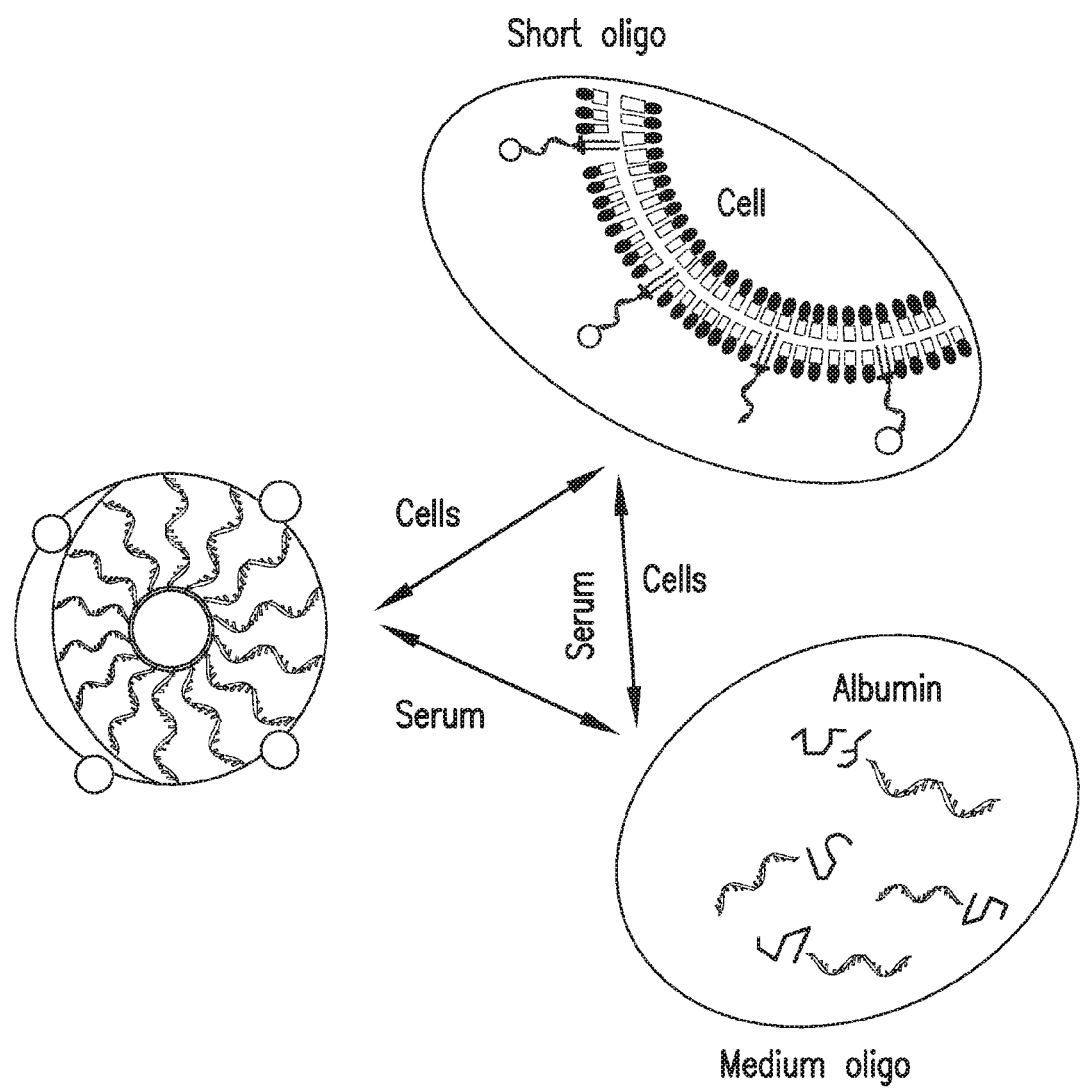
FIG. 2F is an illustration showing that the length of the polar block controls the balance of three-way equilibrium: intact micelles, albumin bound amhiphiles and cell membrane inserted amphiphiles.
Figure 2G:
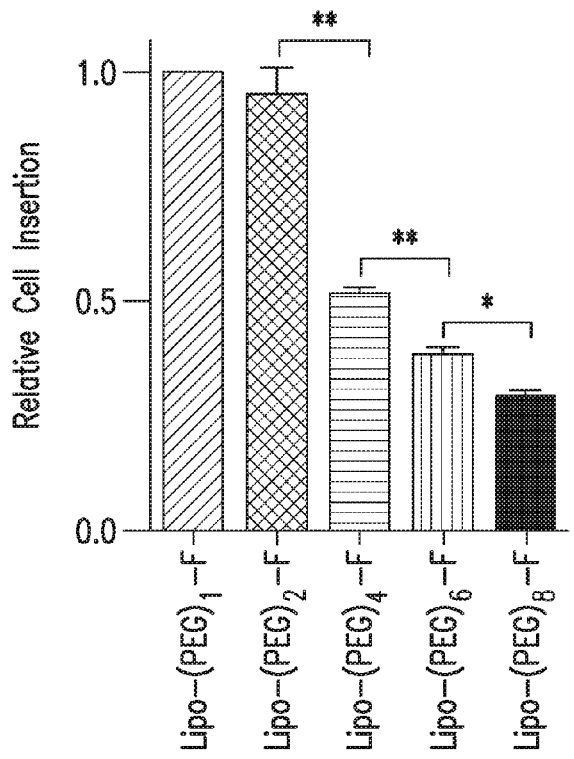
FIGS. 2G and H show the effect of varying the length of a poly(ethylene glycol) (PEG) linker of lipo-(PEG)$_n$-FITC conjugates on cell membrane insertion and lymph node targeting, where n is the number of 4-unit oliogethylene glycol repeats in the PEG block.
Figure 2H:
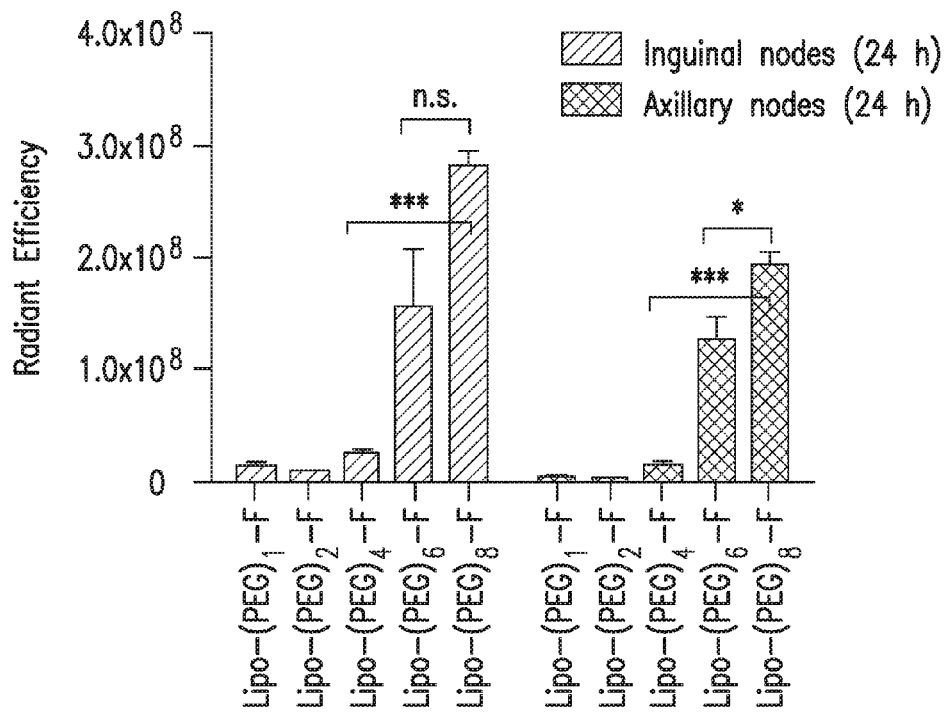
FIG. 2H is two bar graphs showing in vivo LN (inguinal nodes in the left graph, and auxiliary nodes in the right graph) accumulation of amphiphiles in different fluorescein-labeled formulations (Lipo-(PEG)$_n$-F (n=1, 2, 4, 6, 8)) 24 hours after subcutaneous injection.

The length of the PEG block in this design controls the balance of a 3-way equilibrium in physiological conditions: amph-peptides and lipo-PEGs in pure water form micelles, but in the presence of serum and cells these amphiphiles equilibrate between binding to albumin and insertion of their diacyl tails into cell membranes (FIG. 2F). Lipo-PEG-FAM amphiphiles with short PEG blocks showed stable plasma membrane insertion when incubated with cells in the presence of serum in vitro (FIG. 2G), which would block transit to LNs on albumin in vivo. However, increasing the polar block to 48 ethylene glycol units gave lipo-PEG amphiphiles that partitioned into solution while retaining albumin binding (FIG. 2G). This in vitro behavior directly predicted in vivo draining patterns, as lipo-PEG-FAM amphiphiles injected s.c. showed increasing LN accumulation with increasing PEG block length (increased for 48 EG units compared to 4 EG units, FIG. 2H).

Figure 2I:
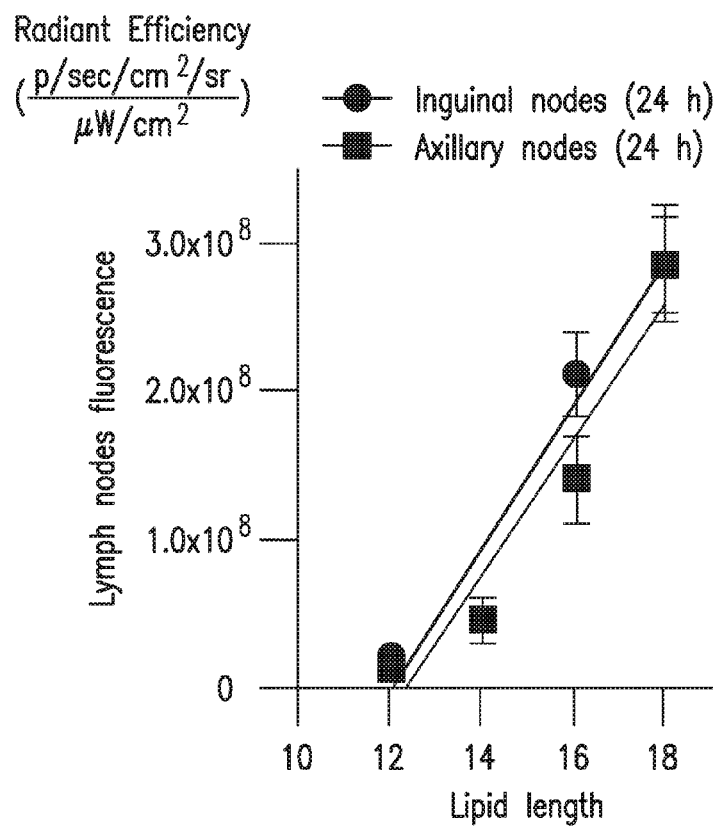
FIG. 2I is a line graph showing LNs uptake of amphiphilic fluorescein labeled PEG$_{2000}$ as a function of lipid molecular weight (i.e., length).
Figure 2J:
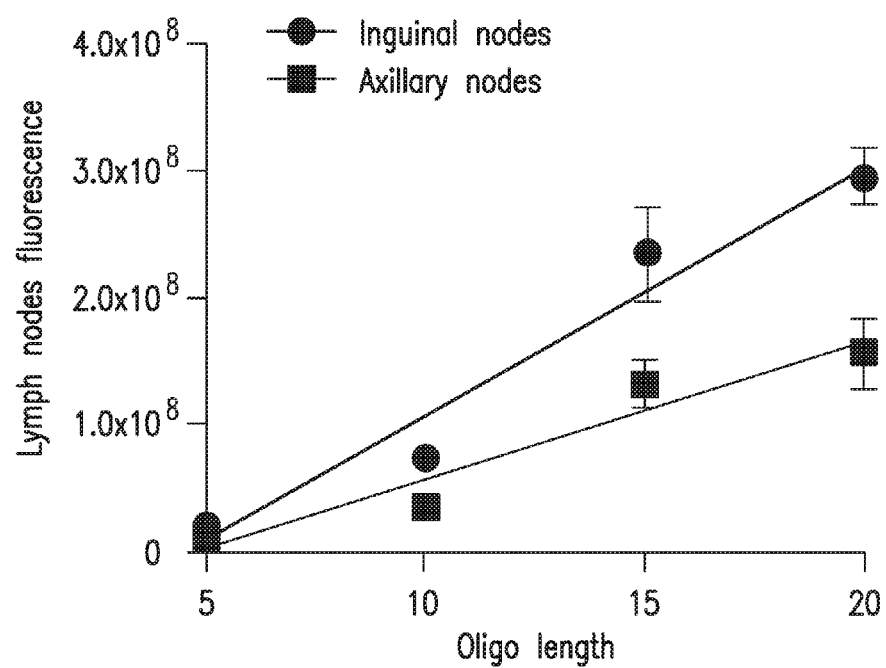
FIG. 2J is a line graph showing LNs uptake of lipid-oligonucleotide conjugates as a function of oligonucleotide length.

An analogous trend was observed for the DNA amphiphiles; lipo-Tn oligos prepared with increasing polythymidine strand length showed increasing accumulation in LNs following s.c. injection, up to a plateau accumulation for oligos (FIG. 2J). Like CpG amphiphiles, the structure of the hydrophobic block was also important; while lipo-PEG amphiphiles with long diacyl tails (≥16 carbons, which exhibit a high affinity for albumin) showed intense fluorescence in lymph nodes, shorter lipid tails with poor affinity for albumin showed low LN accumulation (FIG. 2I).

Example 6: Lymph Node-Targeted Vaccines Induce Immune Responses

Materials and Methods

Vaccine Ingredients

Minimum peptides were purchased from Anaspec; ovalbumin was purchased from Worthington Biochemical Corporation; cysteine (Cys) modified peptide HPV-16 E7$_{49-57}$ (CRAHYNIVTF), AL-11 (CAAVKNWMTQTL) and Trp-2 (CSVYDFFVWL) were synthesized by GenScript and purified by reverse phase HPLC. DSPE-PEG$_{2000}$-Maleimide was purchased from Laysan Bio Inc. CpG ODNs were synthesized in house. IFA was purchased from Sigma-Aldrich.

Vaccine Preparation

Mice were vaccinated by a prime-boost regimen, typically, each priming and boost vaccine in experiments consisted of the following ingredients: 10 μg OVA, 1.24 nmol CpG suspended in 1×PBS with 20 mM K$^+$, 10 mM Mg$^+$. In experiments in which the IFA was used, CpG/OVA were combined with same volume of IFA and extensively emulsified. The volume of all vaccine injections was 100 μl. For peptide micelle, mice were primed with 10 μg of peptide-PEG$_{2000}$-DSPE conjugate, mixed with 1.24 nmol CpGs suspended in 1×PBS with 20 mM K$^+$, 10 mM Mg$^+$ and boosted with 20 μg of peptide-PEG$_{2000}$-DSPE conjugate, mixed with 1.24 nmol CpGs. Mice were injected at the base of tail s.c.

Tetramer Staining

Tissue samples were collected and a single cell suspension (spleens and lymph nodes) was prepared. Blood were collected and red blood cells were depleted by ACK lysing buffer. Cells were then blocked with Fc-blocker (anti-mouse CD16/CD32 monoclonal antibody) and stained with PE labeled tetramers (Beckman Coulter) and anti-CD8-APC for 30 minutes at room temperature. Cells were washed twice and resuspended in FACS buffer. FACS data were collected on a BD FACScanto flow cytometer and analyzed using flowjo software. Analysis typically gated on CD8$^+$, Tetramer positive live cells.

In Vivo Cytotoxicity Assays

Splenocytes from naïve mice were pulsed with or without 10 μM SIINFEKL peptide for 30 min, cells were then labeled with either 1 μM (for pulsed cells) or 0.1 μM (control cells) CFSE for 10 min at 37° C. and extensively washed. Cells were mixed at a 1:1 ratio and 10×10$^6$ total cells were injected i.v. into mice challenged previously with vaccine formulations as described above. 18 hours later, splenocytes from each receipt mouse were analyzed by FACS to detect the CFSE labeled cells.

Results

Figure 9:
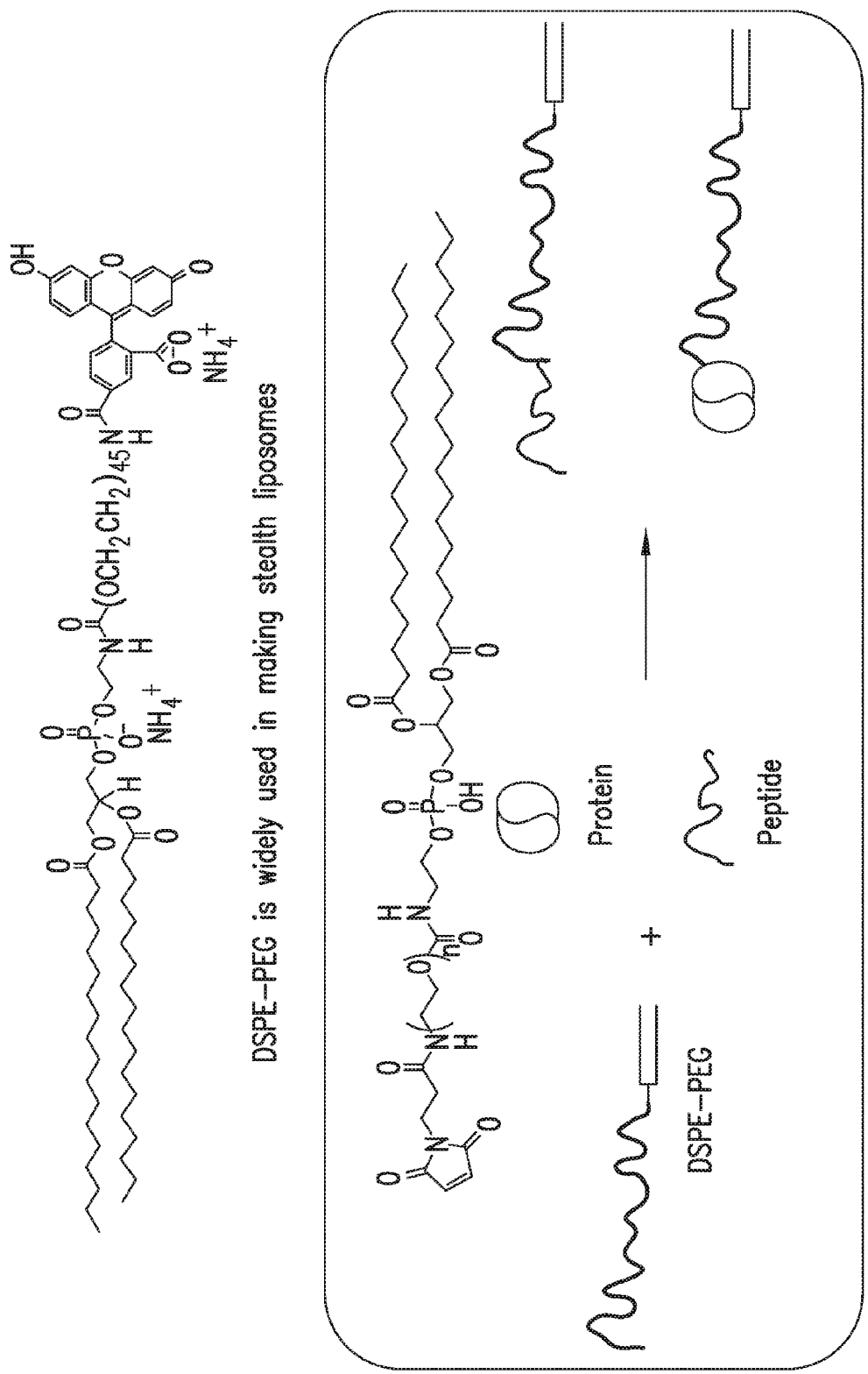
FIG. 9 is a schematic representation of a lipid-peptide conjugate.
Figure 10A:
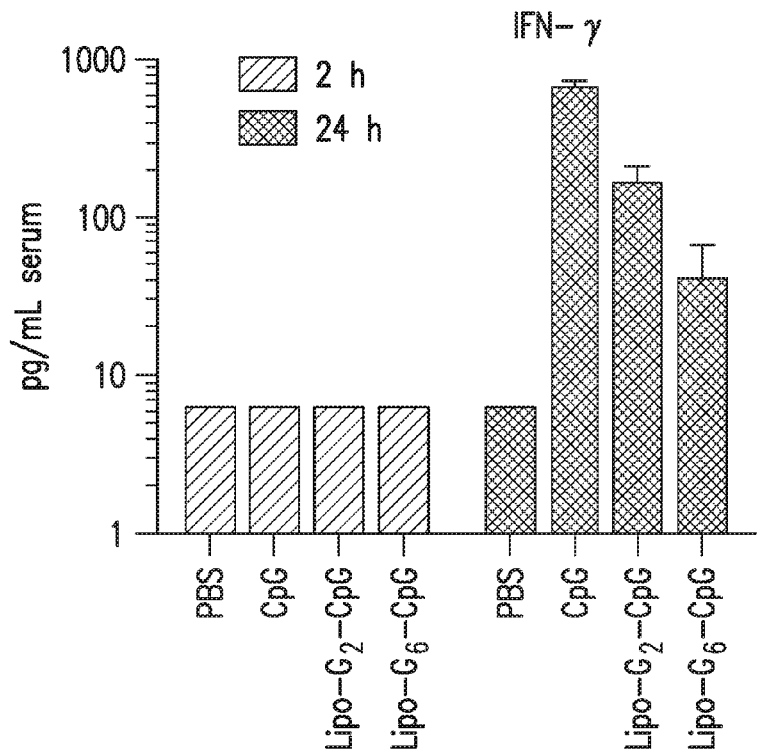
FIGS. 10A-10D are Milliplex analyses of proinflammatory cytokines elicited in peripheral blood of mice immunized with a single dose (6.2 nmol) of CpG formulations, blood samples were collect at different time interval and analyzed per manufacturer's instructions. Interferon gamma (FIG. 10A), TNF-alpha (FIG. 10B), IL6 (FIG. 10C), and IL12p40 (FIG. 10D).
Figure 10B:
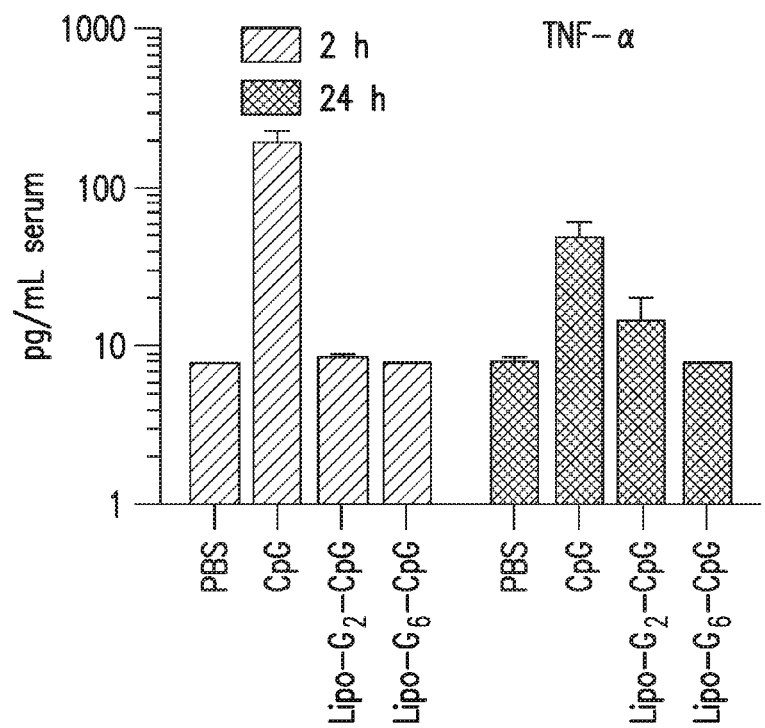
Figure 10C:
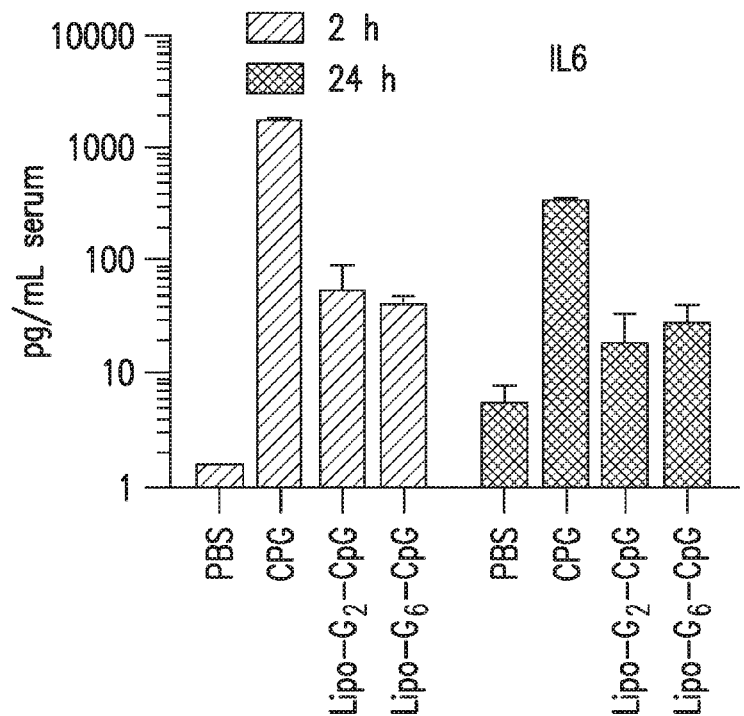
Figure 10D:
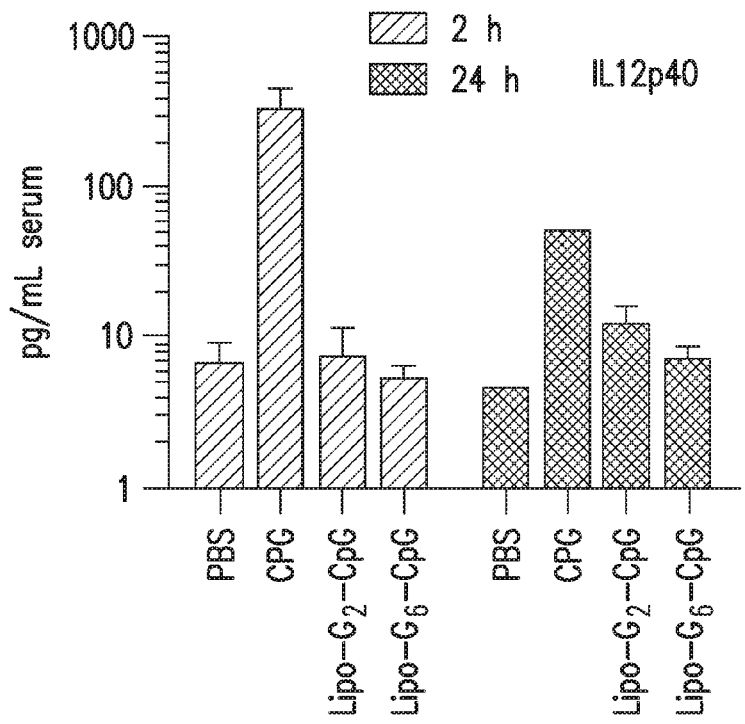

Based on design rules for efficient targeting of compounds to lymph nodes discussed above, peptide antigens were conjugated to commercially-available DSPE-PEG (18-carbon diacyl lipid tail, 2 KDa PEG block) to generate amph-peptides for use in vaccination studies (FIG. 9).

Having established the structure-function relationship between albumin binding and lymph nodes retention, experiments were designed to test whether combining antigen and CpG amphiphiles could directly impart the priming of antigen-specific immune response. A variety of peptide antigens, including virus antigen (SIV gag, AL11), tumor associated self-antigen (melanoma antigen, Trp2), and tumor specific antigen (human papillomavirus, type 16, E7, HPV-16-E7) were conjugated to maleimide functionalized DSPE-PEG$_{2000}$. Antigen conjugation did not significantly affect the albumin binding.

Figure 5B:
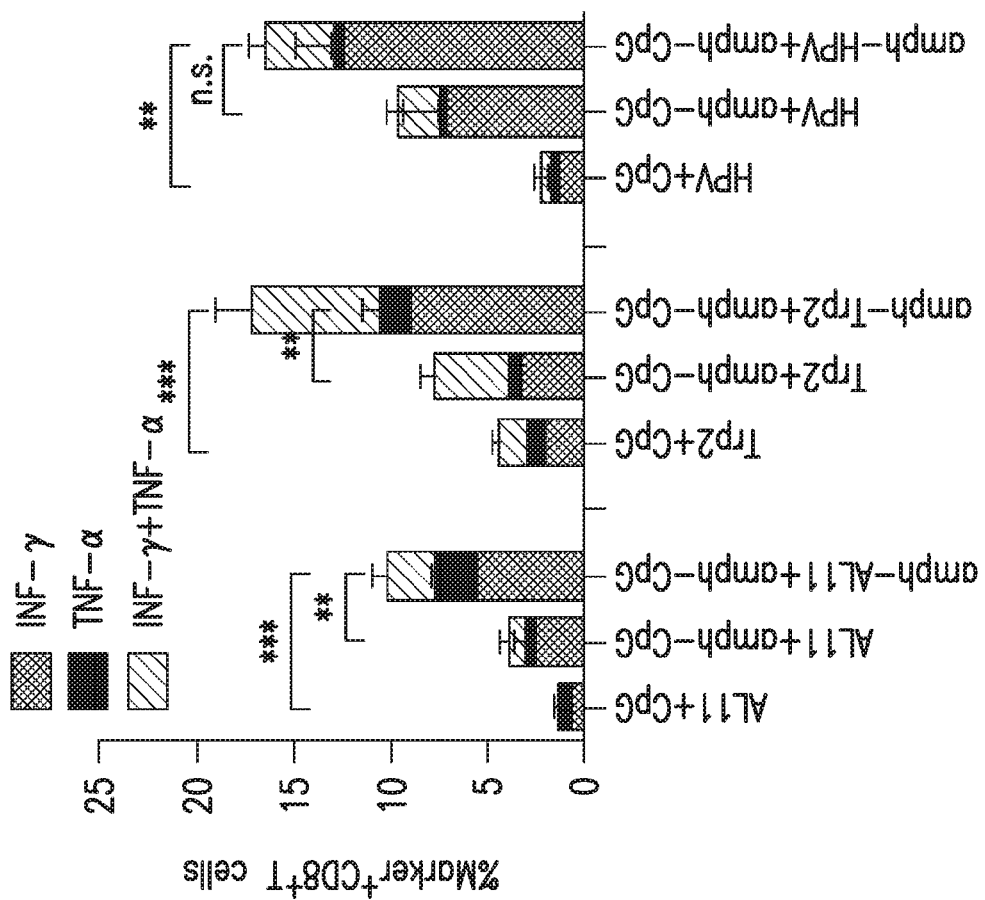
FIG. 5B is a bar graph showing quantifications of INF-γ and TNF-α positive CD8 T-Cells after 6 hrs. antigen-specific restimulation as a measure of the magnitude of antigen-specific CD8$^+$ T cell responses for minimal peptides (Al11, Trp2, and HPV-16 E7).
Figure 5A:
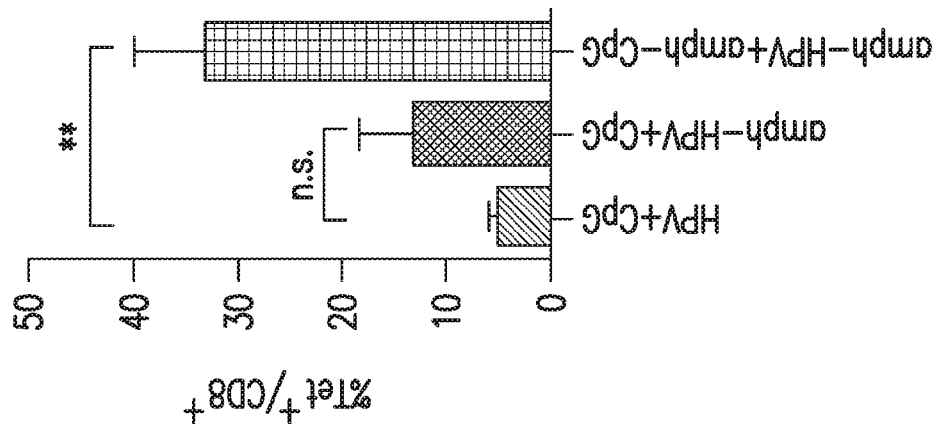
FIG. 5A is a bar graph showing the percentage of CD8+ cells isolated from C57Bl/6 mice that were HPV-16 E7$_{49-57}$ positive by flow cytometry 6 days after completion of an immunization protocol including s.c. injections on day 0 and day 14, with HPV-16 E7 minimal peptide (E7$_{49-57}$) and in combinations with 1.24 nmol CpG as indicated.

Following vaccination, the elicited CD8 T-cell responses and functionalities were monitored using tetramer techniques or intracellular cytokine staining (ICS) as discussed above. Administration of vaccines comprised of amph-antigens (DSPE-PEG$_{2000}$-peptides) and amph-CpG adjuvant (lipo-G$_2$-CpG) resulted in dramatically increased antigen-specific CD8$^+$ T-cell responses (FIGS. 5A-5B) for all of the above minimal peptide epitopes. In mice vaccinated with amph-Trp2 plus amph-CpG, a mean of 15% and 7% of CD8$^+$ lymphocyte produced IFN-γ and TNF-α, respectively. In contrast, two control groups receiving free Trp2 exhibited only marginal CTL activities (FIG. 5B).

Figure 5D:
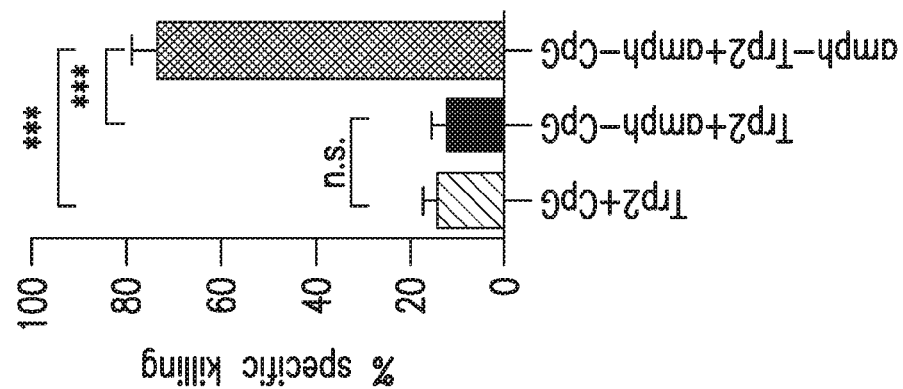
FIG. 5D is a bar graph showing the potency of amphiphilic vaccine as assayed by in vivo cytotoxicity experiment on day 7 after the final immunization of Trp2 peptide vaccines.
Figure 5C:
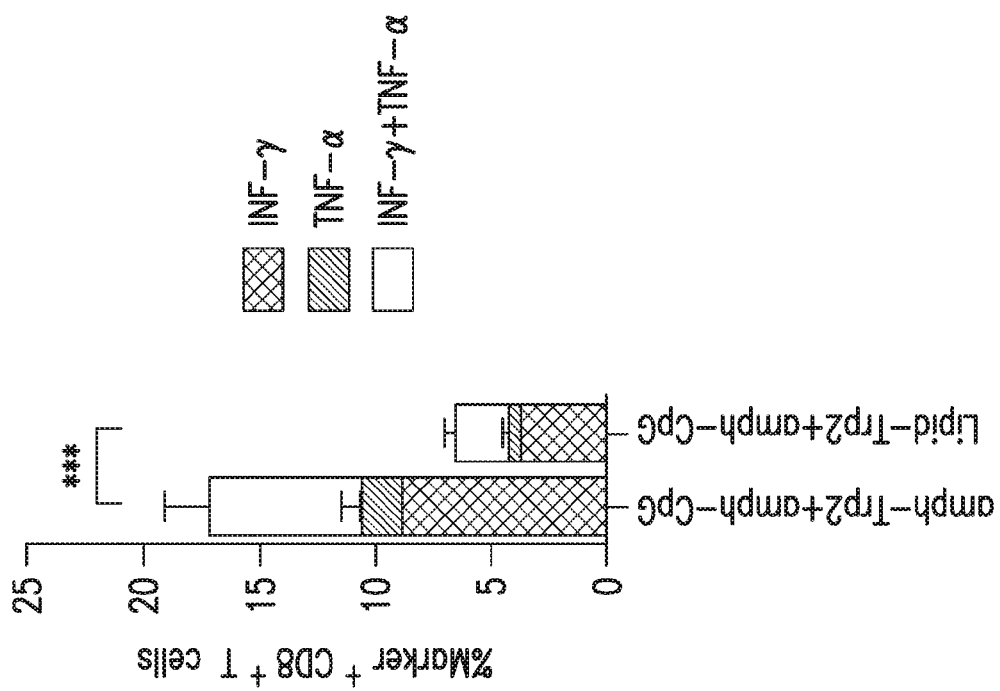
FIG. 5C is a bar graph showing direct lipid conjugate to peptide (lipopeptide) does not elicit potent antigen-specific immune response as measured by the frequency of INF-γ and TNF-α positive CD8 T-Cells after restimulation.

Directly conjugate lipid to antigen without a PEG linker resulted in a dramatic decrease of immune response, indicating a long PEG linker is necessary to elicit CD8 T-cell immune response (FIG. 5C). This observation is consistent with LN accumulation data observed before, where efficient LN retention required a long PEG spacer. The above data shows that albumin-binding vaccine formulations can induce large numbers of functional antigen-specific CD8$^+$ T-cells. Mice immunized with self-delivering formulations were consistently observed to have more potent cytotoxic activities against peptide-pulsed target populations compared with the unpulsed controls (FIG. 5D).

Example 7: Lymph Node-Targeted Vaccines Exhibit Therapeutic Efficacy

The therapeutic benefits of the CD8 responses generated following immunization were tested by treating established subcutaneous mouse tumor TC-1, which expresses the E7 oncoprotein from human papillomavirus type-16 (HPV-16). 6- to 8-wk-old C57BL/6 mice were inoculated at the left above flank with TC-1 tumor cells (3×10$^5$ cells/mouse) subcutaneously. After the formation of palpable tumor (day 6), mice were randomized and treated on day 6, day 13 and day19 with amph-HPV (DSPE-PEG-E7$_{49-57}$) combined with amph-CpG (Lipo-G$_2$-CpG) at mouse tail base, using unconjugated E7$_{49-57}$ peptide and CpG as control. Tumor growth was followed every 2-3 days.

Figure 5E:
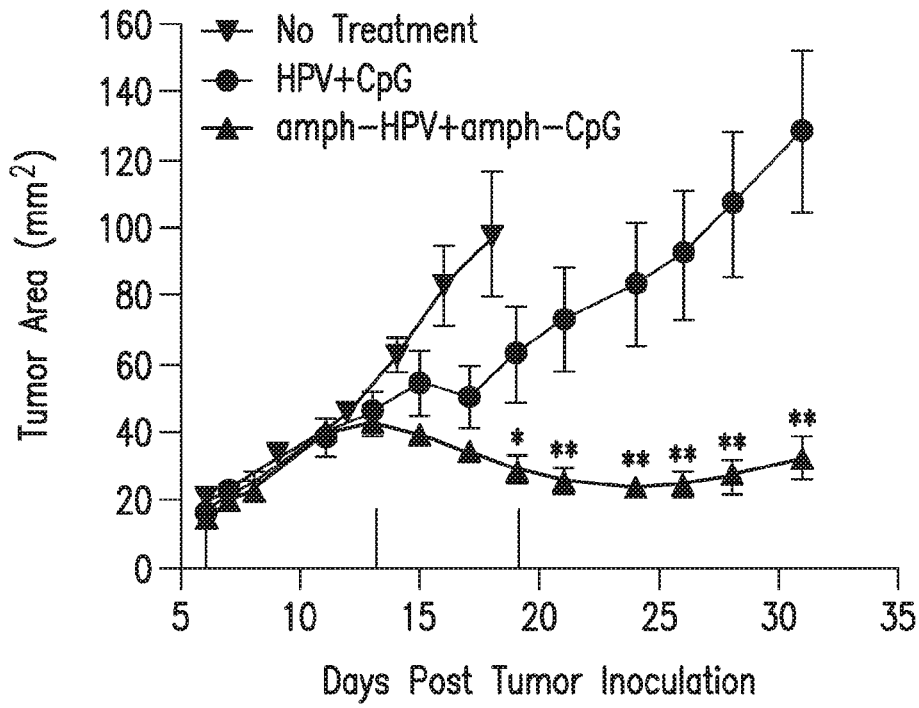
FIG. 5E is a Kaplan-Meier curve and FIG. 5F is a line graph showing tumor area for mice over time following treatment with subcutaneous (s.c.) TC-1 tumors treated by amphiphilic HPV-16 E7 peptide vaccine, soluble vaccine or no vaccine on day 6, 13 and 19 after challenge with 3×10$^5$ TC-1 cells. Statistically significant differences between amphiphilic vaccine and soluble vaccine-treated groups are indicated by asterisks. *, $p<0.001$;, $p<0.01$; *, $p<0.05$. All data are plotted as means plus or minus s.e.m. (n=3-8).
Figure 5F:
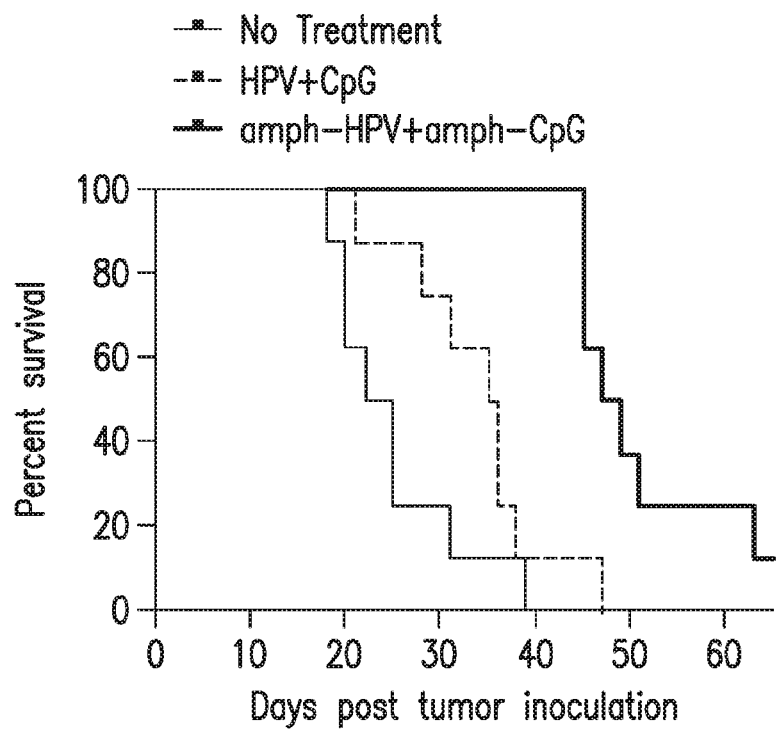
Figure 6B:
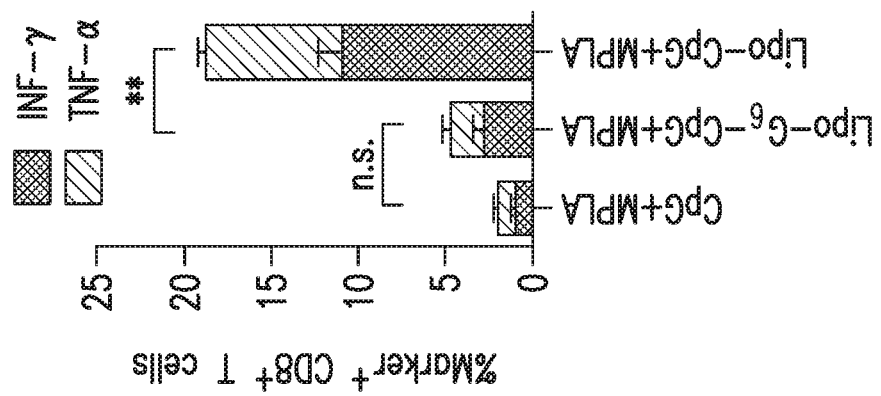
FIG. 6B is a bar graph showing the % TNF-α and INF-γ positive CD8+ T cells following treatment with free CpG and MPLA, Lipo-G$_6$-CpG-MPLA, or Lipo-CpG-MPLA.
Figure 6A:
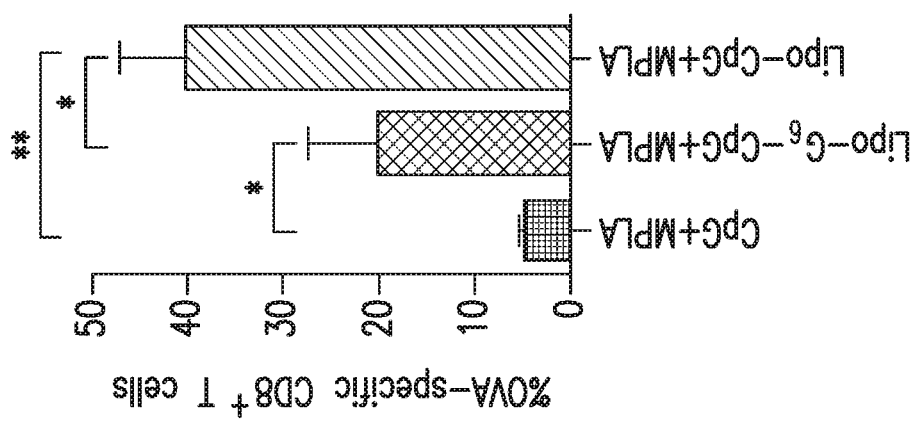
FIG. 6A is a bar graph showing the % OVA-specific CD8+ T cells following treatment with free CpG and MPLA, Lipo-G$_6$-CpG-MPLA, or Lipo-CpG-MPLA.
Figure 6C:
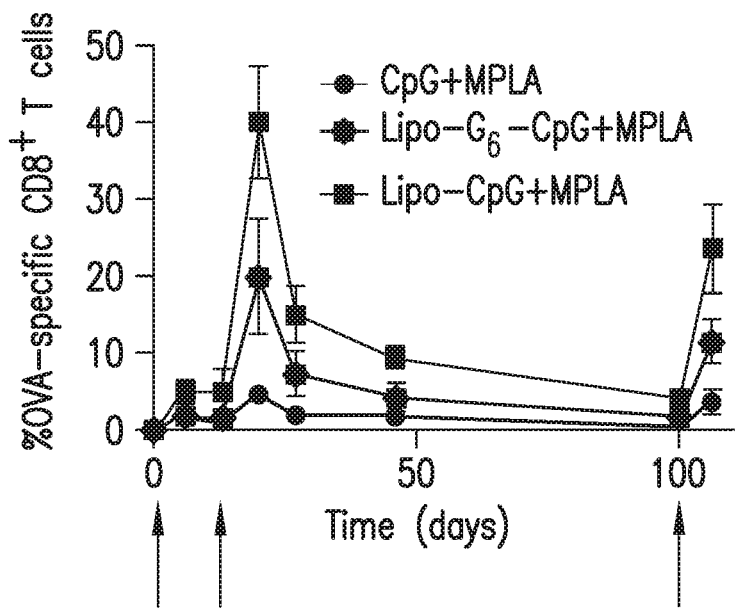
FIG. 6C is a line graph showing the % OVA-specific CD8+ T cells following treatment with free CpG and MPLA, Lipo-G$_6$-CpG-MPLA, or Lipo-CpG-MPLA over time.
Figure 6D:
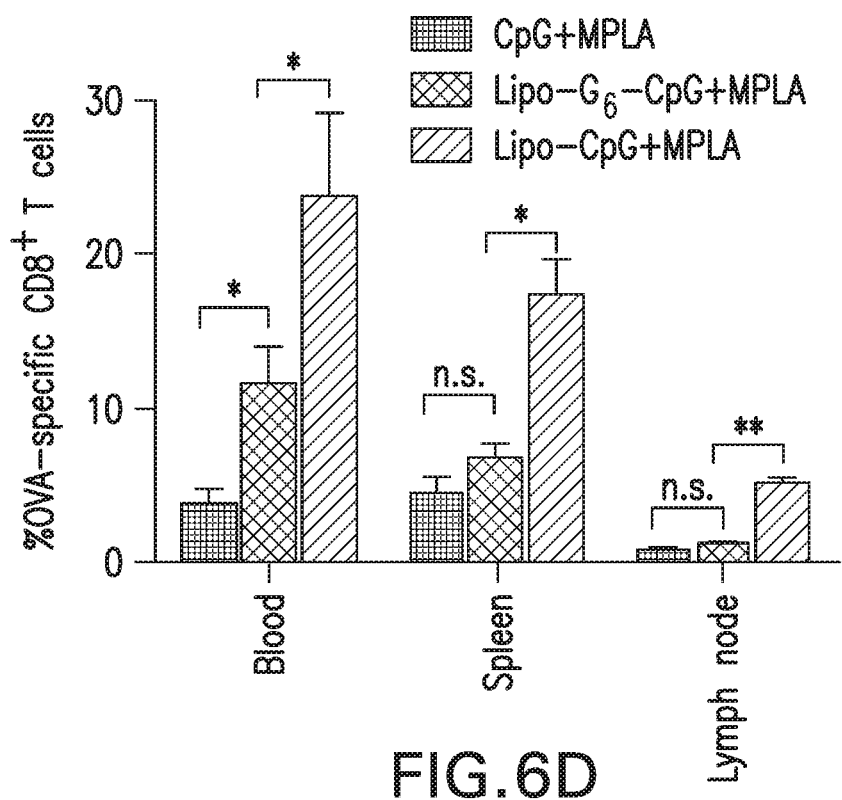
FIG. 6D is a bar graph showing the % OVA-specific CD8+ T cells following treatment with free CpG and MPLA, Lipo-G$_6$-CpG-MPLA, or Lipo-CpG-MPLA in the blood, spleen, and lymph node.

As showed in FIGS. 5E and 5F, tumors grew rapidly in mice not receiving vaccine. Mice treated by vaccine amphiphiles inhibited the growth of subcutaneously growing TC-1 tumor over several weeks (3-5 mm in diameter at the initial treatment). In contrast, treatment with unconjugated CpG oligonucleotide plus HPV-16 E7 peptide antigen had only minor antitumor effects (FIGS. 5E and 5F), leading to a transient delay of tumor growth by day 19, after which time tumors rapidly progressed. Considered together, the results demonstrate that combination of amph-peptide antigens and amph-CpG adjuvant dramatically enhances antigen-specific CTL responses and leads to improved antitumor immunity in a mouse tumor model.

Example 8: G-Quadruplex Linkers Stabilizes Oligonucleotide Micelles

Materials and Methods
Oligonucleotide Synthesis

Oligonucleotides were synthesized in 1.0 micromolar scale on an automated DNA synthesizer (ABI 394, Applied Biosystems, Inc.). All DNA synthesis reagents including cholesteryl-triethylene glycol (TEG)-phosphoramadite and DMT-polyethylene glycol (PEG)-phosphoramadite were purchased from Glenres and Chemgenes and used according to manufacturer's instructions. Immunostimulatory cytosine-guanine (CG) oligonucleotides were a type B sequence referred to as 1826 (Lipo-G$_n$-CG: 5'-diacyl lipid-G$_n$-TC-CATGACGTTCCTGACGTT-3' (SEQ ID NO:1). Synthesis of lipid phosphoramidite and solid phase conjugation was followed by previous reports. Particle size was determined by dynamic light scattering (DLS) using a 90Plus/ZetaPals particle size and ζ-potential analyzer (Brookhaven Instruments). DSPE-PEG2000-Maleimide was purchased from Laysan Bio Inc. carboxyfluorescein labeled PEG2000-DSPE were purchased from Avanti Polar lipids Inc.

Circular Dichroism

Five μM of CG oligonucleotides were dissolved in 1× phosphate buffered saline (PBS) with 20 mM KCl. Circular Dichroism (CD) spectra were recorded on an Aviv Model 202 Circular Dichroism Spectrometer at 20° C. Scans from 220 to 320 nm were performed with 100 nm/min scanning speed, 1 nm bandwidth. For each spectrum, an average of three scans was taken, and spectral contribution from the buffer was subtracted.

Size-Exclusion Chromatography

Size-exclusion chromatography was carried out on a Shimadzu HPLC system equipped with a SEC-biosil column (repacked in a 200×4.6 mm column). Samples were eluted using 1×PBS+20 mM KCl at flow rate 0.5 mL per minute. In a typical experiment, fluorescein-labeled DNA micelles (80 μL of 5 μM lipo-G$_n$T$_{10}$-nCG-Fam in 1×PBS+20 mM KCl) were incubated with 20% Fetal Bovine Serum (FBS) (20 μL) (Greiner Bio-one), samples were briefly vortexed and incubated at 37° C. for 2 hour, then diluted in 500 μL 1×PBS+20 mM KCl. Samples were then analyzed by SEC. Fetal Bovine Serum (FBS) was monitored using absorptions at 280 nm, while oligonucleotides were monitored at 480 nm (Fam peak).

Results

Figure 7A:
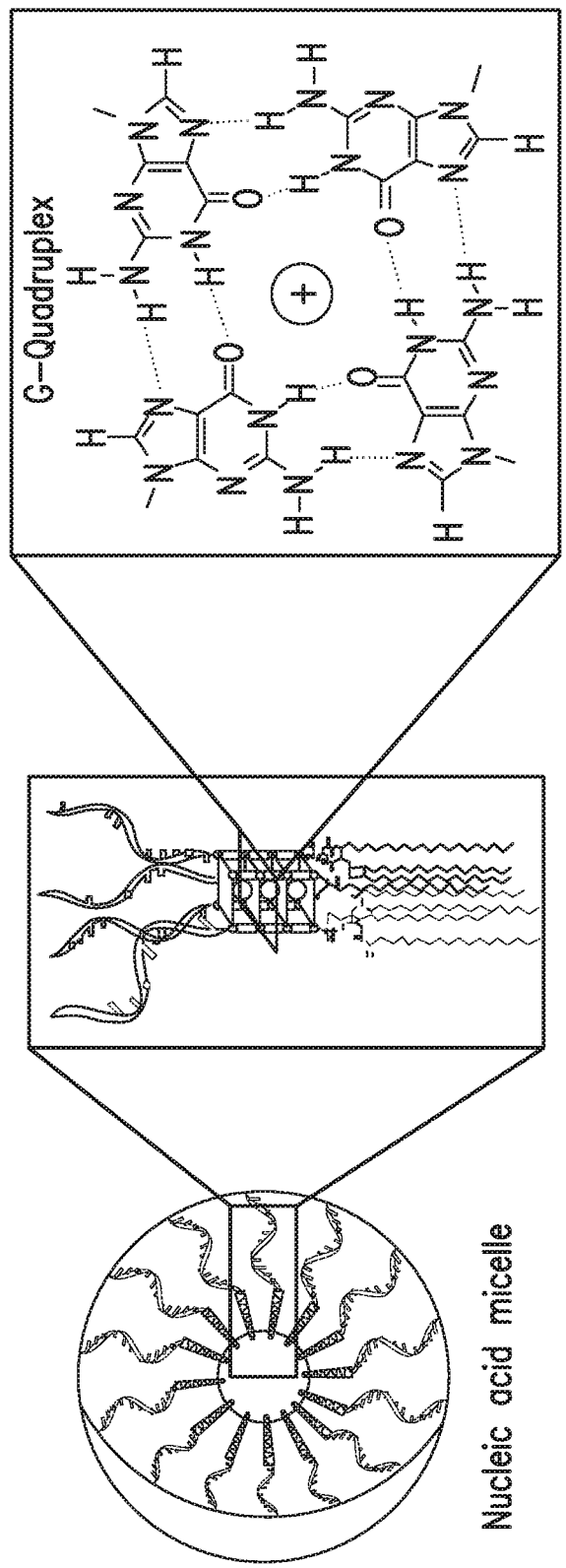
FIG. 7A is a schematic representation of an exemplary micelle formed by self-assembly of immunostimulatory conjugates, showing G-quadruplex structure formed by Hoogsteen hydrogen bonding.
Figure 7B:
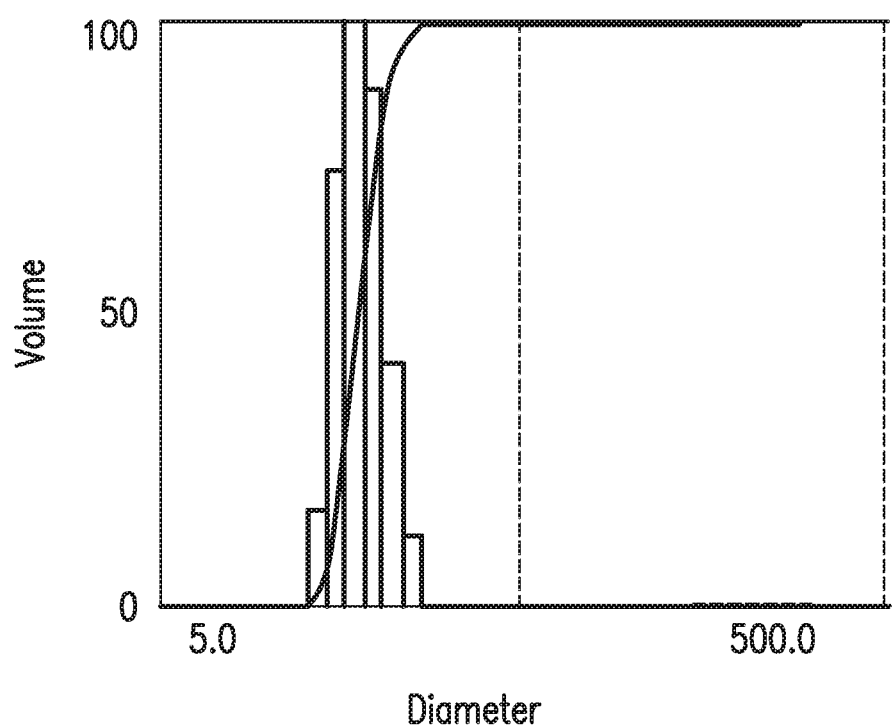
FIG. 7B is a graph showing size profile of the self-assembled micelles (diameter (nm)).

Guanine (G)-rich nucleic acid sequences can fold into various types of G-quadruplex structures (Davis, J. T. *Angew. Chem. Int. Ed. Engl.* 43, 668-698 (2004)) (e.g., intramolecular, intermolecular, parallel, and antiparallel). To facilitate micelle self-assembly and to minimize oligonucleotide folding, the lipid-oligonucleotide conjugate was first suspended in pure water, and then potassium (K$^+$) containing buffer was added to stabilize the G-quadruplex. Formation of micelles was confirmed by transmission electronic microscopy, dynamic light scattering measurements, and size-exclusion chromatography. FIG. 7B illustrates the size profile of the self-assembled micelles, which show uniform size distribution.

Figure 7C:
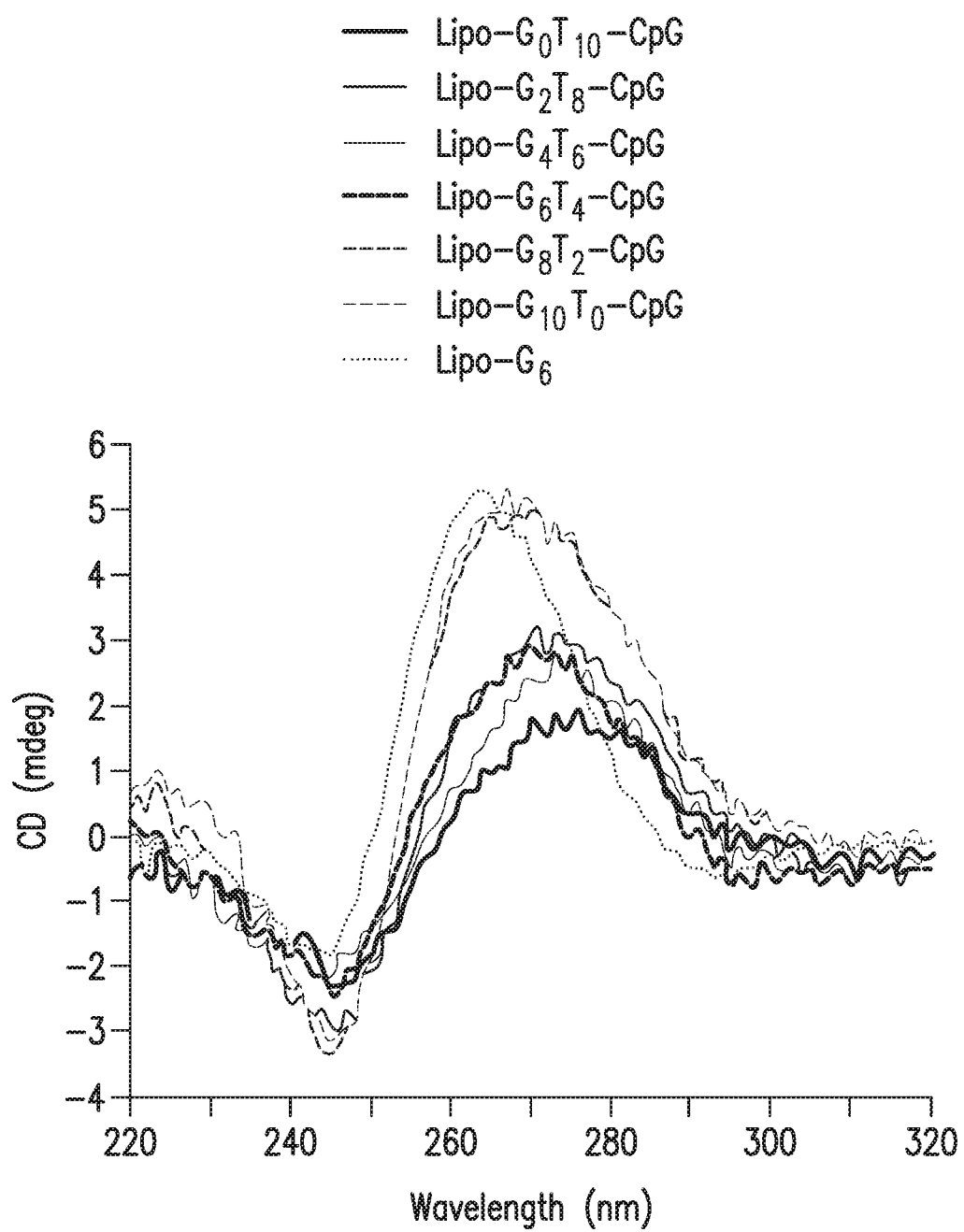
FIG. 7C is a line graph showing the results circular dichroism analysis (CD (mdeg)) of G-quadruplex stabilized micelles in 1×PBS/20 mM K$^+$.

Circular dichroism (CD) was conducted to characterize the formation of G-quadruplex. The spectrum of Lipo-G$_{10}$T$_{10}$-CG oligonucleotide showed a small negative peak near 245 nm and a positive peak near 278 nm, while changing the number of guanines from zero to ten induced a parallel G-quadruplex, as manifested by the shifting of positive peak from 278 nm toward 262 nm (signature bands for parallel G-quadruplex) (Paramasivan, S., et al., *Methods* 43, 324-331 (2007)), while retaining the negative 245 nm bands (FIG. 7C).

Figure 3A:
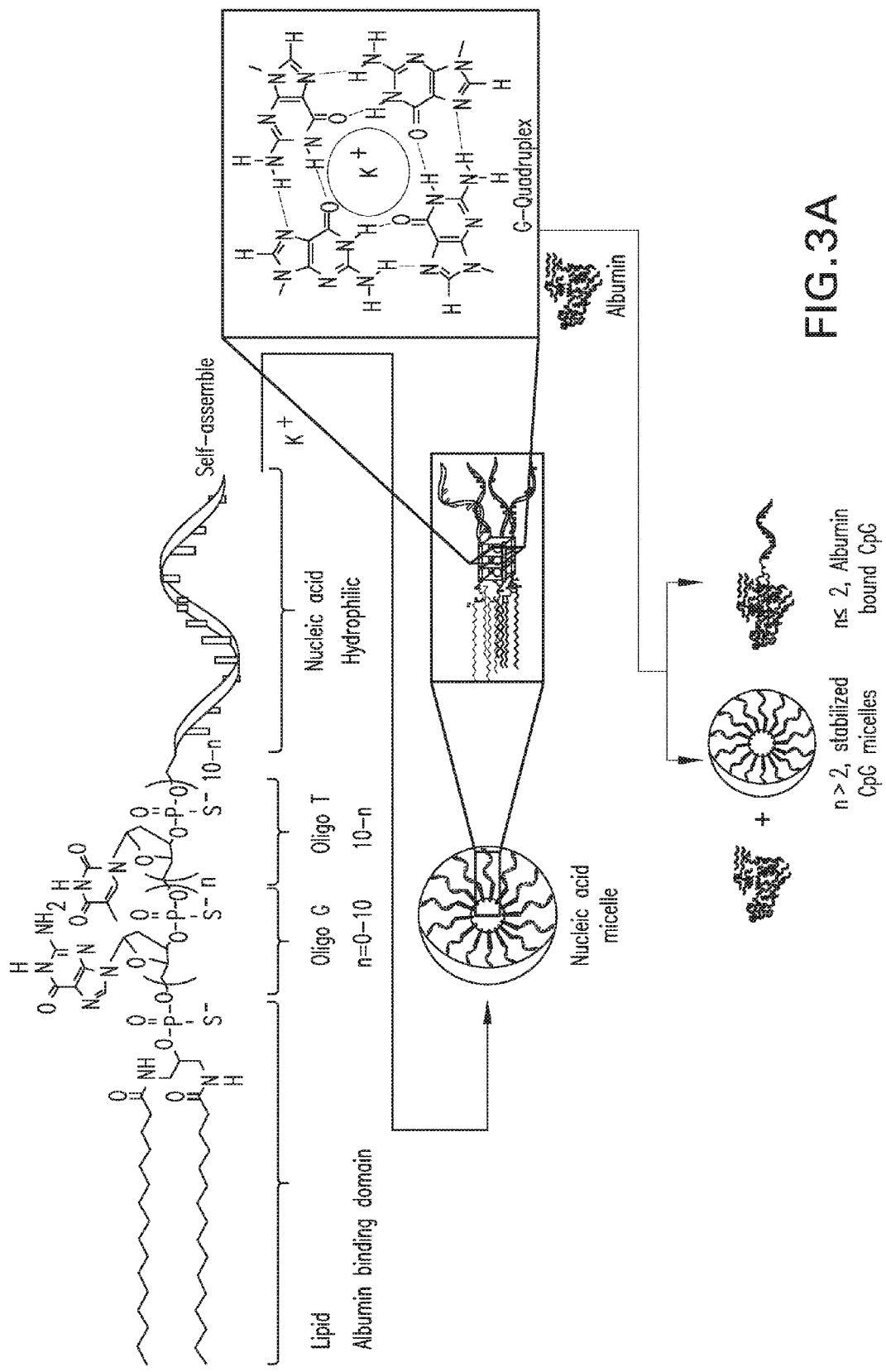
FIG. 3A is a schematic showing the generalized construction and characterizations of G-quadruplex stabilized CpG adjuvants. G-quadruplex stabilized CpG micelles are self-assembled from an ODN composed of three segments: an immunostimulatory CpG-ODN, a central repeat block contained n=1-10 G-quartet-forming guanines followed by 10-n non-interacting thymidines and a diacyllipid tail. In buffer, the ODN self-assemble into three-dimensional spherical micelles with a CpG corona and a lipid core. In the presence of K$^+$, guanine repeats form G-quadruplex structures via Hoogsteen hydrogen bonds and stabilize the micelle structure. The ODN micelles' stabilites in the presence of albumin can be programmed by simply alter the number of guanines. Albumin binds to lipid moiety of unstabilized micelles (n<2), in contrast, stabilized micelles (n>2) restrict the albumin binding and remain as micellar assemblies.
Figure 3B:
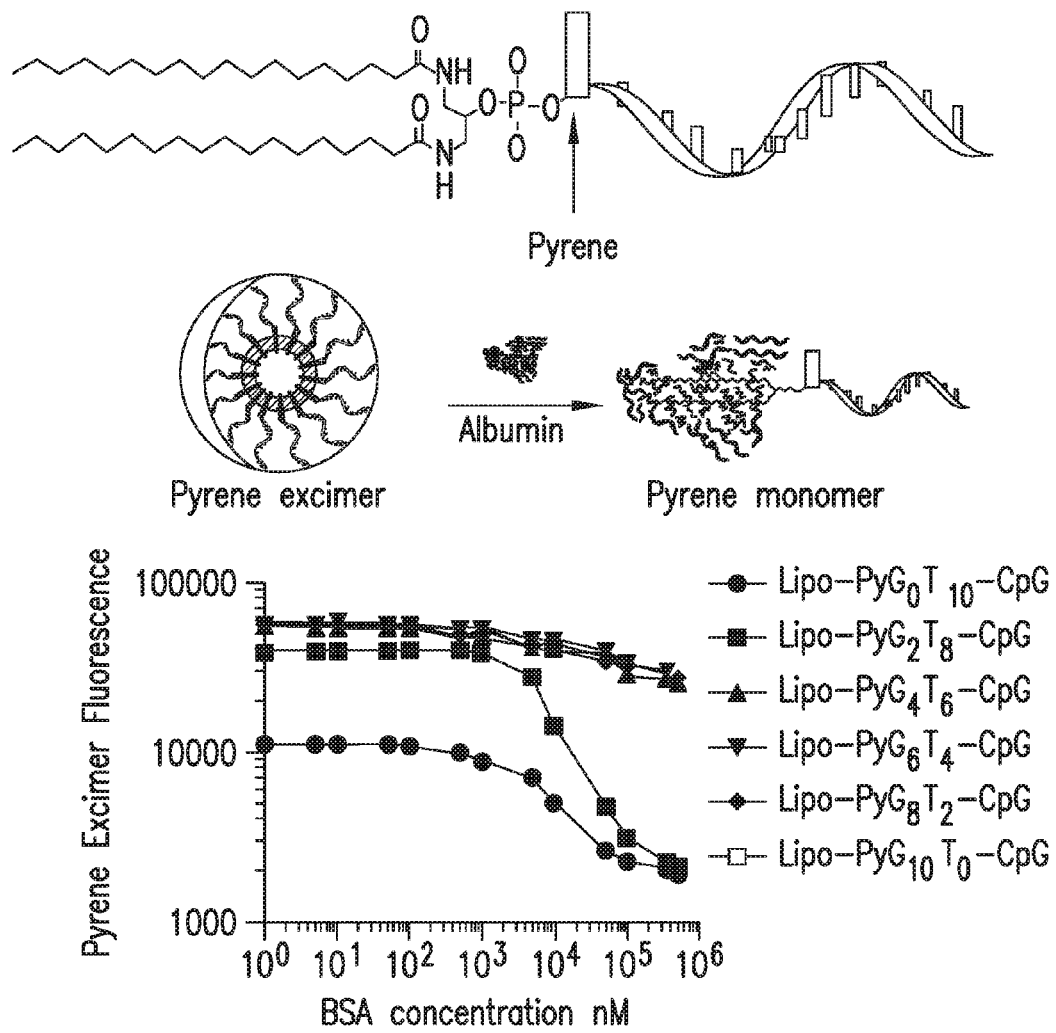
FIG. 3B is a schematic (top) and a bar graph (bottom) showing pyrene excimer fluorescent constructs used to assay the stabilities of G-quadruplex micelles in the presence of albumin.
Figure 3C:
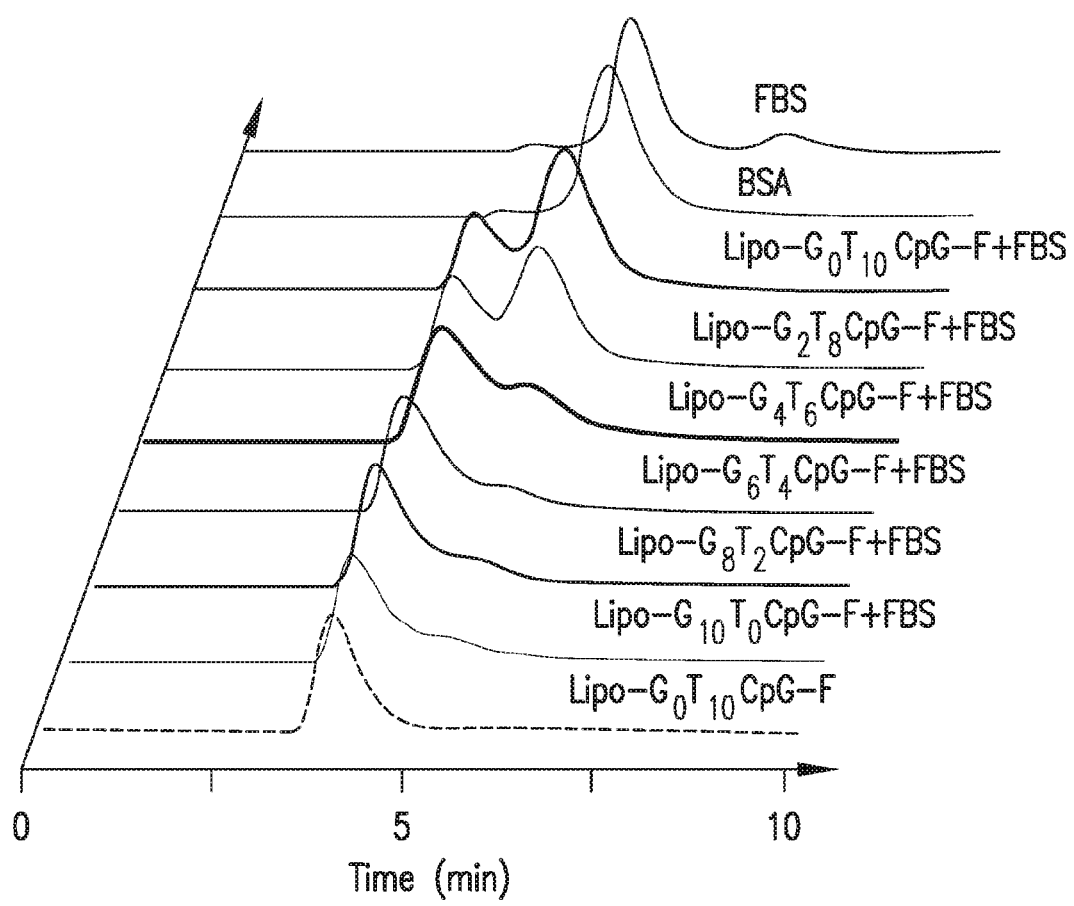
FIG. 3C is a line graph showing the stability profiles of G-quadruplex CpG micelles as measured by size-exclusion chromatography in the presence of fetal bovine serum (FBS).
Figure 3D:
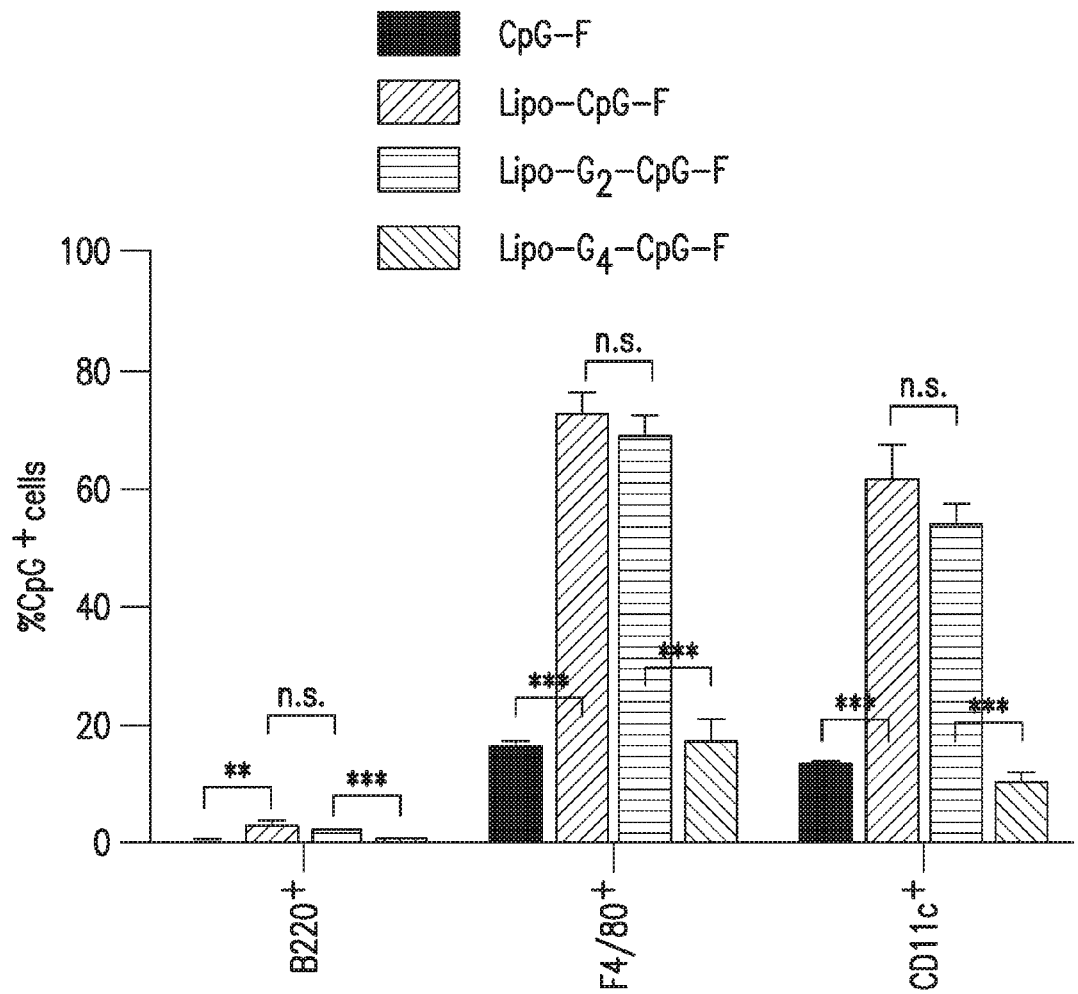

The design of G-quadruplex stabilized CpG adjuvants is shown in FIG. 3A. G-quadruplex stabilized CpG micelles are self-assembled from an ODN composed of three distinct segments: an immunostimulatory CpG-ODN, a central repeat block contained n=1-10 G-quartet-forming guanines followed by 10-n non-interacting thymidines and a diacyl-lipid tail (FIG. 3A). Pyrene excimer fluorescence was used to assay the stabilities of G-quadruplex micelles in the presence of albumin (FIG. 3B). Pyrene dye incorporated in stabilized CpG micelles (n>2) retains the excimer fluorescence in the presence of high concentration of albumin. In contrast, albumin binds to the lipids moiety of unstabilized micelles (n≤2) and disrupts the micelle structures, results in a decrease of excimer fluorescence in an albumin concentration dependent manner (FIG. 3B). The stability of the DNA micelles in the presence of serum protein was also investigated by size-exclusion chromatography (SEC) (FIG. 3C). Micelles have relatively high molecular mass thus they eluted at 3.7 minutes, while FBS showed a major peak at 5.3 minutes. After incubation, 20% of the non-stabilized micelles (lipo-$G_0T_{10}$-CG) were intact, while the remaining 80% were disrupted and bonded with FBS components (peaked at 5.2 min). In the presence of guanines, the percentage of intact micelles increased from 36% (lipo-$G_2T_8$-CG) to 73% (lipo-$G_4T_6$-CG), and finally reached 90% (lipo-$G_6T_4$-CG). Increasing the number of guanines to eight (lipo-$G_8T_2$-CG) and ten (lipo-$G_{10}T_0$-CG) did not further enhance micelle stability. Altering the number of guanines between the CPG-oligonucleotide and lipid tail controls micelle stability in the presence of serum proteins, as evidenced from the FBS peak.

Taken together, these experiments demonstrated that the G-quadruplex micelle stability under micelle disrupting conditions can be controlled by altering the number of guanines.

Example 9: G-Quadruplex Linkers Influence Lymph Node Accumulation and Cell Uptake Materials and Methods
Mice C57BL/6 albino mice (6-8 weeks) were obtained from the Jackson Laboratory. Animals were cared for in the USDA-inspected Massachusetts Institute of Technology (MIT) Animal Facility under federal, state, local and NIH guidelines for animal care.

Isolation of Bone Marrow Cells

Bone marrow-derived dendritic cells were prepared following a modification of the procedure of Inaba as previously reported. Dendritic cells were activated/matured with 500 nM CG probes for 12 hours and washed three times with PBS before use. Cells were cultured in complete medium (MEM, 5% fetal bovine serum (Greiner Bio-one), 100 units (U)/ml penicillin G sodium and 100 µg/ml streptomycin (Pen/Strep), MEM sodium pyruvate (1 mM), NaH2CO3, MEM vitamins, MEM non-essential amino acids (all from Invitrogen), and 20 µM β-mercaptoethanol (β-ME)).

In Vivo Imaging and Flow Cytometry

The draining lymph nodes of each group of mice were analyzed by In Vivo Imaging Systems (IVIS®) and flow cytometry 24 and 72 hours post-injection. All antibodies for flow cytometry were purchased from BD Pharmingen or Ebioscience.

Statistical Analysis

All error bars represent SEM. Comparisons of mean values were performed using unpaired Student's t tests. *, $p<0.05$; , $p<0.01$; *, $p<0.001$. GraphPad Prism 5 software was used.

Results

The lymphatic system absorbs interstitial fluid from tissue and returns it to the blood via lymph nodes. Animal experiments were conducted to assess micelle targeting to the lymphatic system. Dye-labeled CG oligonucleotides, dye-labeled CG oligonucleotides emulsified in IFA, or dye-labeled lipo-$G_n$-CG micelles (n=0, 2, 4, or 6) were injected subcutaneously into separate groups of mice. The draining lymph nodes of each group of mice were analyzed by In Vivo Imaging Systems (IVIS®) and flow cytometry 24 and 72 hours post-injection. Cells were acquired on a FAC-Scanto flow cytometer (BD Biosciences) and analyzed using Flowjo software (Tree Star Inc. Ashland, Oreg.).

Figure 8B:
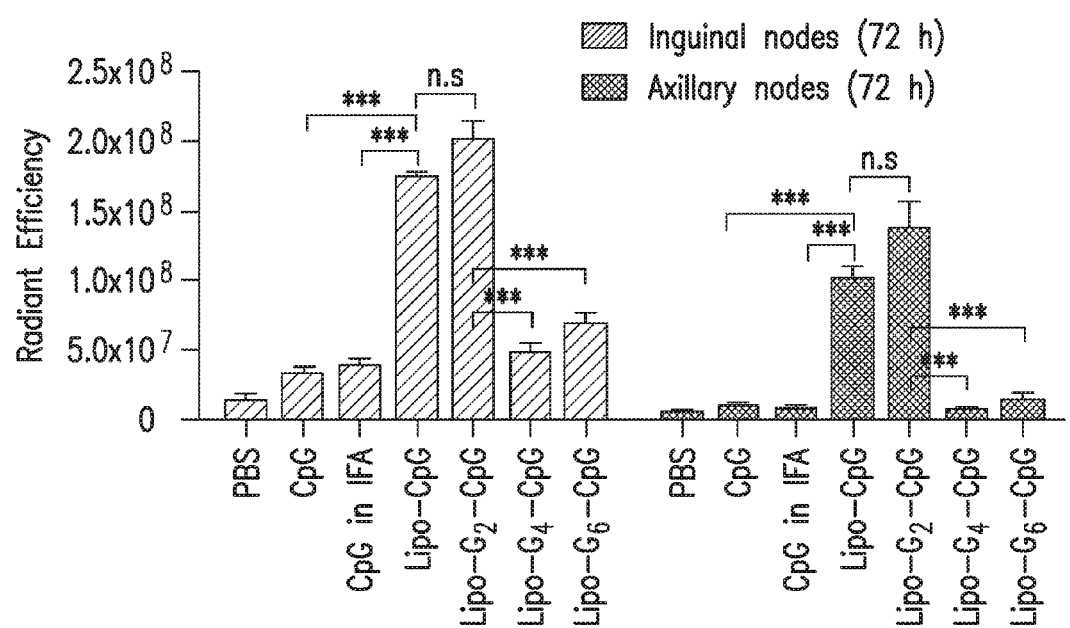
FIG. 8B is a bar graph showing quantitative accumulation (Radiant Efficiency) of various CpG-based micelles in the inguinal lymph nodes (left half of the graph) and axillary lymph nodes (right half of the graph) 72 hours post injection.

All lymph nodes were visibly enlarged, reaching maximum enlargement by 24 hours. Fluorescence imaging of the isolated lymph nodes at 24 and 72 hours revealed a significant difference among the different groups of mice. The number of modestly-stabilized lipo-$G_n$-CpG micelles (n=0 or 2) retained by the inguinal (proximal lymph node) and axillary (distal lymph nodes) lymph nodes was greater than the number of over-stabilized lipo-$G_n$-CpG micelles (n=4 or 6) retained, with peak lymph node targeting achieved by lipid-$G_2$-CpG micelles (FIGS. 8A and 8B). 72 hours after injection, uptake of destabilized lipid-$G_{(0\ or\ 2)}$-CpG micelles by dendritic cells (DCs) increased by 5-fold, uptake by macrophages increased by 8-fold, and uptake by B cells increased by 5-fold, as compared to soluble CpG oligonucleotides. By contrast, more stable lipo-$G_{(4\ or\ 6)}$-CG micelles exhibited a low level of lymph node retention and cell association.

Example 10: Immunostimulatory Micelles Induce Antigen-Specific $CD8^+$ T-Cell Expansion Materials and Methods Mouse $CD8^+$ T-cell expansion was examined following immunization/vaccination with modestly-stabilized (lipo-$G_{(0\ or\ 2)}$-CpG oligo) or over-stabilized (lipo-$G_{(4\ or\ 6)}$-CpG oligo) immunostimulatory micelles, using soluble CpG oligonucleotide as a control. C57B16 (B6) Mice were vaccinated on days 0 and 14 and analyzed on day 20 or 21. Typically, each injection contained the following ingredients: 10 µg ovalbumin (OVA) antigen (purchased from Worthington Biochemical Corporation) and 1.24 nmol lipo-$G_n$-CG micelle suspended in 1×PBS (20 mM $K^+$ and 10 mM $Mg^+$). Ovalbumin (OVA) was used as a model antigen because it has a well-studied H-2 Kb-restricted MHC class I epitope in B6 mice. In experiments in which Incomplete Freund's adjuvant (IFA) was used, a volume of soluble CpG oligonucleotides and soluble OVA antigen were combined with an equal volume of IFA and emulsified. The total volume of each vaccine injection was 100 µl. Mice were injected subcutaneously at the base of the tail. Post-immunization, blood samples were collected from spleens and lymph nodes, and single-cell suspensions were prepared (red blood cells were depleted by ACK lysing buffer). The blood sample preparations were evaluated by MHC class I-restricted $OVA_{257-264}$ tetramer staining to track SIINFEKL-specific $CD8^+$ T-cell expansion. Cysteine (cys) modified peptide $OVA_{257-264}$ (CSIINFEKL) was synthesized by GenScript and purified by reverse phase HPLC. Cells were then blocked with Fc-blocker (anti-mouse CD16/CD32 monoclonal antibody) and stained with PE labeled Kb/SIINFEKL tetramer (Beckman Coulter) and anti-CD8-APC for 30 minutes at room temperature. Cells were washed twice and resuspended in FACS buffer. FACS data were collected on a BD FACScanto flow cytometer and analyzed using Flowjo software. Analysis typically gated on $CD8^+$, Tetramer positive live cells.

Results

Administration of the immunostimulatory micelles resulted in expansion of CD8+ T-cells specific for $OVA_{257-264}$ (FIGS. 4A and 4B). Unexpectedly, the modestly-stabilized lipo-$G_2$-CpG oligo-based micelles were the most effective in stimulating SIINFEKL-specific $CD8^+$ T-cell expansion. Six days after the second (boost) injection of the destabilized lipo-$G_2$-CpG oligo-based micelles, approximately 33% of all CD8+ T-cells detected in the blood were specific for the antigen, while only approximately 7% of all CD8+ T-cells were antigen specific following administration of the boost with stabilized lipo-$G_6$-CpG oligo-based micelles. Thus, the strength of the T-cell response stimulated by this vaccine was directly correlated with modestly-stabilized CpG micelles that exhibited maximal accumulation in lymph nodes.

To examine the responsiveness of the $CD8^+$ T cells, blood lymphocytes were re-stimulated ex vivo for 6 hours with the OVA-specific peptide, SIINFEKL, and analyzed for the production of cytokines, IFN-$\gamma$ and TNF-$\alpha$. Cells were plated in 96-well round-bottomed plates and pulsed with minimum peptides in the presence of brefeldin A for 6 hours in complete media at 37° C. Cells were stained with anti-CD8-APC and then fixed using Cytofix (BD biosciences) according to the manufacturer's instructions. Cells were then washed and permeabilized. Intracellular staining for anti-INF-$\gamma$-PE and anti-TNF-$\alpha$-FITC was then performed according to BD's protocol. FACS data were collected and analyzed as described. Again, the destabilized lipo-$G_2$-CpG oligo-based micelles were the most effective (FIG. 4B), correlating with the above findings.

Additional in vivo cytotoxic lymphocyte (CTL) assays were conducted to assess whether the expanded $CD8^+$ T cell populations were functional. Splenocytes from naïve mice were pulsed with or without 10 µM SIINFEKL peptide for 30 min. Cells were then labeled with either 1 µM (for pulsed cells) or 0.1 µM (control cells) CFSE for 10 min at 37° C. and extensively washed. Cells were mixed at a 1:1 ratio and $10 \times 10^6$ total cells were injected intravenously (i.v.) into mice challenged previously with vaccine formulations as described above. Post 18 hours, splenocytes from each recipient mouse were analyzed by FACS to detect the CFSE labeled cells. $CD8^+$ T cells from mice immunized with immunostimulatory lipo-$G_n$-CG-based micelles lysed >97.9% of the peptide-pulsed target population, whereas $CD8^+$ T cells from mice immunized with soluble CpG oligonucleotide lysed an average 54.6% of target cells.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

We claim:

1. A peptide conjugate comprising a peptide which is linked to a linker which is conjugated to an albumin-binding domain,
   wherein the linker, or the peptide and linker in combination, is sufficiently polar to reduce insertion of the conjugate into a cell's membrane relative to the same peptide conjugate without the linker, and
   wherein the conjugate is sufficiently soluble to bind to albumin under physiological conditions.

2. The peptide conjugate of claim 1 wherein the linker is selected from the group consisting of polymers, a string of amino acids, nucleic acids, polysaccharides, and combinations thereof.

3. The peptide conjugate of claim 1 wherein the linker comprises "N" consecutive ethylene glycol units, wherein N is 25-50.

4. The peptide conjugate of claim 1 wherein accumulation of the peptide conjugate in the lymph node following administration to a subject in vivo is increased relative to administration of the peptide alone.

5. A method of increasing an immune response in a subject comprising administering to the subject an effective amount of the peptide conjugate of claim 1 to increase the immune response in the subject.

6. The method of claim 5 wherein the immune response is an increase in the number of CD8+ T cell expressing TNF-$\alpha$, or IFN-$\gamma$ compared to a control.

7. The method of claim 5 wherein the subject has cancer or an infectious disease.

8. A method of treating cancer or an infectious disease comprising administering to the subject an effective amount of the peptide conjugate of claim 1 to reduce one or more symptoms of the cancer or infectious disease compared to a control.

9. The peptide conjugate of claim 1, wherein accumulation of the conjugate in the lymph node following administration to a subject in vivo is increased relative to administration of the peptide conjugate in the absence of the linker.

10. The peptide conjugate of claim 1, wherein the linker comprises a polyethylene glycol unit.

11. The peptide conjugate of claim 10, wherein the linker comprises more than 24 units of ethylene glycol.

12. The peptide conjugate of claim 11, wherein the linker comprises 48 units of ethylene glycol.

13. The peptide conjugate of claim 11, wherein the linker comprises no more than about 100 units of ethylene glycol.

14. The peptide conjugate of claim 11, wherein the linker comprises between about 30 and about 80 units of ethylene glycol.

15. The peptide conjugate of claim 11, wherein the linker comprises between about 20 and about 80 units of ethylene glycol.

16. The peptide conjugate of claim 11, wherein the linker comprises between about 30 and about 70 units of ethylene glycol.

17. The peptide conjugate of claim 11, wherein the linker comprises between about 40 and about 60 units of ethylene glycol.

18. The peptide conjugate of claim 11, wherein the linker comprises between about 45 and about 55 units of ethylene glycol.

19. The peptide conjugate of claim 2, wherein the linker is a hydrophilic polymer.

20. The peptide conjugate of claim 2, wherein the linker is a string of hydrophilic amino acids.

21. The peptide conjugate of claim 1, wherein the peptide is derived from a virus, a bacterium, a parasite, a plant, a protozoan, a fungus, a tissue or a transformed cell.

22. The peptide conjugate of claim 21, wherein the transformed cell is a cancer cell.

23. The peptide conjugate of claim 1, wherein the albumin-binding domain is a lipophilic molecule.

24. The peptide conjugate of claim 23, wherein the lipophilic molecule is a lipid.

25. An immunogenic composition comprising a plurality of the peptide conjugates of claim 1.

26. The immunogenic composition of claim 25, further comprising an adjuvant.

27. The immunogenic composition of claim 26, wherein the adjuvant is selected from the group consisting of Freund's adjuvant, alum, saponins, poly[di(carboxylatophenoxy)phosphazene (PCPP polymer), Flt3 ligand, *Leishmania* elongation factor, Iscom, Pam3Cys, SB-AS4, non-ionic block copolymers that form micelles, Montanide IMS, virosomes and viral-like particles, bacterial and microbial derivatives, immunostimulatory oligonucleotides, ADP-ribosylating toxins and detoxified derivatives, mineral-containing compositions, bioadhesives, mucoadhesives, microparticles, liposomes, polyoxyethylene ether, polyoxyethylene ester, polyphosphazene, muramyl peptides, imidazoquinolone compounds, surface active substances, TLR ligands, cytokines, interleukins, interferons, macrophage colony stimulating factor, and tumor necrosis factor.

28. A composition comprising a plurality of the peptide conjugates of claim 1.

29. The composition of claim 28, wherein the plurality of peptide conjugates comprises two or more species of peptide conjugates comprising different albumin-binding domains.

30. The composition of claim 28, wherein the plurality of peptide conjugates comprises two or more species of peptide conjugates comprising different peptides.

31. The composition of claim 28, wherein the plurality of peptide conjugates comprises two or more species of peptide conjugates comprising different linkers.

32. The peptide conjugate of claim 1, wherein the albumin binding domain is a lipid or lipophilic domain.

33. The peptide conjugate of claim 1, wherein the linker is hydrophilic.

34. A peptide conjugate comprising a peptide which is linked to a linker which is conjugated to an albumin-binding domain,
wherein the linker is selected from the group consisting of polymers, a string of amino acids, nucleic acids, polysaccharides, and combinations thereof,
wherein the linker, or the peptide and linker in combination, is sufficiently polar to reduce insertion of the conjugate into a cell's membrane relative to the same peptide conjugate without the linker, and
wherein the conjugate is sufficiently soluble to bind to albumin under physiological conditions.

35. The peptide conjugate of claim 24 wherein the lipid is a diacyl lipid.

36. The peptide conjugate of claim 24 wherein the acyl chains of the lipid comprise 12-30 hydrocarbon units.

* * * * *